US008617545B2

(12) United States Patent
Hsu et al.

(10) Patent No.: US 8,617,545 B2
(45) Date of Patent: Dec. 31, 2013

(54) METHODS FOR USE WITH BAFF ANTAGONISTS

(75) Inventors: Yen-Ming Hsu, Lexington, MA (US); Leonid Gorelik, Quincy, MA (US); Tatiana Novobrantseva, Wellesley, MA (US); Joanne Quan, San Francisco, CA (US); Flavius Martin, Hayward, CA (US); Susan L. Kalled, Concord, MA (US)

(73) Assignees: Biogen Idec MA Inc., Cambridge, MA (US); Genentech, Inc., South San Francisco, CA (US)

( * ) Notice: Subject to any disclaimer, the term of this patent is extended or adjusted under 35 U.S.C. 154(b) by 945 days.

(21) Appl. No.: 12/083,614

(22) PCT Filed: Oct. 12, 2006

(86) PCT No.: PCT/US2006/039803
§ 371 (c)(1),
(2), (4) Date: Aug. 27, 2010

(87) PCT Pub. No.: WO2007/047335
PCT Pub. Date: Apr. 26, 2007

(65) Prior Publication Data
US 2010/0330066 A1 Dec. 30, 2010

Related U.S. Application Data

(60) Provisional application No. 60/726,406, filed on Oct. 13, 2005.

(51) Int. Cl.
*A61K 39/395* (2006.01)
*A61K 38/16* (2006.01)
*C12Q 1/00* (2006.01)
*C12Q 1/68* (2006.01)

(52) U.S. Cl.
USPC .............. 424/130.1; 514/12; 435/4; 435/6

(58) Field of Classification Search
None
See application file for complete search history.

(56) References Cited

FOREIGN PATENT DOCUMENTS

WO    WO 02/18574 A2    3/2002
WO    WO 2004/094620 A2    11/2004

OTHER PUBLICATIONS

Gorelik et al., Cutting edge: BAFF regulates CD21/35 and CD23 expression independent of its B cell survival function. J. Immunol. 172:762-766, 2004.*
Rab, Eva L., et al., "A Microarray analysis tool applied to BAFF-stimulated B cell data", Database Biosis [Online], Biosciences Information Service, Philadelphia, 2004, XP002434291, Database accession No. PREV200400286913, abstract.
Zhang, Yan et al., Selective Targeting of the Transitional and Marginal Zone B Cells with a BLyS Neutralizing Antibody Inhibits Autoimmune Response in Human BLyS Transgenic Mice, FASEB Journal (Federation of American Societies for Experimental Biology), Bethesda, vol. 19, No. 4, Sup S Part 1, Mar. 6, 2005, p. A886, XP009081652, ISSN: 0892-6638.
Kayagaki, Nobuhiko et al., "BAFF/BLyS receptor 3 binds the B cell survival factor BAFF ligand through a discrete surface loop and promotes processing of NF-kappaB2", Immunity, Cell Press, US, vol. 17, No. 4, Oct. 2002, pp. 515-524, XP002321480, ISSN: 1074-7613, abstract.
Kanakaraj, P. et al., "BLyS Binds to B Cells with High Affinity and Induces Activation of the Transcription Factors NF-kappaB and ELF-1", CYTOKINE, Jan. 7, 2001, pp. 25-31, XP002434394, ISSN: 1043-4666, pp. 28-29, "BLyS induced signaling in B cells", abstract.
Kalled, Susan L., "The role of BAFF in immune function and implications for autoimmunity".
Immunological Reviews, Munksgaard, vol. 204, No. Apr., Apr. 2005, pp. 43-54, XP002419142, ISSN: 0105-2896, pp. 47-48 "Regulation of B-cell-surface molecules".
Maia, Sara et al., "Aberrant Expression of BAFF System Molecules on B-Cell Precursor Leukemia Modulates Tumor Cell Survival: Novel Targets for Therapeutic Intervention", Blood, W.B. Saunders Company, Orlando, FL, vol. 104, No. 11, Pt. 1, Dec. 7, 2004, p. 283A, XP009081642, ISSN: 0006-4971.
Nishio, Mitsufumi et al., "BAFF Support Survival of Chronic Lymphocytic Leukemia B Cells by a Pathway Independent of Stromal Derived Factor-1 Alpha", Blood, W.B. Saunders Company, Orlando, FL., vol. 104, No. 11, Pt. 1, Nov. 16, 2004, p. 528A, XP009081641, ISSN: 0006-4971.
Gorelik, Leonid et al., "BAFF Controls B-Cell Function by Regulation of OBF-1 and B Cell Receptor Expression", Journal of Immunology, Williams & Wilkins Co., vol. 176, No. Suppl S, May 16, 2006, p. S20, XP009081651, ISSN: 0022-1767.
International Search Report dated Aug. 8, 2007, International Application No. PCT/US2006/039803.
International Preliminary Report on Patentability dated Apr. 24, 2008, International Application No. PCT/US2006/039803.

* cited by examiner

*Primary Examiner* — Ruixiang Li
(74) *Attorney, Agent, or Firm* — Finnegan, Henderson, Farabow, Garrett & Dunner, LLP

(57) ABSTRACT

BAFF plays a central role in acquired immunity. The disclosure identifies BAFF-responsive genes that are substantially upregulated by administration of BAFF and substantially downregulated by treatment with a BAFF antagonist. Specific genes are: NF-κB2, CD23, H2-Mβ (the beta chain of H2-DM), Fig-1, and OBF-1. The disclosure provides methods and compositions for: monitoring the activity of a BAFF antagonist in a mammal; monitoring BAFF activity in a mammal; identifying a mammal to be treated with a BAFF antagonist; and related uses. Such methods include detecting one or more molecules selected from the group consisting of Fig-1 molecule, OBF-1 molecule, and H2-Mβ molecule in a biological sample of the mammal, and optionally further detecting NF-κB2 molecule and/or CD23 molecule in the biological sample.

7 Claims, 5 Drawing Sheets

METHODS FOR USE WITH BAFF ANTAGONISTS

This application claims priority to U.S. Application No. 60/726,406, filed Oct. 13, 2005, which are hereby incorporated by reference.

FIELD OF THE INVENTION

The invention is in the fields of immunology and pharmacology. The invention generally relates to diagnosis and treatment of immunologic disorders and, particularly, disorders that are amendable to treatment with antagonists of BAFF (B cell activating factor of the TNF family).

BACKGROUND OF THE INVENTION

B cells play a central role in acquired immunity. These cells possess the unique ability to mount a rapid and directed antibody response against foreign antigens, and to act as antigen-presenting cells. To maintain B cell homeostasis and a self-tolerant state, it is important to have a continuous pool of B cell precursors that will mature and migrate to peripheral organs, as well as maintain a process of negative selection to eliminate autoreactive B cells. Dysregulation in the B cell developmental process could lead to a block in B cell development, and thus immune deficiency, or conversely, to an escape and expansion of self-reactive B cells leading to autoimmunity.

Generation of high affinity, somatically hypermutated autoantibodies is one of the hallmarks of autoimmune conditions. The autoantibodies can cause severe tissue damage (e.g., as in lupus nephritis) or loss of blood components (e.g., as in immune thrombocytopenia purpura). The prevailing treatment strategies for autoimmune disorders employ global immunosuppressants that have harmful side effects with long-term use.

Recent discovery of the B cell survival and maturation factor BAFF (also known as TALL-1, THANK, BLyS, zTNF4, and TNFSF13B, and sometimes referred to as neutrokine α, NTN2, Kay, MARCH, TL5, TNFL1, and "63954") provided a unique opportunity for developing targeted intervention strategies for autoreactive B cell function. Elucidation of the role of BAFF in acquired immunity has been rapid since its first description as a B cell growth factor. BAFF (SEQ ID NO:30) (Accession No. AAD25356) is described in, e.g., Schneider et al (1999) J. Exp. Med., 189:1697-1710; PCT Publication WO 99/12964 and U.S. patent application Ser. No. 09/911,777 (issued as U.S. Pat. No. 6,869,605); and U.S. Pat. Nos. 6,623,941 and 6,689,579. BAFF has been implicated in costimulation of B cells (Moore et al. (1999) Science, 285:260-263; Schneider et al. (1999) J. Exp. Med., 189:1747-1756; Mukhopadhyay et al. (1999) J. Biol. Chem., 274:15978-15981); increased B cell proliferation (Moore et al. (1999) Science, 285:260-263); and increased survival of normally deleted B cells (Khare et al. (2000) Proc. Natl. Acad. Sci., 97:3370-3375; Gross et al. (2000) Nature, 404:995-999; Mackay et al. (1999) J. Exp. Med., 190:1697-1710). Studies have indicated that higher than normal levels of BAFF may contribute to the pathogenesis of autoimmune diseases, such as systemic lupus erythematosus (SLE) and rheumatoid arthritis. For a review, see, e.g., Mackay et al. (2002) Nature Reviews: Immunology, 2:465475; Kalled et al. (2003) Expert Opin. Ther. Targets, 7(1):115-23.

Three cognate receptors for BAFF have been identified: (1) B cell maturation antigen (BCMA; Accession No. S43486; Gross et al. (2000) Nature, 404:995-999; PCT Publication WO 01/12812; U.S. patent application Ser. No. 10/077,137); transmembrane activator and cyclophilin ligand interactor (TACI; Accession No. AAP57629; Gross et al., supra); and more recently, BAFF-R (also called BR3; Accession No. AF373846; Thompson et al. (2001) Science, 293:2108-2111). BAFF-R is the only one of the three receptors that is specific for BAFF (Thompson et al., supra). BCMA and TACI bind not only to BAFF but also to another TNF family ligand, APRIL (Yu et al. (2000) Nat. Immunol., 1:252-256; Wu et al. (2000) J. Biol. Chem., 275:35478-35485; Rennert et al. (2000) J. Exp. Med., 192:1677-1684; PCT Publication WO 01/24811; U.S. patent application Ser. No. 10/115,192).

Soluble forms of BAFF receptors have been made by fusing their extracellular domains to the Fc portion of immunoglobulin. Treatment of normal mice with such a soluble form of TACI or BCMA (TACI-Fc or BCMA-Fc) leads to reduced B cell numbers and a lack of humoral response (Shu et al. (1999) J. Leukoc. Biol., 65:680-683; Yan et al. (2000) Nat. Immunol., 1:37-41; Xia et al. (2000) J. Exp. Med., 192:137-143; Wang et al. (2001) Nat. Immunol., 2:632-637; Yu et al. (2000) Nat. Immunol., 1:252-256). For example, in a mouse model for rheumatoid arthritis, an autoimmune disease that involves both B and T cell components, TACI-Fc substantially inhibits inflammation and slows disease progression (Wang et al. (2001) Nat. Immunol., 2(7):632-637). These effects are thought to be attributed to BAFF sequestration because BAFF-deficient mice have a phenotype similar to that of TACI-Fc- or BCMA-Fc-treated mice (almost complete loss of mature B cells and a severely compromised humoral response) (Schiemann et al. (2001) Science, 293:2111-2114; Gross et al. (2001) Immunity, 15:289-302). More recently, BAFF-specific agents, including BAFF-R-Fc and BAFF antibodies, have been developed for treatment of autoimmune and other disorders (see, e.g., U.S. patent application Ser. Nos. 09/911,777; 10/380,703; 10/045,574; and 60/458,707); Kalled et al. (2003) Expert Opin. Ther. Targets, 7(1):115-23).

Thus, while therapeutic strategies employing BAFF-specific agents already exist, and new drugs targeting the BAFF signaling pathway are being developed, there is a need to provide methods for evaluating and monitoring efficacy of such agents, for selecting optimal responders to such treatments, and for providing improved dosing/timing regimens for those therapeutics.

SUMMARY OF THE INVENTION

The present invention is based, at least in part, on the identification of genes that are regulated by BAFF. In the experiments conducted in connection with the invention, DNA microarray chips were used to compare gene expression profiles of splenic cells obtained from BAFF-deficient and wildtype mice which were treated with soluble BAFF and BAFF-R Fc fusion protein (BAFF-R:Fc), respectively. A number of BAFF-responsive genes were identified (see Table 2). Five of these genes were substantially upregulated in the BAFF-treated mice while being substantially downregulated in the BAFF-R:Fc-treated mice. The five genes are: NF-κB2, CD23, H2-Mβ2 (a beta chain of H2-DM), Fig-1, and OBF-1. Although the expression of cell surface CD23 and activation of NF-κB2 have been previously reported to be regulated by BAFF, the transcriptional regulation of all five genes, as well as BAFF regulation of H2-Mβ2, Fig-1, and OBF-1 at the protein level, have not been reported previously.

Accordingly, the invention provides methods, compositions and kits for monitoring the activity of a BAFF antagonist in a mammal; monitoring BAFF activity in a mammal; identifying a mammal to be treated with a BAFF antagonist;

treating and preventing disorders, including optimizing amounts and scheduling of administration or readministration of therapeutics such as BAFF antagonists, as well as related uses.

In one aspect, the invention provides a method for monitoring efficacy of a BAFF antagonist in a mammal. In some embodiments, the method includes the steps of administering the BAFF antagonist to the mammal and detecting one or more molecules selected from the group consisting of Fig-1 molecule, OBF-1 molecule, and H2-Mβ molecule in a biological sample of the treated mammal, wherein the level of expression, relative to a control, of at least one of the detected molecules indicates efficacy of the BAFF antagonist in the mammal. In other embodiments, the methods includes the steps of administering the BAFF antagonist to the mammal and detecting at the transcriptional level one or both molecules selected from the group consisting of NF-κB2 molecule and CD23 molecule in a biological sample of the treated mammal, wherein the level of expression, relative to a control, of at least one of the detected molecules indicates efficacy of the BAFF antagonist in the mammal.

In another aspect, the invention provides a method for monitoring BAFF activity in a mammal. In some embodiments, the method includes the step of detecting in a biological sample of the mammal one or more molecules selected from the group consisting of H2-Mβ molecule, Fig-1 molecule, OBF-1 molecule, wherein elevated expression, relative to a control, of at least one of the detected molecules indicates elevated BAFF activity in the mammal. In other embodiments, the method includes the step of detecting at the transcriptional level in a biological sample of the mammal one or both molecules selected from the group consisting of NF-κB2 molecule and CD23 molecule, wherein elevated expression, relative to a control, of at least one of the detected molecules indicates elevated BAFF activity in the mammal.

In yet another aspect, the invention provides a method of identifying a mammal to be treated with a BAFF antagonist. In some embodiments, the method includes the steps of providing a biological sample from a mammal and detecting one or more molecules selected from the group consisting of Fig-1 molecule, OBF-1 molecule, and H2-Mβ molecule in a biological the sample, wherein elevated expression, relative to a control, of at least one of the detected molecules indicates that the mammal should be treated with the BAFF antagonist. In other embodiments, the method includes the steps of providing a biological sample from a mammal and detecting at the transcriptional level in a biological sample of the mammal one or both molecules selected from the group consisting of NF-κB2 molecule and CD23 molecule, wherein elevated expression, relative to a control, of at least one of the detected molecules indicates that the mammal should be treated with the BAFF antagonist.

Each one of the above methods may further include an additional step of detecting, in the biological sample, NF-kB2 molecule, CD23 molecule, and/or another BAFF- and/or BAFF-R-responsive molecule, e.g., as listed in Table 2, at the transcriptional and/or translational level(s). The methods may further comprise detecting BAFF molecule and/or BAFF-R molecule in the sample.

The invention provides methods for treating or preventing an immunologic disorder in a mammal comprising the steps of administering a BAFF antagonist to a mammal in need thereof and detecting a molecule selected from the group consisting of a H2-Mβ molecule, a Fig-1 molecule, and an OBF-1 molecule in a biological sample of the mammal. According to one further embodiment, the mammal is administered another dose of a BAFF antagonist if detection of the molecule indicates that the molecule is elevated relative to a control. According to further embodiments, the steps of detecting a molecule selected from the group consisting of a H2-Mβ molecule, a Fig-1 molecule, and an OBF-1 molecule in a biological sample of the mammal and administering additional doses of a BAFF antagonist if levels of the molecule rise relative to a control are repeated as necessary to treat or prevent the immunologic disorder. According to a further embodiment, the BAFF molecules in the mammal to be treated are detected before, during and/or after treatment with the BAFF antagonist to monitor BAFF molecule levels. According to one embodiment, the mammal having the immunologic disorder has elevated BAFF molecule levels relative to a control.

According to one embodiment the immunologic disorder is selected from the group consisting of an autoimmune disorder, a hyperproliferative immune disorder, such as B cell neoplasias and B cell hyperplasias, an antibody-mediated pathology and transplant rejection. According to another embodiment, autoimmune disorder is selected from the group consisting of autoimmune rheumatologic disorders, autoimmune gastrointestinal and liver disorders, vasculitis, autoimmune neurological disorders, autoimmune dermatologic disorders, autoimmune endocrine disorders, autoimmune thyroid disease, autoimmune renal disorders, and autoimmune hematologic disorders. According to a further embodiment, the immunologic disorder is selected from the group consisting of rheumatoid arthritis, asthma, psoriasis, psoriatic arthritis, inflammatory bowel disease including ulcerative colitis and Crohn's Disease, pemphigus vulgaris, ANCA-associated vasculitis, lupus including lupus nephritis and systemic lupus erythematosus (SLE), multiple sclerosis, Sjogren's syndrome, Graves' disease, insulin-dependent diabetes melitis (IDDM), type I diabetes, pernicious anemia, thyroiditis, glomerulonephritis, rejection, B cell hyperproliferative disorders, Wegener's granulomatosis, transplant rejection, graft-versus-host disease (GVHD), idiopathic thrombocytopenic purpura (ITP) and myasthenia gravis.

According to another embodiment, the hyperproliferative immune disorder is selected from the group consisting of non-Hodgkin's lymphoma (NHL), chronic lymphocytic leukemia (CLL), acute lymphocytic leukemia (ALL), mantle cell lymphoma, marginal zone related tumors, follicular lymphoma (FL), large cell lymphoma such as diffuse large B-cell lymphoma, Burkitt's lymphoma, plasma cell disorders such as multiple myeloma.

In one embodiment, the BAFF antagonist is selected from the group consisting of an anti-BAFF antibody, an antibody against one or more BAFF receptors, a dominant negative BAFF, a soluble BAFF receptor (e.g., BAFF-R, BCMA, and TACI) and other proteins that bind BAFF or BAFF receptors and inhibit BAFF signaling (e.g., immunoadhesions comprising BAFF-binding polypeptides or BAFF receptor-binding polypeptides fused to the Fc region of an IgG). According to another embodiment, the BAFF antagonist inhibits the interaction between BAFF and a BAFF receptor. According to a further embodiment, the BAFF antagonist inhibits the interaction between BAFF and BAFF-R. According to one embodiment, the BAFF antagonist is selected from the group consisting of BCMA-Fc, BAFF-R-Fc, TACI-Ig, belimumab, an anti-BAFF-R antibody, a BAFF-binding peptibody and a dominant negative BAFF.

Diagnostic/monitoring methods and kits for patients treated or to be treated for an immunological disorder and/or for identifying patients treated or to be treated with a BAFF antagonist are also provided. In some embodiments, a kit comprises reagents for detecting at the transcription of one or both molecules selected from the group consisting of NF-κB2 molecule and CD23 molecule. In another embodiment, a kit comprises reagents for detecting one or more molecules selected from the group consisting of H2-Mβ molecule, Fig-1 molecule, and OBF-1 molecule. A kit for patients to be treated for an immunological disorder comprising reagents for detecting at the transcription of one or both molecules selected from the group consisting of NF-κB2 molecule and CD23 molecule. The kits may further comprise a reagent for detecting a BAFF molecule, printed material having information for monitoring the efficacy of treatment of a mammal with a BAFF antagonist, and/or instructions for detecting a BAFF molecule.

Additional aspects of the invention will be set forth in part in the following description, and in part will be understood from the description, or may be learned by practice of the invention. The foregoing general description and the following detailed description are exemplary and explanatory only and are not restrictive of the invention as claimed.

BRIEF DESCRIPTION OF THE FIGURES

FIG. 2A—Single cell suspensions were prepared from spleens from C57BL/6 mice injected i.p. with BAFF-R:Fc (or normal IgG) 2 or 7 days prior to staining, or from BAFF-deficient mice i.p. injected with soluble BAFF (or PBS) 2 days prior to staining. Intracellular staining of CD19$^+$ B cells for H2-DM was performed. Mean fluorescent intensity (MFI) of the staining is shown for groups of 3 mice. Error bars show standard deviations. All treatment groups are different from the appropriate controls with the $p<0.03$. FIG. 2B—Single cell suspensions were prepared from spleens taken from C57BL/6 mice injected i.p. with BAFF-R:Fc either 2 or 7 days earlier. Splenocytes from C57BL/6 mice injected i.p. with normal human IgG 7 days prior were used as a control. Cells were stained with antibodies to B220 and MHC class II. MHC class II expression is shown after gating on B220$^+$ cells. An isotype control antibody was used to assess the background staining (shaded profile).

BRIEF DESCRIPTION OF THE SEQUENCES

TABLE 1

Figure 1:
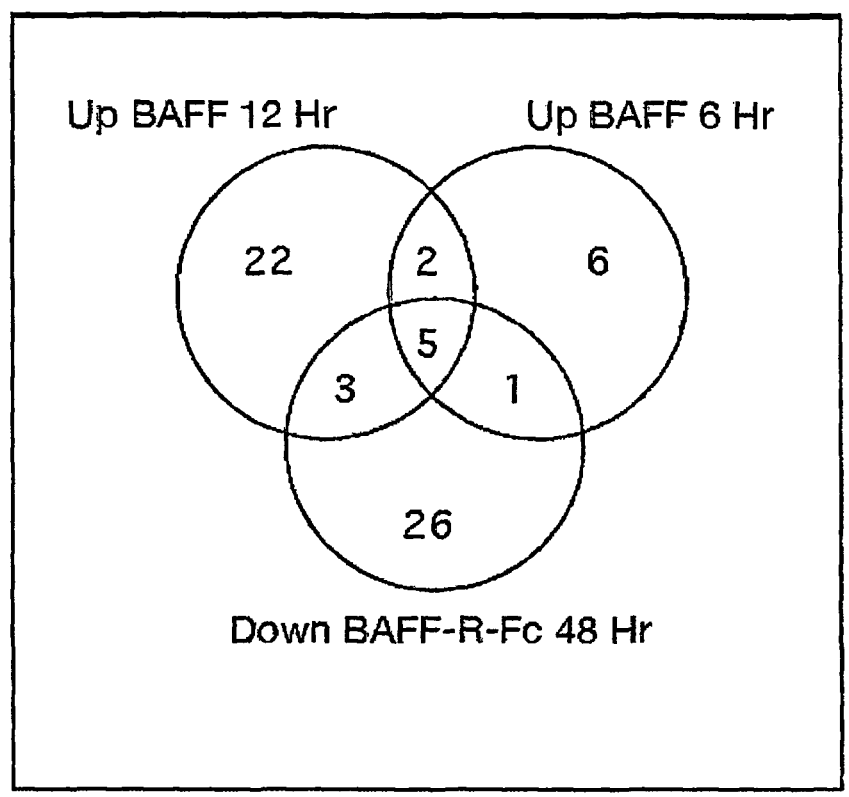
FIG. 1. Identification of BAFF-regulated genes. cDNA was generated from splenic RNA of BAFF-deficient mice 6 hours or 12 hours post i.p. treatment with soluble BAFF and from C57BL/6 mice 2 days after i.p. treatment with BAFF-R:Fc. The cDNA was analyzed on the Affymetrix chip U74Av2. A total of 14, 32, and 35 distinct genes, each with a significant change ($p \leq 0.05$), were identified in the 6 and 12 hr BAFF treated, and the BAFF-R:Fc treated, mice, respectively. Among these, 5 genes were upregulated in BAFF treated, and concomitantly down-regulated in the BAFF-R:Fc treated, mice.

| | SEQ ID NOs: 1-20 | | | |
|---|---|---|---|---|
| | Nucleic acid sequence | | Amino acid sequence | |
| Gene | Murine | Human | Murine | Human |
| OBF-1 | SEQ ID NO: 1 | SEQ ID NO: 6 | SEQ ID NO: 11 | SEQ ID NO: 16 |
| H2-Mβ* | SEQ ID NO: 2 | SEQ ID NO: 7 | SEQ ID NO: 12 | SEQ ID NO: 17 |
| FIG. 1 | SEQ ID NO: 3 | SEQ ID NO: 8 | SEQ ID NO: 13 | SEQ ID NO: 18 |
| NF-κB2 | SEQ ID NO: 4 | SEQ ID NO: 9 | SEQ ID NO: 14 | SEQ ID NO: 19 |
| CD23 | SEQ ID NO: 5 | SEQ ID NO: 10 | SEQ ID NO: 15 | SEQ ID NO: 20 |

*The murine orthologue is referred to as "H2-Mβ2"; the human orthologue is referred to as "HLA-DMB";, H2-Mβ refers to H2-Mβ2, HLA-DMB, or an orthologue from another species.

SEQ ID NO:21 is an amino acid sequence of human BAFF-R (GenBank™ Accession No. AF373846). Special features noted in the Sequence Listing for this sequence: residue 1—none or any amino acid; residue 2—methionine, none, or any amino acid; residue 21—valine (wild type), asparagine, or another amino acid; residue 28—leucine (wild type), proline, or another amino acid; residue 47—none, any amino acid, or alanine.

SEQ ID NO:22 is an amino acid sequence of human BAFF-R-Fc fusion protein, which includes a signal sequence (amino acids 1-22) and a human IgG1 Fc portion (amino acids 95-321). Special features noted in the Sequence Listing for this sequence: residue 41—valine (wild type), asparagine, or another amino acid; residue 48—leucine (wild type), proline, or another amino acid; residue 67—none, any amino acid, or alanine.

SEQ ID NO:23 is an amino acid sequence of murine BAFF-R (GenBank™ Accession No. Q96RJ3).

SEQ ID NO:24 is an amino acid sequence of murine BAFF-R-Fc fusion protein, which includes a signal sequence (amino acids 1-22) and a murine IgG1 Fc portion (amino acids 88-316).

SEQ ID NO:25 is an amino acid sequence of a BAFF-binding peptide derived from BAFF-R.

SEQ ID NO:26 is an amino acid sequence of one embodiment of human BAFF-R-Fc fusion protein, which includes no signal sequence and a truncated version of the BAFF receptor (amino acids 1-71) and a human IgG1 Fc portion (amino acids 73-298). Special features noted in the Sequence Listing for this sequence: residues 1-10—none, RRGPRSLRGR, or other amino acids; residues 6-10—none, SLRGR, or other amino acids; residue 21—valine (wild type), asparagine, or another amino acid; residue 26—leucine (wild type), proline, or another amino acid; residue 45—none, any amino acid, or alanine; residue 72 (linker)—none or any amino acid, e.g., valine.

SEQ ID NO:27 is an amino acid sequence of human BCMA.

SEQ ID NO:28 is an amino acid sequence of human TACI.

SEQ ID NO:29 is a (dT)-T7 primer used for Affymetrix™ analysis.

DETAILED DESCRIPTION OF THE INVENTION

In order that the present invention may be more readily understood, certain terms are first defined. Additional definitions are set forth throughout the detailed description.

Definitions

The term "antibody" refers to an immunoglobulin or a part thereof, and encompasses any polypeptide comprising an antigen-binding site regardless of the source, method of production, and other characteristics. The term includes but is not limited to polyclonal, monoclonal, monospecific, polyspecific, non-specific, humanized, single-chain, chimeric, synthetic, recombinant, hybrid, mutated, and CDR-grafted antibodies. The term "antigen-binding domain" refers to the part of an antibody molecule that comprises the area specifically binding to or complementary to a part or all of an antigen. Where an antigen is large, an antibody may only bind to a particular part of the antigen. The "epitope," or "antigenic determinant" is a portion of an antigen molecule that is responsible for specific interactions with the antigen-binding domain of an antibody. An antigen-binding domain may be provided by one or more antibody variable domains (e.g., a so-called Fd antibody fragment consisting of a $V_H$ domain). An antigen-binding domain comprises an antibody light chain variable region ($V_L$) and an antibody heavy chain variable region ($V_H$). The terms "anti-BAFF antibody" and "antibody directed against BAFF" refer to any antibody that specifically binds to at least one epitope of BAFF.

The term "BAFF" refers to B cell-activating factor of the TNF family, characterized by its role as a B cell survival factor. A summary of BAFF's characteristics is provided in Mackay et al. (2002) Nature Reviews: Immunology 2:465-475 and in Gavin et al. (2003) J. Biol. Chem., 278(40):38220-8 and in Kalled et al. (2005) Curr. Dir. Autoimmun., 8:206-242. A "BAFF molecule" refers to a molecule substantially identical to: a BAFF polypeptide or a nucleic acid molecule encoding a BAFF polypeptide. The term "BAFF molecule" also refers to isoforms, amino acid fragments, nonredundant subsequences, analogs, or variants of the BAFF polypeptide and nucleic acids encoding them.

The term "BAFF antagonist" generally refers to any compound that directly down modulates the biological activity of BAFF. A molecule "directly down modulates" the biological activity of BAFF by interacting with a BAFF polypeptide, BAFF gene, a BAFF transcript, or a BAFF receptor. A BAFF antagonist may, for example, bind to and neutralize the activity of BAFF; decrease BAFF expression levels; affect stability of BAFF; affect proteolytic cleavage of the membrane-bound form of BAFF into the soluble form; interfere with the binding of BAFF to one or more receptors; interfere with intracellular signaling of one or more BAFF receptors. BAFF antagonists may be proteinaceous (e.g., antibodies, receptor fusion proteins, peptides, peptibodies, dominant negative BAFF mutants) or non-proteinaceous molecules (e.g., small organic molecules (≤500 Da), siRNA, and aptamers). Methods for assessing neutralizing biological activity of BAFF antagonists include those described in the art. Examples of BAFF antagonists include polypeptides comprising a BAFF-binding portion of a BAFF receptor or a BAFF-binding variant thereof (e.g., WO 01/12812, WO 02/24909, WO 00/40716, WO 03/024991), anti-BAFF antibodies (e.g., WO 03/33658), BAFF-binding peptibodies (e.g., WO 02/092620), anti-BAFF-R antibodies (e.g., WO 02/24909) and BAFF-binding peptides (e.g., WO 02/16412). According to one embodiment, the BAFF antagonist is selected from the group consisting of BCMA-Fc (e.g., WO 01/12812), BAFF-R-Fc (e.g., WO 02/24909), TACI-Ig (e.g., WO 00/40716), an anti-BAFF antibody (e.g, WO 03/33658), an anti-BAFF-R antibody (e.g., WO 02/24909), a BAFF-binding peptibodies (e.g., WO 02/092620), a dominant negative BAFF (e.g., WO 04/081043). According a further embodiment, anti-BAFF antibodies and anti-BAFF receptor antibodies are human, humanized, chimerized or otherwise enhanced for treatment in humans.

The term "BAFF-R" refers to a protein that comprises at least a portion of wild-type or mutant receptor for BAFF, other than BCMA or TACI, that is capable of binding to BAFF. It has been determined that the BAFF-binding domain of human BAFF-R contains amino acids 27 to 32 of SEQ ID NO:21. BAFF-R is further defined in PCT Publication WO 02/24909 and U.S. patent application Ser. Nos. 10/380,703 and 60/458,707, and specifically includes, but is not limited to, human BAFF-R (SEQ ID NO:21; Accession No. AAD25356; amino acid 47 of SEQ ID NO:21 is not present in some isoforms) and murine BAFF-R (SEQ ID NO:23; Accession No. Q96RJ3). The term "BAFF-R" also refers to naturally occurring variants, e.g., the splice variant containing an alanine at amino acid 47 of SEQ ID NO:21 corresponding to amino acid 67 of SEQ ID NO:22, as well as BAFF-binding variants of BAFF-R, e.g., BAFF-R variants having decreased aggregation (e.g, WO 02/24909).

The terms "BAFF-R-Fc" and "BAFF-R-Ig" refer to a fusion protein comprising BAFF-R and antibody constant region sequences, such as, for example, an Fc portion. The terms "anti-BAFF-R antibody" and "antibody directed against BAFF-R" refer to any antibody that specifically binds to at least one epitope of BAFF-R. The term "BAFF-R molecule" refers to a molecule substantially identical to: a BAFF-R polypeptide or a nucleic acid molecule encoding an BAFF-R polypeptide. The term "BAFF-R molecule" also refers to isoforms, fragments, nonredundant subsequences, analogs, and variants of the BAFF-R polypeptide and nucleic acids encoding them.

The term "BAFF-specific antagonist" refers to a compound that: (1) has the ability to counteract the effect(s) of BAFF in vivo or in vitro, e.g., by competitive blockage of BAFF binding to one or more BAFF receptors, and (2) under physiologic conditions preferentially forms a relatively stable complex with BAFF but not with other ligands of the TNF family, such as, e.g., APRIL. Typically, the binding is considered specific when the affinity constant $K_a$ for BAFF is higher than $10^6 M^{-1}$, preferably higher than $10^8 M^{-1}$, while the affinity for another TNF family ligand is lower than $10^6 M^{-1}$, preferably lower than $10^5 M^{-1}$. A skilled artisan recognizes that under certain conditions a low affinity but high avidity binding may also be specific even though $K_a$ of the interaction may be relatively low. In some embodiments, affinity constant $K_a$ of a BAFF-specific antagonist for at least one isoform of BAFF is preferably greater than $10^6 M^{-1}$, $10^7 M^{-1}$, $10^8 M^{-1}$, $10^9 M^{-1}$, $10^{10} M^{-1}$, $10^{11} M^{-1}$, or $10^{12} M^{-1}$. According to one embodiment, the BAFF-specific antagonist is an anti-BAFF antibody (e.g., belimumab and BAFF-binding antibodies described in WO02/02641 and WO 03/55979) or a BAFF-binding peptide-Fc fusion protein (e.g., BAFF-binding fusion proteins described in WO 02/24909).

The term "detecting" and its cognates, when used in reference to the methods of the invention, refers to monitoring a substance from a biological sample relative to a control, qualitatively or quantitatively. In general, the particular technique used for detection is not critical for practice of the invention. For example, "detecting" may include: observing or measuring the amounts of a polypeptide or mRNA in a sample of a mammal, including monitoring a change in the levels of the polypeptide or amount bound to a target; a change in biological function/activity of a TACI, BCMA, BAFF-R, BAFF, and/or APRIL polypeptides (e.g., ligand or receptor binding activity) by using, for example, in vitro intracellular signaling assays (such as NF-κB activation), tumor cell proliferation, B cell proliferation, or survival assays, etc.) and other methods known in the art (e.g., by counting B-cells, observing B-cell markers, etc.). "Detecting" may also include detecting wild type TACI, BCMA, BAFF-R, BAFF, and APRIL levels (e.g., mRNA or polypeptide levels). "Detecting" may also include quantifying a change (increase or decrease) of any value when compared to a control (e.g., percentage change and fold change).

The term "FIG-1" refers to a protein initially described by its induction in B cells upon IL-4 treatment (Proc. Natl. Acad. Sci. U.S.A., 94 (6), 2507-2512 (1997); Biochem. Biophys. Acta, 1576 (1-2), 70-80 (2002)). FIG-1, also known as Interleukin-4 induced gene-1 or Il4i1, has been described as a leukocyte L-amino acid oxidase (Mason et al. (2004) J. Immunol., 173(7):4561-7). Examples of nucleic acid sequences encoding FIG-1 include SEQ ID NO:3 and SEQ ID NO:8. Examples of amino acid sequences of FIG-1 include SEQ ID NO:13 and SEQ ID NO:18. The term "FIG-1 molecule" refers to a molecule substantially identical to: a FIG-1 polypeptide or a nucleic acid molecule encoding a FIG-1 polypeptide. The term "FIG-1 molecule" also refers to isoforms, fragments, nonredundant subsequences, analogs, and variants of the FIG-1 polypeptide and nucleic acids encoding them.

The term "H2-Mβ" refers to a β-chain of a mammalian heterodimeric MHC class II-like molecule, which molecule catalyzes the release of class II-associated invariant chain-derived peptides (CLIP) from newly synthesized class II histocompatibility molecules, freeing the peptide-binding sites for acquisition of antigenic peptides (Alfonso et al. (2000) Annu. Rev. Immunol., 18:113-142). In mice, the H2-Mβ-chain region is duplicated, with H2-Mβ2 being the major form in lymphoid organs (Walter (2001) J. Biol. Chem., 276: 11086-11091). According to one embodiment, "H2-Mβ" refers to the mouse orthologue named H2-Mβ2. According to another embodiment, "H2-Mβ" refers to the human orthologue known as HLA-DMB. Examples of nucleic acid sequences encoding H2-Mβ include SEQ ID NO:2 (murine) and SEQ ID NO:7 (human). Examples of amino acid sequences of H2-Mβ include SEQ ID NO:12 (murine) and SEQ ID NO:17 (human). The term "H2-Mβ molecule" refers to a molecule substantially identical to: a H2-Mβ polypeptide or a nucleic acid molecule encoding a H2-Mβ polypeptide. The term "H2-Mβ molecule" also refers isoforms, fragments, nonredundant subsequences, analogs, and variants of the H2-Mβ polypeptide and nucleic acids encoding them.

The term "CD23" refers to a protein expressed on B cells, follicular dendritic cells, and some T cells (Richards et al. (1991) Crit. Rev. Immunol., 11:65-86). CD23 has been described as a low affinity IgE receptor. Examples of nucleic acid sequences encoding CD23 include SEQ ID NO:5 and SEQ ID NO:10. Examples of amino acid sequences of CD23 include SEQ ID NO:15 (murine) and SEQ ID NO:20 (human). The term "CD23 molecule" refers to a molecule substantially identical to: a CD23 polypeptide or a nucleic acid molecule encoding a CD23 polypeptide. The term "CD23 molecule" also refers to isoforms, fragments, nonredundant subsequences, analogs, and variants of the CD23 polypeptide (e.g., the cleavage product known as p52) and nucleic acids encoding them.

The term "immunologic disorder" refers to disorders and conditions in which an immune response is aberrant. The aberrant response can be due to (a) abnormal proliferation, maturation, survival, differentiation, or function of immune cells such as, for example, T and/or B cells. Examples of immunologic disorders include, but are not limited to, hyperproliferative immune disorders, autoimmune disorders, B cell disorders including plasma cell disorders, B cell lymphoproliferative disorders such as B cell neoplasias and B cell hyperplasias, antibody-mediated pathologies, transplant rejection, and allergies. According to one embodiment, the immunologic disorder is characterized by elevated BAFF levels compared to a control.

Examples of autoimmune diseases include autoimmune rheumatologic disorders (e.g., rheumatoid arthritis, Sjogren's syndrome, scleroderma, lupus such as systemic lupus erythematosus (SLE) and lupus nephritis, polymyositis/dermatomyositis, cryoglobulinemia, anti-phospholipid antibody syndrome, psoriatic arthritis, ankylosing spondylitis), autoimmune gastrointestinal and liver disorders (e.g, inflammatory bowel diseases (e.g., ulcerative colitis and Crohn's disease), autoimmune gastritis and pernicious anemia, autoimmune hepatitis, primary biliary cirrhosis, primary sclerosing cholangitis, celiac disease), vasculitis (ANCA-associated vasculitis, Churg-Strauss vasculitis, Wegener's granulomatosis, and polyarteriitis), autoimmune neurological disorders (e.g, multiple sclerosis, opsoclonus myoclonus syndrome, myasthenia gravis, neuromyelitis optica, Parkinson's disease, Alzheimer's disease, autoimmune polyneuropathies, Guillian-Barre syndrome), autoimmune dermatologic disorders (psoriasis, urticaria, pemphigus vulgaris, bullous pemphigoid, cutaneous lupus erythematosus), autoimmune endocrine disorders (e.g., diabetic-related autoimmune diseases, insulin-dependent diabetes melitis (IDDM), Addison's disease, autoimmune thyroid disease (e.g., Graves' disease, thyroiditis such as Hashimoto's thyroiditis), renal disorders (e.g., glomerulonephritis, Goodpasture's syndrome, Berger's disease), and hematologic disorders (e.g., thrombocytopenic purpura, thrombotic thrombocytopenic purpura, post-transfusion purpura, autoimmune hemolytic anemia).

Examples of hyperproliferative immune disorders include non-Hodgkin's lymphoma (NHL), chronic lymphocytic leukemia (CLL), acute lymphocytic leukemia (ALL), mantle cell lymphoma, marginal zone related tumors, follicular lymphoma (FL), large cell lymphoma such as diffuse large B-cell lymphoma, Burkitt's lymphoma, plasma cell disorders such as multiple myeloma.

Examples of antibody mediated pathologies include ITP, myasthenia gravis, autoimmune hemolytic anemia (erythrocyte autoantibodies), Hashimoto's thyroiditis (thyroid autoantibodies), myasthenia gravis (acetylcholine receptor autoantibodies), Grave's disease characterized by diffuse goiter and hyperthyroidism (thyrotropin receptor autoantibodies) and Goodpasture's syndrome comprising anti-GBM autoantibodies.

Other disorders that can be treated using the compositions and methods of the present invention include but are not limited to disorders described in PCT Publication WO 02/24909 and U.S. patent application Ser. Nos. 09/911,777; 10/380,703; 10/045,574; and 60/458,707.

It should be understood that particular diseases may fall under more than one category described above.

The term "nonredundant subsequence" refers to a subsequence which is unique to the sequence in which it occurs. In some embodiments, a nonredundant subsequence is at least, for example, 10, 15, 20, 30, 40, 50, 70, 100, 200, 300, 400, 500, 1000, or 1500 nucleotides long.

The term "NF-κB2" refers to an intracellular cell signaling polypeptide that can be cleaved to form the p52 subunit of the NF-κB transcription factor. Examples of nucleic acid sequences encoding NF-κB2 include SEQ ID NO:4 (murine) and SEQ ID NO:9 (human). Examples of amino acid sequences of NF-κB2 include SEQ ID NO:14 (murine) and SEQ ID NO:19 (human). The human p52 subunit can be described for example by residues 1-454 of SEQ ID NO:19. The term "NF-κB2 molecule" refers to a molecule substantially identical to: a NF-κB2 polypeptide or a nucleic acid molecule encoding a NF-κB2 polypeptide. The term "NF-κB2 molecule" also refers to isoforms, fragments, nonredundant subsequences, analogs, and variants of the NF-κB2 polypeptide (e.g., the cleavage product known as p52) and nucleic acids encoding them.

The term "OBF-1" refers to a protein that is involved in transcription. OBF-1 can be recruited to octamer binding motifs located at the 3' IgH enhancer. The importance of OBF-1 for the expression of class switched Igs has been described (Kim et al. (1996) Nature, 383: 542-547). Examples of nucleic acid sequences encoding OBF-1 include SEQ ID NO:1 (murine) and SEQ ID NO:6 (human). Examples of amino acid sequences of OBF-1 include SEQ ID NO:11 (murine) and SEQ ID NO:16 (human). The term "OBF-1 molecule" refers to a molecule substantially identical to: an OBF-1 polypeptide or a nucleic acid molecule encoding an OBF-1 polypeptide; as well as isoforms, fragments, nonredundant subsequences, analogs, and variants of the OBF-1 polypeptide and nucleic acids encoding them.

The phrase "substantially identical" means that a relevant amino acid sequence is at least 70%, 75%, 80%, 85%, 90%, 95%, 97%, 98%, 99%, or 100% identical to a given sequence. By way of example, such sequences may be variants derived from various species, or they may be derived from the given sequence by truncation, deletion, amino acid substitution or addition. Percent identity between two amino acid sequences may be determined by standard alignment algorithms such as, for example, Basic Local Alignment Tool (BLAST) described in Altschul et al. (1990) J. Mol. Biol., 215:403-410, the algorithm of Needleman et al. (1970) J. Mol. Biol., 48:444-453, or the algorithm of Meyers et al. (1988) Comput. Appl. Biosci., 4:11-17. Such algorithms are incorporated into the BLASTN, BLASTP, and "BLAST 2 Sequences" programs (see www.ncbi.nlm.nih.gov/BLAST). When utilizing such programs, the default parameters can be used. For example, for nucleotide sequences the following settings can be used for "BLAST 2 Sequences": program BLASTN, reward for match 2, penalty for mismatch −2, open gap and extension gap penalties 5 and 2 respectively, gap x_dropoff 50, expect 10, word size 11, filter ON. For amino acid sequences the following settings can be used for "BLAST 2 Sequences": program BLASTP, matrix BLOSUM62, open gap and extension gap penalties 11 and 1 respectively, gap x_dropoff 50, expect 10, word size 3, filter ON.

METHODS OF THE INVENTION

The present invention is based, at least in part, on the identification of genes that are regulated by BAFF. In the experiments conducted in connection with the invention, DNA microarray chips were used to compare gene expression profiles of splenic cells obtained from BAFF-deficient and wildtype mice which were treated with soluble BAFF and BAFF-R Fc fusion protein (BAFF-R:Fc), respectively. A number of BAFF-responsive genes were identified (see Table 2). Five of these genes were substantially upregulated in the BAFF-treated mice while being substantially downregulated in the BAFF-R:Fc-treated mice. The five genes are: NF-κB2, CD23, H2-Mβ2 (the beta chain of H2-DM), Fig-1, and OBF-1. Although the expression of cell surface CD23 and activation of NF-κB2 have been previously reported to be regulated by BAFF, the transcriptional regulation of all five genes, as well as BAFF regulation of H2-Mβ2, Fig-1, and OBF-1 at the protein level, have not been reported previously.

The invention provides methods and compositions for: monitoring the activity of a BAFF antagonist in a mammal; monitoring BAFF activity in a mammal; identifying a mammal to be treated with a BAFF antagonist; treating diseases and disorders and related uses.

In one aspect, the invention provides a method for monitoring efficacy of a BAFF antagonist in a mammal. In some embodiments, the method includes the steps of administering the BAFF antagonist to the mammal and detecting one or more molecules selected from the group consisting of Fig-1 molecule, OBF-1 molecule, and H2-Mβ molecule in a biological sample of the treated mammal, wherein the level of expression, relative to a control, of at least one of the detected molecules indicates efficacy of the BAFF antagonists in the mammal.

In other embodiments, the methods includes the steps of administering the BAFF antagonist to the mammal and detecting at the transcriptional level one or both molecules selected from the group consisting of NF-κB2 molecule and CD23 molecule in a biological sample of the treated mammal, wherein the level of expression, relative to a control, of at least one of the detected molecules indicates efficacy of the BAFF antagonist in the mammal.

In another aspect, the invention provides a method for monitoring BAFF activity in a mammal. In some embodiments, the method includes the step of detecting in a biological sample of the mammal one or more molecules selected from the group consisting of H2-Mβ molecule, Fig-1 molecule, OBF-1 molecule, wherein elevated expression, relative to a control, of at least one of the detected molecules indicates elevated BAFF activity in the mammal. In other embodiments, the method includes the step of detecting at the transcriptional level in a biological sample of the mammal one or both molecules selected from the group consisting of NF-κB2 molecule and CD23 molecule, wherein elevated expression, relative to a control, of at least one of the detected molecules indicates elevated BAFF activity in the mammal.

In another embodiment, the invention provides a method for monitoring efficacy of a BAFF antagonist in a mammal that includes the steps of:

(a) administering the BAFF antagonist to the mammal and (b) detecting a change in expression level of one or more immunoglobulin chains expressed in the mammal and encoded by a subset of genes responsive to OBF-1. A decrease in the expression level following the administering of the BAFF antagonist indicates that the BAFF antagonist is effective.

In another related embodiment, the invention provides a method of monitoring efficacy of a BAFF antagonist in a mammal comprising:

(a) administering the BAFF antagonist to the mammal and
(b) detecting a change in expression level of one or more immunoglobulin chains expressed in the mammal and encoded by a subset of genes non-responsive to OBF-1. An increase in said expression level following the administering of the BAFF antagonist indicates that the BAFF antagonist is effective.

In the methods for monitoring efficacy of BAFF antagonists involving detection of immunoglobin chains, the antibody chain whose expression level is being detected may be a light chain (e.g., a kappa light chain) and/or a heavy chain (e.g., of the IgG2a or IgG2b isotype). For instance, as shown in the Examples, the kappa chain encoded by a gene responsive to OBF-1 may be encoded by a Vκ gene selected from the group consisting of Vκ2, Vκ4/5, Vκ8, Vκ19/18, and Vκ21, in mouse. OBF-1-responsive genes in other species can be identified using routine methods. As with other methods of the invention, the change in the expression level of an immunoglobulin chain can be detected at the mRNA level or at the protein level. The expression levels can be detected using, e.g., fluorescent cytometry (FACS). In preferred embodiments, the expression levels are assessed using a biological sample derived from the blood of the mammal, however, other types of biological samples can be used.

In yet another aspect, the invention provides a method of identifying a mammal to be treated with a BAFF antagonist. The method includes the steps of providing a sample from a mammal and detecting one or more molecules selected from the group consisting of Fig-1 molecule, OBF-1 molecule, and H2-Mβ molecule in a biological sample of the mammal, wherein elevated expression, relative to a control, of at least one of the detected molecules indicates that the mammal should be treated with the BAFF antagonist. In other embodiments, the method includes the steps of providing a biological sample from a mammal and detecting at the transcriptional level in a biological sample of the mammal one or both molecules selected from the group consisting of NF-κB2 molecule and CD23 molecule, wherein elevated expression, relative to a control, of at least one of the detected molecules indicates that the mammal should be treated with the BAFF antagonist.

Each one of the above methods may further include detecting at the transcriptional and/or translational level(s) in the sample NF-κB2 molecule, CD23 molecule, and/or another BAFF- and/or BAFF-R-responsive molecule, e.g., as listed in Table 2. The methods may further comprise detecting BAFF molecule and/or BAFF-R molecule in the sample.

A mammal could be, for example, a primate (e.g., a human), a rodent (e.g., a rat or a mouse), or a mammal of another species. In each one of the above methods, the mammal may be one that suffers from an immunological disorder (e.g., autoimmune disease including, but not limited to, rheumatoid arthritis, lupus, and Sjogren's disease) and/or a B cell disorder (e.g., a B cell lymphoma or leukemia including, but not limited to, non-Hodgkin's lymphoma (NHL), chronic lymphocytic leukemia (CLL), acute lymphocytic leukemia (ALL), and follicular lymphoma (FL)). In some embodiments, a mammal is one that was treated with a BAFF antagonist, e.g., as described herein. In other embodiment, a mammal is evaluated to be treated with such an antagonist.

A mammal "in need" of treatment can include, but are not limited to, mammals that have immunologic disorders, mammals that have had immunologic disorders, mammals with symptoms of immunologic disorders and have elevated levels of any one of the molecules selected from the group consisting of BAFF molecule, NF-κB2 molecule, CD23 molecule, H2-Mβ molecule, Fig-1 molecule, and OBF-1 molecule.

Examples of biological samples of a mammal include synovial tissue and fluid (e.g., useful for rheumatoid arthritis), tissues (e.g., salivary gland and/or labial tissue (e.g., useful for Sjogren's disease), blood, plasma, peripheral blood monocytes (PBMC), biopsies, saliva, urine, cerebrospinal fluid, milk, excretions, secretions, swabs, fecal samples, aspirates, or imaging of a portion of a mammal, etc.

Diagnostic/monitoring methods and kits for patients treated or to be treated for an immunologic disorder (e.g., autoimmune disease or B cell disorder) or for identifying patients treated or to be treated with a BAFF antagonist or a BAFF-R antagonist. In some embodiments, a kit for patients to be treated for an autoimmune disease or B cell disorder comprises reagents for detecting at the transcriptional and/or translational level(s) the one or more molecules selected from the group consisting of H2-Mβ molecule, Fig-1 molecule, and OBF-1 molecule. In related embodiments, a kit for patients to be treated for an autoimmune disease or B cell disorder comprises reagents for detecting at the transcriptional (and optionally, reagents for detecting at the translational level) one or both molecules selected from the group consisting of NF-κB2 molecule and CD23 molecule. The kits may include detection means, such oligonucleotides, antibodies, and/or other detection agents directed to H2-Mβ molecule, Fig-1 molecule, and/or OBF-1 molecule. Examples of such oligonucleotides include non-redundant subsequences of SEQ ID NO:1, SEQ ID NO:2, SEQ ID NO:3, SEQ ID NO:6, SEQ ID NO:7, and SEQ ID NO:8. Examples of antibodies are mentioned in the Examples section. Further, non-redundant subsequences derived from orthologues of H2-Mβ, Fig-1, and OBF-1, NF-κB2, or CD23 in other species may be used to probe from for the respective molecules in the same or different species. Kits this invention may include printed material having instructions for detecting one or molecule selected from the group consisting of H2-Mβ, Fig-1, OBF-1, or other molecules described herein or instructions reciting a method of this invention.

Expression levels, at the transcriptional (RNA) or at the translational (protein) level, can be determined using conventional methods. Expression levels are usually scaled and/or normalized per total amount of RNA or protein in the sample, which is typically a housekeeping gene such actin or GAPDH. RNA expression or levels may be determined by, e.g., in situ hybridization, quantitative PCR (e.g., TaqMan™ PCR or RT-PCR), Northern blotting, cDNA or oligonucleotide-based microarrays or any other method for determining RNA expression or levels, e.g., as described in Sambrook et al. (eds.) Cloning: A Laboratory Manual, 2nd ed., Cold Spring Harbor Laboratory Press, 1989), or as described in the Examples. Protein expression or levels may be determined, e.g., by using Western blotting, immunohistochemistry (IHC), ELISA, enzymatic activity assays, fluorescence-activated cell sorting (FACS), imaging techniques or any other method for determining protein expression or levels, e.g., as described in Current Protocols in Molecular Biology (Ausubel et al. (eds.) New York: John Wiley and Sons, 1998).

Examples of comparative controls include, e.g., bodily fluid or tissue from normal patients, non-malignant tissue and pre-treatment or post-treatment samples. In one embodiment, BAFF polypeptide levels in sera or spinal fluid from mammals with immunologic disorders are compared to sera or spinal fluid from normal mammals. In another embodiment, BAFF mRNA levels in neoplasia are compared to BAFF mRNA levels from normal human monocytes. In another embodiment, the H2-Mβ molecules, Fig-1 molecules, OBF-1 molecule or any other responsive molecule described herein are compared before and after treatment with the BAFF antagonist.

In the case of detecting nucleic acids according to the methods of the invention, OBF-1 molecule may be as set out in SEQ ID NO:1 or SEQ ID NO:6, or a non-redundant subsequence of either sequence; H2-Mβ molecule may be as set out in SEQ ID NO:2 (H2-Mβ2) or SEQ ID NO:7, or a non-redundant subsequence of either sequence; Fig-1 molecule may be as set out in SEQ ID NO:3 or SEQ ID NO:8, or a non-redundant subsequence of either sequence; OBF-1 molecule may be as set out in SEQ ID NO:11 or SEQ ID NO:16; NF-κB molecule may be as set out in SEQ ID NO:4 or SEQ ID NO:9, or a non-redundant subsequence of either sequence; CD23 molecule may be as set out in SEQ ID NO:5 or SEQ ID NO:10, or a non-redundant subsequence of either sequence.

In the case of detecting proteins according to the methods of the invention, OBF-1 molecule may be as set out in SEQ ID NO:11 or 16; H2-Mβ molecule be as set out in SEQ ID NO:12 (H2-Mβ2) or SEQ ID NO:17; Fig-1 molecule maybe as set out in SEQ ID NO:13 or SEQ ID NO:18; NF-κB molecule may be as set out in SEQ ID NO:14 or SEQ ID NO:19; CD23 molecule may be as set out in SEQ ID NO:15 or SEQ ID NO:20.

The methods of the invention include detecting of sequences substantially identical to sequences specified in Table 1, including othrologues from other species. Such sequences can be found in publicly available databases such as GenBank™.

BAFF Antagonists

BAFF antagonists used in the methods of the present invention, include (but are not limited to) antibodies directed against GAFF, antibodies directed against one or more isoforms of at least one BAFF receptor, soluble forms of BAFF receptors, and dominant negative forms of soluble BAFF (e.g., as described by Steed et al. (2003) Science, 301:1895-1898 and U.S. Patent Appln. Pub. 2004/0170602).

BAFF receptors include BAFF-R, BCMA, and TACI. In some embodiments, the BAFF antagonist is BAFF-specific (e.g., BAFF-R), while in certain other embodiments the BAFF antagonist my also bind TNF family ligands other than BAFF (e.g., BCMA and TACI which also bind to APRIL). In some embodiments, the BAFF antagonist is an antibody that blocks BAFF binding to its receptor. Antibodies directed to BAFF and to BAFF receptors have been previously described. Producing such antibodies is well within the skill of a person skilled in the art (see, e.g., Antibody Engineering, ed. Borrebaeck, 2nd ed., Oxford University Press, 1995). Examples of antibodies for use in the methods of the invention include those described in PCT Publication WO 99/12964 and U.S. patent application Ser. No. 09/911,777), the anti-BAFF antibody LymphoStat-B™ (Human Genome Sciences, Rockville, Md.), the anti-BAFF-R antibody clones 2.1 and 9.1 (WO 02/24909 at p. 96) and human and humanized versions thereof. In further embodiments, the antibody of the invention may specifically bind, besides BAFF or BAFF-R, another protein that is substantially identical to BAFF or BAFF-R, respectively. In yet further embodiments, antibodies are directed against BCMA and/or TACI. Also contemplated for use in humans are humanized forms and derivatives of nonhuman antibodies derived from non-human species, e.g., mouse.

Soluble forms of BAFF receptor fusion proteins may comprise a BAFF-binding domain of BAFF-R, BCMA, and/or TACI. A BAFF-binding domain is located within the extracellular domain (ECD), i.e., the portion of the protein normally present on the exterior of a cell expressing the protein.

In some embodiments, the soluble BAFF-R is a disulfide-linked peptide having the sequence CHWDLLRHWVC (SEQ ID NO:25) (Kayagaki et al. (2002) Immunity, 10:515-524), or a polypeptide comprising this sequence. In yet other embodiments, the soluble BAFF-R is a polypeptide comprising amino acids 27 to 32 or 18 to 43 of SEQ ID NO:21.

In certain embodiments, a soluble form of a BAFF receptor comprises a BAFF-binding domain of a BAFF receptor fused to a constant region of an immunoglobulin, i.e., as in BAFF-R-Fc. In some embodiments, BAFF-R-Fc comprises residues 3 to 73 of SEQ ID NO:21 fused to the Fc portion of IgG. In illustrative embodiments, BAFF-R-Fc comprises SEQ ID NO:26 (human) or SEQ ID NO:24 (murine). In some embodiments, BAFF-R is a human BAFF-R having a C-terminal deletion starting from amino acid 51 of SEQ ID NO:21, which results in an altered O-linked glycosylation pattern (e.g., ΔBAFF-R described in U.S. Patent Application No. 60/458,707). In some embodiments, soluble BAFF-R comprises ΔBAFF-R which lacks at least the sequence of SEQ ID NO:6 (corresponding to amino acids 51-57 of SEQ ID NO:21).

The BAFF-binding domain of BAFF-R comprises amino acids (aa) 8 to aa 50, aa 13 to aa 50, or aa 13 to aa 43, or aa 18 to aa 43 of SEQ ID NO:21. In certain embodiments, the BAFF-binding domain is identical or substantially identical to aa 2 to aa 63 of SEQ ID NO:21 or to aa 2 to aa 62 of SEQ ID NO:23, including sequences that have been truncated or mutated so long as such sequences retain the ability to bind BAFF. In illustrative embodiments, BAFF-R is a murine sequence as set out from aa 2 to aa 66 of SEQ ID NO:23. In other embodiments, BAFF-R comprises at least 20, 25, 30, 35, 40, 45, or 50 contiguous amino acids of SEQ ID NO:21. Additionally, in some embodiments, the BAFF-binding domain of BAFF-R may be mutated as described in WO 02/24909. For example, certain amino acids in the native BAFF-R sequence can substituted with corresponding amino acids from a BAFF-R polypeptide of another species, e.g., the BAFF-R binding domain may comprise the one or more of the following mutations: V21N, P22Q, A23T, L28P, L28A, and L28S (the numbering is per SEQ ID NO:21).

In certain embodiments, the compositions used in the methods of the invention comprise BCMA derivatives such as soluble forms of BCMA or antibodies against BCMA or against BCMA ligands (e.g., APRIL and/or BAFF). For example, BCMA is described in Laabi et al. (1992) EMBO J., 11(11):3897-3904; U.S. Pat. No. 6,475,978; and Accession No. S43486).

In some embodiments, soluble forms of BCMA used in the methods of the invention comprise (a) a first amino acid sequence derived from the ligand-binding domain of BCMA and (b) a second amino acid sequence derived from the constant region of an immunoglobulin. The first amino acid sequence is derived from all or a portion of the BCMA extracellular domain and is capable of binding a BCMA ligand specifically. The amino acid sequence of a ligand-binding domain of human BCMA is set out in SEQ ID NO:27 amino acid 1 to about amino acid 50. In a particular embodiment, the extracellular domain comprises amino acids 8-41 of SEQ ID NO:27.

In certain embodiments, the compositions used in the methods of the invention comprise TACI derivatives such as soluble forms of TACI or antibodies against TACI or against TACI ligands (e.g., APRIL and/or BAFF). For example, TACI is described in von Bulow et al. (1997) Science, 278:138-141; Gross et al. (2000) Nature, 404:995-999; Marsters et al.

(2000) Curr. Biol., 10:785-788; and Yan et al. (2000) Nature Immunol., 1:37-41; U.S. Pat. No. 6,316,222; and Accession No. O14836.

In some embodiments, soluble forms of TACI used in the methods of the invention comprise (a) a first amino acid sequence derived from the ligand-binding sequence of TACI and (b) a second amino acid sequence derived from the constant region of an immunoglobulin. The first amino acid sequence is derived from all or a portion of the TACI extracellular domain or a ligand-binding variant of TACI and is capable of binding a TACI ligand specifically. An example of a ligand-binding domain of human TACI is set out in SEQ ID NO:28 amino acid 1 to about amino acid 166. In a particular embodiment, an extracellular sequence that can bind a TACI ligand is amino acids 1-100 of SEQ ID NO:28.

In certain embodiments, the constant region of an immunoglobulin comprises any one of $C_H1$, $C_H2$, or $C_H3$ constant regions, or the entire Fc portion (that includes $C_H2$, or $C_H3$), with or without a hinge region. In some embodiments, the second amino acid sequence is derived from the Fc portion of an IgG. In related embodiments, the Fc portion is derived from $IgG_1$, $IgG_4$, or another IgG isotype. In illustrative embodiments, the constant region of an immunoglobulin comprises a sequence from aa 95 to aa 321 of SEQ ID NO:23, or aa 88 to aa 316 of SEQ ID NO:24. The second amino acid sequence may comprise the Fc portion of human $IgG_1$, wherein the Fc is modified to minimize the effector function. Such modifications include changing specific amino acid residues that might alter an effector function such as Fc receptor binding (Lund et al. (1991) J. Immun., 147:2657-2662 and Morgan et al. (1995) Immunology, 86:319-324), or changing the species from which the constant region is derived. Immunoglobulins may have mutations in the $C_H2$ region of the heavy chain that reduce effector function, i.e., Fc receptor binding and complement activation. For example, immunoglobulins may have mutations such as those described in U.S. Pat. Nos. 5,624,821 and 5,648,260. In the $IgG_1$ or $IgG_2$ heavy chain, for example, such mutations may be made at amino acid residues corresponding to amino acids 234 and 237 in the full-length sequence of $IgG_1$ or $IgG_2$. Antibodies and immunoglobulin-receptor fusion proteins may also have mutations that stabilize the disulfide bond between the two heavy chains of an immunoglobulin, such as mutations in the hinge region of $IgG_4$, as disclosed in Angal et al. (1993) Mol. Immunol., 30:105-108.

In certain embodiments, a BAFF-binding domain is fused at the C-terminus or the N-terminus, with or without a linker sequence, to the C-terminus or the N-terminus of the constant region of an immunoglobulin. The exact length and sequence of the linker and its orientation relative to the linked sequences may vary. The linker may, for example, comprise one or more Gly-Ser. The linker may be 2, 10, 20, 30, or more amino acid long and is selected based on properties desired such as solubility, length and steric separation, immunogenicity, etc. It will be understood by one of ordinary skill in the art that certain amino acids in a sequence of any protein may be substituted for other amino acids without adversely affecting the activity of the protein. It is thus contemplated that various changes may be made in the amino acid sequences of BAFF receptor of the invention, or DNA sequences encoding therefore, as provided, without appreciable loss of their biological activity or utility.

The use of derivatives and analogs of BAFF receptors are also within the scope of the present invention. The derivatives or analogs should be functionally active, i.e., capable of exhibiting one or more activities associated with a ligand-binding domain of the wild-type BAFF-R. Derivatives or analogs that retain this binding ability, or inhibit biological activity of BAFF can be produced and tested by procedures known in the art and/or as described in the Examples. Methods of producing such derivatives and analogs include recombinant and synthetic methods (see, e.g., Maniatis (1990) Molecular Cloning, A Laboratory Manual, 2nd ed., Cold Spring Harbor Laboratory, Cold Spring Harbor, N.Y., and Bodansky et al. (1995) The Practice of Peptide Synthesis, 2nd ed., Spring Verlag, Berlin, Germany).

The following examples provide illustrative embodiments of the invention. One of skill in the art will recognize the numerous modifications and variations that may be performed without altering the spirit or scope of the present invention. Such modifications and variations are encompassed within the scope of the invention. The examples do not in any way limit the invention.

EXAMPLES

Mice

All studies were performed following guidelines of the Biogen Idec Institutional Animal Care and Use Committee (IACUC) with 8-18 week-old mice housed under specific pathogen free conditions. A TACI-targeting construct was derived from bacterial artificial chromosome containing mouse 129SvJ genomic DNA (Genome Systems, St. Louis, Mo.). Bacterial recombinational cloning was used to insert a tailless human CD2 reporter at the initiating ATG, and a loxP flanked neomycin selection marker. The final construct lacks the first 578 nucleotides of genomic DNA encoding the first 90 residues of TACI. This construct was used to target the TACI locus of E14Tg2a embryonic stem cells, and correctly targeted cells were injected into C57BL/6 (Taconic, Germantown, N.Y.) blastocysts to generate chimeric mice. Germline transmission of the targeted allele was achieved by crossing chimeras to C57BL/6 mice. Generation of BAFF-, BCMA-, and BAFF-R-deficient mice was described previously (Schiemann (2001) Science, 293:2111-2114; Shulga-Morskaya et al. (2004) J. Immunol., 173:2331-2341). Mice deficient in all three BAFF receptors were obtained by crossing single mutant mice. Mutant mice and corresponding controls were of a C57BL/6-129 mixed genetic background, BAFF-deficient mice were backcrossed to C57BL/6 mice for 6 generations.

Treatment of Mice

Recombinant soluble human BAFF and BAFF-R:Fc, each cross-reacting to murine BAFF-R or murine BAFF, respectively, were purified as previously described (Karpusas (2002) J. Mol. Biol., 315: 1145-1154; and Pelletier (2003) J. Biol. Chem., 278:33127-33133). BAFF-deficient mice were analyzed 6, 12, or 48 hours post i.p. injection of 50 μg BAFF (0.5 mg/ml). Wildtype mice were analyzed 2 or 7 days after i.p. injection of 200 μg BAFF-R:Fc (2 mg/ml). PBS or normal human IgG (Jackson Immunoresearch) were used as controls.

Affymetrix™ Gene Analysis

Total RNA prepared from spleen homogenized in TRIzol™ reagent (Invitrogen Life Technologies, Carlsbad, Calif.) was further purified using an RNeasy™ Mini column (QIAGEN, Valencia, Calif.) according to the manufacturer's protocol. Sample labeling, hybridization, and staining were carried out according to the Eukaryotic Target Preparation protocol in the Affymetrix™ Technical Manual (701021 rev 1) for GeneChip™ Expression Analysis (Affymetrix, Santa Clara, Calif.). In brief, 5 μg of purified total RNA was used in a 20 μL first strand reaction with 200 U SuperScript™ II (Invitrogen, Carlsbad, Calif.) and 0.5 μg (dT)-T7 primer (SEQ ID NO:29) first strand buffer (Invitrogen) at 42° C. for 1 hour. Second strand synthesis was carried out by the addition of 40 U E. coli DNA polymerase, 2 U E. coli RNase H, 10 U E. coli DNA ligase in second strand buffer (Invitrogen) followed by incubation at 16° C. for 2 hrs. The second strand synthesis reaction was purified using the GeneChip™ Sample Cleanup Module according to the manufacturer's protocol. The purified cDNA was amplified using a BioArray™ high yield RNA transcription labeling kit (Enzo Life Sciences, Farmingdale, N.Y.) according to the manufacturer's protocol to produce 70-120 µg of biotin-labeled cRNA (complementary RNA). Mouse Genome U74Av2 GeneChip™ probe arrays were pre-hybridized in a GeneChip™ Hybridization Oven 640 (Affymetrix) according to the manufacturer's protocol. 15 µg of labeled cRNA was fragmented in 30 µL fragmentation buffer 100 mM KOAc, 30 mM MgOAc at 95° C. for 35 min. The fragmented labeled cRNA was resuspended in 300 µL 1× hybridization buffer containing 100 mM MES, 1 M [Na$^+$], 20 mM EDTA, 0.01% Tween™ 20, 0.5 mg/mL acetylated BSA, 0.1 mg/mL herring sperm DNA, control oligo B2, and control transcripts bioB 1.5 pM, bioC 5 pM, bioD 25 pM, and cre 100 pM, and hybridized to GeneChip™ probe arrays according to the manufacturer's protocol (Affymetrix). The hybridized GeneChip™ Microarrays were washed and stained using streptavidin-phycoerythrin (Molecular Probes, Eugene, Oreg.) and amplified with biotinylated anti-streptavidin antibody (Vector Laboratories, Burlingame, Calif.; Sigma, St. Louis, Mo.) on GeneChip™ Fluidics Station 400 (Affymetrix) using an antibody amplification protocol. The GeneChip™ probe arrays were scanned using GeneArray™ Scanner (Hewlett Packard, Corvallis, Oreg.). BAFF-regulated gene expression patterns were analyzed using the Resolver™ data analysis tools. After combining the biological replicates (n=3 for each treatment group), fold changes in gene expression between treated and untreated groups were calculated using the ANOVA ratio analysis in Resolver™. A statistically significant difference in gene expression between two different groups was defined by a p value of less than 0.05. Genes with an absolute fold change of 1.5 or higher were selected. All genes were then filtered through a presence/absence test (p<0.1) to ensure they were detectable in at least one of the two sample groups.

Flow Cytometry

Spleens were minced through a nylon mesh (Cell Strainer; BD Falcon, Bedford, Mass.) to obtain single cell suspensions in Dulbecco's modified Eagle's medium (DMEM), 5% fetal calf serum (FCS), and 2 mM L-glutamine. In some experiments, erythrocytes were lysed by incubating them in a lysis buffer (140 mM NH$_4$Cl, 17 mM Tris-HCl, pH 7.65) for 3 min on ice. Cells were surface-stained with combinations of FITC, PE, Cy-Chrome (Cyc), peridinine chlorophyll protein (PerCP), and/or allophycocyanin (APC)-conjugated monoclonal antibodies for 15 min on ice. Staining with biotinylated monoclonal antibodies was followed by a secondary staining with streptavidin-PerCP (BD Pharmingen, San Diego, Calif.). Stained cells were acquired on a FACSCalibur™ (BD Pharmingen) and data were analyzed using FlowJo™ software (TreeStar, Ashland, Oreg.).

For intracellular H2-DM detection, following the staining with labeled antibodies to cell surface antigens, cells were washed in PBS and fixed in a BD Cytofix/Cytoperm solution (BD Pharmingen) for 20 min at room temperature (RT). After washing with BD Perm/Wash buffer (BD Pharmingen), cells were stained for 20 min at RT with an antibody to mouse H2-DM (clone 2E5A or isotype control rat IgG1 antibody; BD Pharmingen) in BD Perm/Wash Buffer (BD Pharmingen), washed, and then stained with anti-rat IgG1 (BD Pharmingen). Monoclonal antibodies to MHCII, B220, IgG2 were purchased from BD Pharmingen.

Cell Sorting

B cells were purified from splenic cell suspensions by negative selection using anti-CD43 magnetic beads (MACS; Miltenyi Biotec, Auburn, Calif.) according to the manufacturer's instructions. B cell purity ranged from ~70% for BAFF-deficient mice to ~97% for wildtype mice.

Western Blot Analysis

Protein extracts were prepared from purified splenic B cells using the Cytoplasmic Extraction Kit (Pierce, Rockport, Ill.) following the manufacturer's protocol. A total of 10 µg of extracted protein was resolved in each lane of a 10-20% SDS-PAGE gel under reducing conditions, blotted onto a nitrocellulose membrane, and probed with rabbit anti-OBF-1 polyclonal antibodies (sc-955, Santa Cruz Biotechnology, Santa Cruz, Calif.), followed by goat-anti-rabbit antibodies conjugated with horse radish peroxidase and developed using SuperSignal West Pico™ Luminol/Enhancer Solution (Pierce). The chemiluminescent images were collected by Fujifilm LAS 1000 and processed using software Fujifilm ImageGuage™ 4.0.

Vκ Repertoire Analysis

Total splenic DNA was used as a template in a two-round PCR approach as previously described (Novobrantseva et al. (1999) J. Exp. Med., 189:75-88). This approach amplifies only the rearranged DNA and, thus, allows analysis of the rearranged Vκ genes in B cells. Briefly, the first round of PCR was performed with a mixture of degenerate primers VK1, VK2 recognizing most Vκ genes at the framework region 3 and JK5E (Novobrantseva, supra) for 30 cycles of 2 min at 94° C., 1 min at 54° C. and 1.5 min at 72° C. The second round was performed using 1 µl of the first round PCR product as a template in a semi-nested approach with VK1, VK2, and JK2 primers (Novobrantseva, supra) for 30 cycles of 2 min at 95° C., 1 min at 60° C., and 1.5 min at 72° C. PCR products were cloned into a plasmid vector and sequenced from a standard vector specific primer. Vκ gene sequences were analyzed for Vκ gene family usage using the DNAPLOT web based program available at <http://www.dnaplot.de>. Only productive VκJκ joints were analyzed.

Example 1

Expression Profiling Analysis of BAFF Regulated Genes

In order to detect changes in gene expression triggered by BAFF or BAFF-R:Fc in pre-existing B cell population rather than in newly generated populations, it was first determined at what time points BAFF or BAFF-R:Fc treatment does not yet affect total splenic B cell counts. Twenty four hours following the administration of BAFF to BAFF-deficient mice, the number of spleen cells increased by approximately 20%. Thus, spleens were harvested at 6 and 12 hours following treatment when no change in the number of spleen cells was yet detected. BAFF-deficient mice treated with PBS were used as controls. Treatment of wildtype mice with BAFF-R: Fc led to a 40% reduction in B cell number at 3 days, while at 2 days, there was less than a 10% reduction (data not shown). Thus, transcripts were analyzed 2 days following BAFF-R:Fc treatment. Wildtype mice treated with normal human IgG were used as controls.

Using the Affymetrix 12k GeneChip™ Microarray, 65 genes were found to be transcriptionally regulated with a minimum of a 1.5-fold change and p≤0.05 compared to the control samples (FIG. 1 and Table 2). Among these genes, 14 were upregulated at 6 hours following BAFF treatment; 32 were upregulated at 12 hours after BAFF treatment; 35 were then downregulated 2 days after BAFF-R:Fc treatment. Among the genes upregulated at 6 hours after BAFF treatment, 7 remained up-regulated at 12 hours after the treatment (FIG. 1 and Table 2). Furthermore, at the 12-hour time point, 5 of the 7 genes were downregulated in wildtype mice 2 days following treatment with BAFF-R:Fc (Table 2). B cells have been previously reported to express all of these 5 genes, with NF-κB2 and CD23 reported to be regulated by BAFF stimulation (Claudio et al. (2002) Nat. Immunol., 3: 958-965; Gorelik et al. (2004) J. Immunol., 172:762-766; Kayagaki et al. (2002) Immunity, 17:515-524; and Mackay et al. (1999) J. Exp. Med., 190:1697-1710). H2-Mβ, Fig-1, and OBF-1, on the other hand, have not been previously reported as responsive to BAFF.

There was no detectable increase in transcription levels of anti-apoptotic molecules bcl-2, bcl-xL, blk, and A1 previously implicated as mediators of the pro-survival effect of BAFF (Amanna et al. (2001) J. Immunol., 167:6069-6072; Do et al. (2000) J. Exp. Med., 192:953-964; Hatada et al. (2003) J. Immunol., 171: 761-768). Other studies (Lesley et al. (2004) Immunity, 20: 441-453; Zarnegar et al. (2004) Proc. Natl. Acad. Sci. USA, 101:8108-8113) also did not detect any changes in these genes after BAFF treatment suggesting that either these genes do not mediate BAFF's survival effects or that they are regulated at a post-transcriptional level. Alternatively, these results can be explained by differences in experimental systems.

Example 2

BAFF Regulates NF-κB2 Transcription

Mice deficient in NF-κB2 molecule are phenotypically similar to BAFF-deficient animals. Specifically, both types of mice exhibit a strong reduction in the number of mature B-cells demonstrating that NF-κB2 activation by BAFF plays a critical role in B cell survival. Nonetheless, more careful examination showed that as compared to wildtype mice, BAFF-deficient mice and NF-κB2-deficient mice have about 20% and 50% of total B cell numbers, respectively, indicating that some of BAFF-mediated pro-survival signal is independent of NF-κB2. Furthermore, while BAFF-deficient mice display more than 10-fold reduction in basal levels of immunoglobulin, NF-κB2-deficient mice have normal serum Ig levels (Caamano et al. (1998) J. Exp. Med., 187:185-196; Franzoso et al. (1998) J. Exp. Med., 7:47-159; and Schiemann et al. (2001) Science, 293:2111-2114). Similarly, the ability to mount an antigen-specific antibody response was severely compromised in BAFF-deficient, but not NF-κB2-deficient, mice (Caamano, supra; Franzoso, supra; and Schiemann, supra) indicating that BAFF mediates its effect on antibody production through a NF-κB2 independent pathway.

It has been reported that BAFF activation of NF-κB2 requires both BAFF-R and NIK, but not the NF-κB essential modulator (NEMO) (Claudio et al. (2002) Nat. Immunol., 3:958-965; and Kayagaki et al. (2002) Immunity, 17:515-524). This non-canonical NF-κB2 pathway is required for B cell survival and maturation and its activation by BAFF is mediated through BAFF-R, but not TACI or BCMA (Claudio, supra). Table 2 shows that 6 hours after BAFF treatment the transcription of NF-κB2 was upregulated 1.74-fold and remained steadily upregulated (1.62-fold) at 12 hours after the treatment. Conversely, blocking BAFF by BAFF-R:Fc resulted in NF-κB2 being downregulated 1.82-fold at 2 days (Table 2). Thus, transcription of NF-κB2 is closely regulated by BAFF. Together with previous reports (Claudio, supra; and Kayagaki, supra), the transcript profiling results shown in Table 2 indicates that BAFF regulates not only the post-translational processing of p100 to p52 but also the de novo synthesis of the p100 transcript.

Example 3

BAFF Regulates Transcription and Translation of CD23

As recently reported, BAFF induces the CD23 surface expression on B cells from both wildtype and BAFF-deficient mice and that BAFF-R:Fc treatment promptly downregulated its expression shortly after BAFF-R:Fc treatment when no B cell loss was detected (Gorelik et al. (2004) J. Immunol., 172:762-766). However, the response time-line for this gene remained unknown. It is demonstrated here that CD23 transcription is induced as early as 6 hours after BAFF treatment and reduced 2 days after BAFF-R:Fc treatment (Table 2). Therefore, the data suggests that BAFF directly regulates CD23, on both mRNA and protein levels.

Example 4

BAFF Regulates Transcription and Translation of H2-Mβ

Figure 2A:
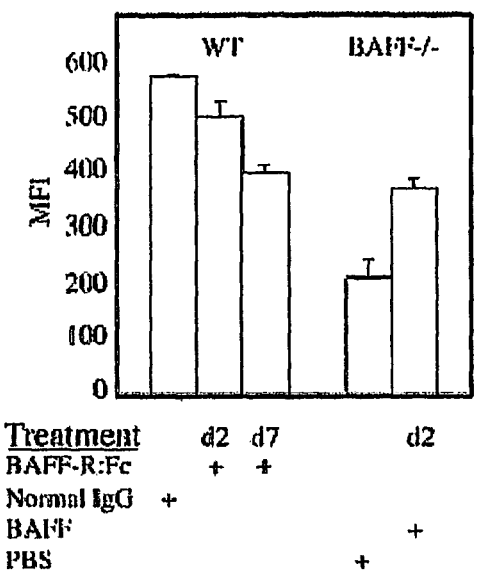
FIGS. 2A and 2B. Regulation of H2-DM and MHC Class II by BAFF signaling.
Figure 2B:
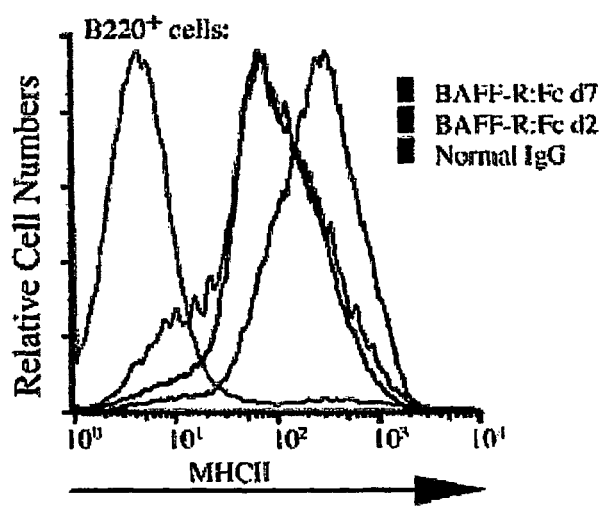

To determine if transcriptional regulation of H2-Mβ induced by BAFF leads to changes in the expression of H2-DM protein, splenic B cells were isolated from wildtype mice at 2 or 7 days following treatment with BAFF-R:Fc, or at 2 days from BAFF-deficient mice treated with soluble BAFF, and stained to detect the intracellular level of H2-DM. FIG. 2A shows that BAFF-R:Fc treatment led to an approximately 15% decrease in H2-DM expression at 2 days and a 30% decrease at 7 days. Conversely, BAFF-treatment resulted in a 70% increase in H2-DM expression. Interestingly, level of H2-DM expression in B cells from BAFF-deficient mice was much lower than in wildtype mice (FIG. 2A) suggesting that H2-DM expression is tightly regulated by BAFF-mediated signals. Although it is not clear if the regulation of H2-DM directly impacts cell surface MHC class II expression levels, a previous report showed that an elevated systemic level of BAFF can lead to increased MHC Class II expression on the surface of B cells (Mackay et al. (1999) J. Exp. Med., 190:1697-1710). Consistent with this observation, the data presented here shows that splenic B cells from wildtype mice treated with BAFF-R:Fc have reduced cell surface MHC Class II expression levels (FIG. 2B). Therefore, BAFF upregulates intracellular H2-DM in addition to cell surface MHC Class II molecules.

TABLE 2

| Primary Sequence Name | Sequence Description | BAFF (6 hrs) | BAFF (12 hrs) | BAFF-R: Fc |
|---|---|---|---|---|
| 96214 | mRNA for erythroid differentiation regulator, partial | + | | |
| 100362_f_at | germline immunoglobulin V(H)II gene H8 | | + | |

TABLE 2-continued

| Primary Sequence Name | Sequence Description | BAFF (6 hrs) | BAFF (12 hrs) | BAFF-R: Fc |
|---|---|---|---|---|
| 100376_f_at | clone BHS2.19 immunoglobulin heavy chain variable region precursor gene, partial cds | | + | |
| 100682_f_at | immunoglobulin heavy and light chain variable region mRNA, complete cds | | + | |
| 100910_at | surfeit locus surfeit 3 gene, exon 8, and surfeit 1 and 2 genes, complete cds | | | + |
| 102154_f_at | Ig active kappa-chain V-region (V139-J1) mRNA from anti-DNP specific hybridoma TF5-139 | | + | |
| 103545_at | 10 days embryo whole body cDNA, RIKEN full-length enriched library, clone: 2610019E17 product: unknown EST, full insert sequence | | | + |
| 103556_at | angiopoietin-like 2 | | | |
| 104078_g_at | ESTs, weakly similar to autoimmunogenic cancer/testis antigen NY-ESO-1 [*H. sapiens*] | | | + |
| 160799_at | Gag . . . env {provirus} [*Mus musculus*, MrV, Evi-2, murine AIDS virus-related provirus, genomic mutant, 3 genes, 4765 nt] | | | + |
| 93657_at | Ets transcription factor Spi-B, partial cds | | | + |
| 93904_f_at | clone N1.1.b immunoglobulin heavy chain VDJ region gene, partial cds | | + | |
| 93927_f_at | clone BPS3.23 germline Ig variable region heavy chain precursor gene, partial cds. | | + | |
| 94290_at | RIKEN cDNA 110012J22 gene | | | + |
| 95313_at | ESTs, highly similar to thrr_mouse thrombin receptor precursor | | | + |
| 96214_at | mRNA for erythroid differentiation regulator, partial | | + | |
| 96538_at | ESTs, moderately similar to y050_human hypothetical protein kiaa0050 [*H. sapiens*] | | | + |
| 96973_f_at | germline immunoglobulin V(H)II gene H18 | | + | |
| 97008_f_at | clone CPS1.13 germline Ig variable region heavy chain precursor pseudogene, partial sequence | | + | |
| 97412_at | RIKEN cDNA 3300001G02 gene | | | + |
| 97563_f_at | immunoglobulin heavy chain gene, CDR3 region, partial cds | | + | |
| 97574_f_at | clone BPS3.19 immunoglobulin heavy chain variable region precursor, gene, partial cds | | + | |
| 97576_f_at | clone BPS5.16 immunoglobulin heavy chain variable region precursor, gene, partial cds | | + | |
| 99159_at | ESTs, highly similar to cypm_rat peptidyl-prolyl cis-trans isomerase, mitochondrial precursor [*R. norvegicus*] | | | + |
| Araf | raf-related oncogene | | | + |
| Blr1 | Burkitt lymphoma receptor 1 | | + | + |
| C4 | complement component 4 (within H-2S) | + | | |
| Cd81 | CD 81 antigen | + | | |
| Cr2 | complement receptor 2 | | | + |
| Csng | casein gamma | | | + |
| Cyp1b1 | cytochrome P450, 1b1, benzaanthracene inducible | | + | |
| D12Wsu28e | DNA segment, Chr 12, Wayne State University 28, expressed | | | + |
| D14Ertd813e | DNA segment, Chr 14, ERATO Doi 813, expressed | | | + |
| D17H6S56E-5 | DNA segment, Chr 17, human D6S56E 5 | + | | |
| D1Lub1 | DNA segment, Chr 1, Lubeck 1 | | | + |
| D2Ertd198e | DNA segment, Chr 2, ERATO Doi 198, expressed | | + | |
| envelope protein | Mouse endogenous murine leukemia virus modified polytropic provirus DNA, complete cds | | + | |
| Fcer2a | Fc receptor, IgE, low affinity II, alpha polypeptide | + | + | + |
| FIG. 1 | interleukin-four induced gene 1 | + | + | + |
| G6pd2 | glucose-6-phosphate dehydrogenase 2 | | | + |
| gag protein | Gag . . . env {provirus} [*Mus musculus*, MrV, Evi-2, murine AIDS virus-related provirus, genomic mutant, 3 genes, 4765 nt] | | | + |
| Gpx3 | glutathione peroxidase 3 | + | | |
| Grpel2 | GrpE-like 2, mitochondrial | | | + |
| H2-DMb2 | histocompatibility 2, class II, locus Mb2 | + | + | + |
| Hey1 | hairy/enhancer-of-split related with YRPW motif 1 | + | | |
| Ier3 | immediate early response 3 | | + | |
| IgG | *Mus domesticus* IgG variable region | | + | |
| Igh | immunoglobulin heavy chain V-DSP2.7-JH2 region (Igh) gene, partial cds | | + | |
| Igh-3 | immunoglobulin heavy chain 3 (serum IgG2b) | + | + | |
| Igk-V20 | immunoglobulin kappa chain variable 20 (V20 family) | | + | + |
| Igk-V28 | immunoglobulin kappa chain variable 28 (V28) | | + | |
| LOC56304 | recombinant antineuraminidase single chain Ig VH and VL domains | | + | |

TABLE 2-continued

| Primary Sequence Name | Sequence Description | BAFF (6 hrs) | BAFF (12 hrs) | BAFF-R: Fc |
|---|---|---|---|---|
| LOC59032 | hypothetical protein from clone MNCb-1932, similar to Homo sapiens FLJ20644 | | | + |
| Ly6d | lymphocyte antigen 6 complex, locus D | | + | + |
| Lyl1 | lymphoblastomic leukemia | | | + |
| MDABG2-4 | mRNA for single chain antibody ScFv, complete cds | | | + |
| Nfkb2 | nuclear factor of kappa light polypeptide gene enhancer in B-cells 2, p49/p100 | + | + | + |
| Pcdh13 | protocadherin 13 | + | | |
| Pou2af1 | POU domain, class 2, associating factor 1 | + | + | + |
| Rnac-pending | RNA cyclase homolog | | | + |
| Tm4sf2 | transmembrane 4 superfamily member 2 | | + | |
| Tnfrsf5 | TNF receptor superfamily member 5 | + | | + |
| VH gene product | immunoglobulin heavy chain variable gene from a transferrin activated hybridoma cell line. | | + | |
| Vh186.2/Jh2 | clone X1AC1701 immunoglobulin heavy chain variable region (Vh186.2/Jh2) mRNA, partial cds | | + | |
| Vpreb3 | pre-B lymphocyte gene 3 | | | + |
| Zfp46 | zinc finger protein 46 | | | + |

Figure 3:
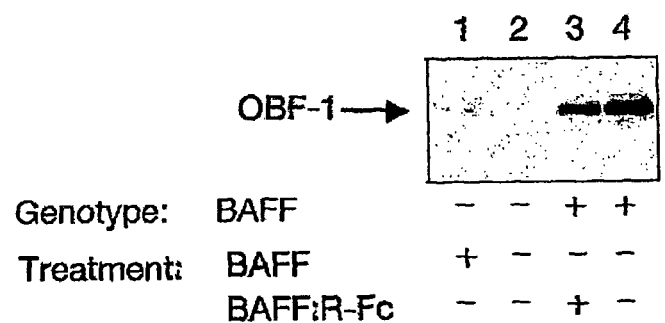
FIG. 3. BAFF-R mediates BAFF-induced OBF-1 protein expression. Cell extracts were prepared from purified splenic B cells isolated from BAFF-deficient mice injected i.p. with BAFF 24 hours and from wildtype mice injected i.p. with BAFF-R:Fc 3 days prior to analysis.

To investigate if BAFF-induced transcription of OBF-1 leads to an increase of this co-activator at the protein level, Western blotting was performed on protein extracts from splenic B cells isolated from BAFF-deficient mice treated with soluble BAFF (24 hours post-treatment) or wildtype mice treated with BAFF-R:Fc (3 days post-treatment). OBF-1 was not detected in B cells from BAFF-deficient mice and only became detectable after BAFF treatment (FIG. 3A, lanes 1 and 2). Conversely, OBF-1 was readily detected in B cells of wildtype mice and was reduced after BAFF-R:Fc treatment (FIG. 3A, lanes 3 and 4). The data shows that BAFF regulates the expression of OBF-1 at both transcriptional and translational levels.

Example 5

BAFF Regulates Class-Switched Immunoglobulin Gene Expression

OBF-1-deficient mice exhibit a drastically reduced level of class switched immunoglobulins (Ig) compared to wildtype mice Casellas et al. (2002) Cell, 110:575-585; Nielsen (1996) Eur. J. Immunol., 26:3214-3218; and Schubart et al. (2001) Nat. Immunol., 2:69-74). Similar deficiency in class switched Igs expression was also observed in BAFF-deficient mice (Schiemann et al. (2001) Science, 293: 2111-2114). The hypothesis was that, by inducing OBF-1 expression, BAFF stimulation of B cells likely leads to elevated levels of class switched Igs. Consistent with this hypothesis, the gene profiling results showed that 16 out of 32 genes up-regulated at 12 hours after BAFF-treatment were IgH genes (Table 2). The increased level of IgH transcripts was not yet apparent at 6 hours after BAFF-treatment when increased expression of OBF-1 was observed. This is consistent with the up-regulation of Ig genes being secondary to up-regulation of OBF-1 induced by BAFF.

Figure 4:
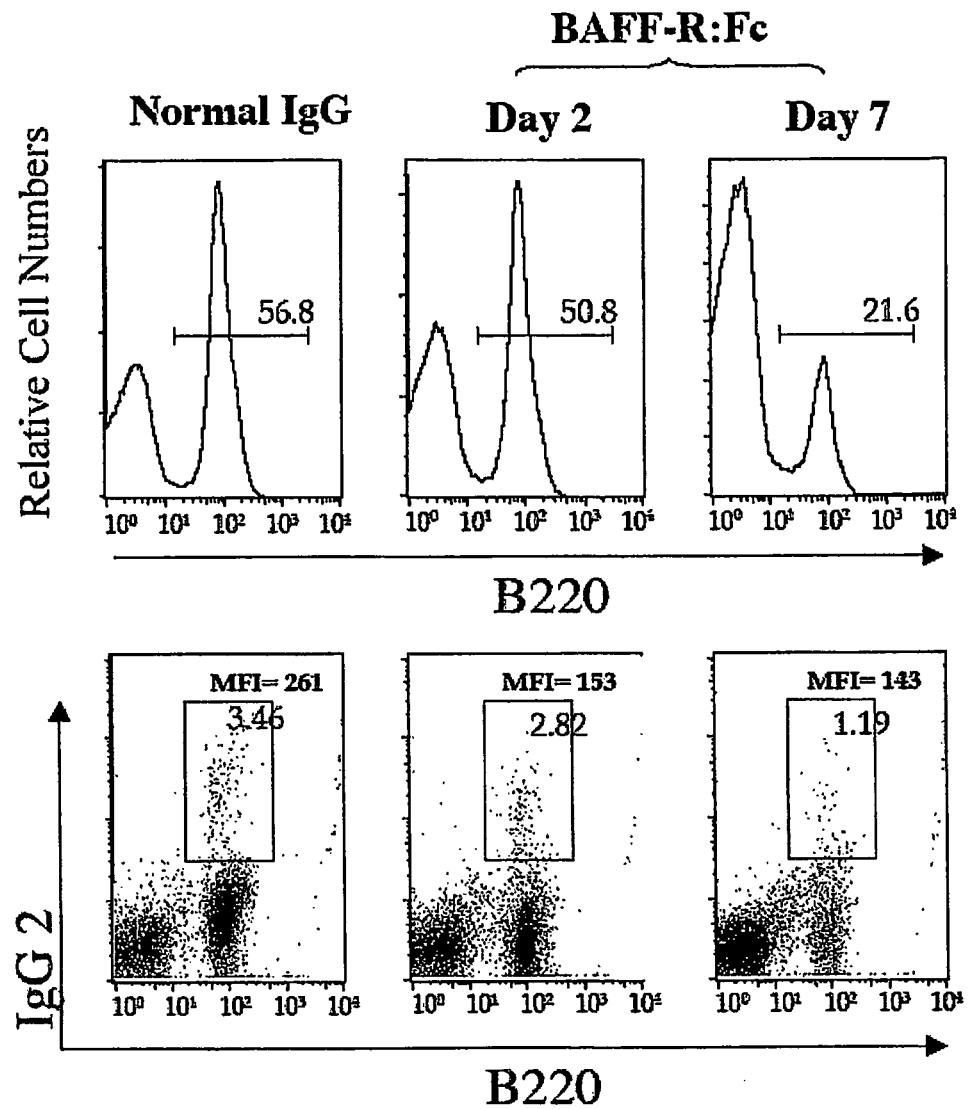
FIG. 4. Cell surface expression of IgG2a/b and survival of IgG2a/b$^+$ B-cells depend on endogenous BAFF signaling. Splenocytes were isolated from C56BL/6 mice injected i.p. with either BAFF-R:Fc 2 or 7 days earlier or from mice treated with normal human IgG 7 days earlier. Cells from the lymphocyte gate are shown. Percent of B220$^+$ cells in the respective population is depicted in the upper panel. The percentage of IgG2a/b$^+$ cells and MFI of IgG2a/b staining on these cells are shown next to IgG2a/b$^+$ B220$^+$ gate in the lower panel.

In order to determine the role of BAFF in the expression of class switched Igs, we examined the expression of IgG2a/b on B cells after BAFF-R:Fc treatment. As judged from the MFI values, BAFF neutralization for as short as 2 days reduced B cell surface IgG2a/b expression by 1.7-fold (FIG. 4) with no apparent loss of B cells in spleen. BAFF-R:Fc treatment for 7 days resulted in a 7-fold reduction in the total number of IgG2a/b[+] B cells (FIG. 4 and data not shown) without further reduction in the surface levels of IgG2a/b on these cells. Thus, BAFF plays an important role in maintenance of normal levels of class switched Igs expression as well as survival of class switched Ig-bearing B cells.

Example 6

Regulation of Igκ Gene Repertoire by BAFF

Figure 5A:
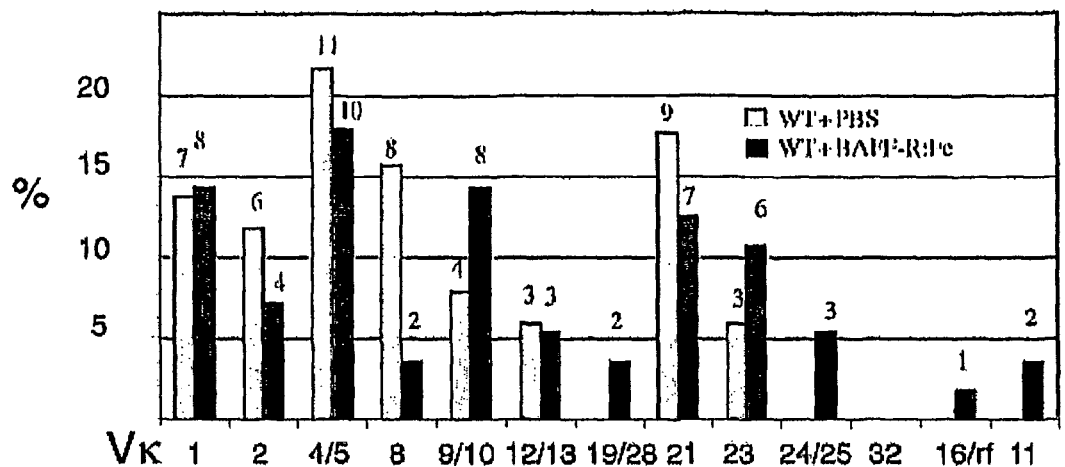
FIGS. 5A and 5B. Skewed Vκ repertoire under BAFF deficient conditions. Vκ family usage (percent of total sequences from each group) in productive joints derived from splenic B cells in C57BL6 mice treated with BAFF-R:Fc or PBS 7 days prior to analysis (FIG. 5A), as well as in BAFF-deficient mice supplemented with BAFF or PBS 2 days prior to analysis (FIG. 5B). Total genomic DNA was prepared from the spleens (pooled from 3 mice per group) of mice treated as indicated and amplified using PCR with mixture of universal VK1, VK2 primers as forward primers in conjunction with a Jκ2 specific primer as a reverse primer. VκJκ amplified products were analyzed to determine productive VκJκ2 rearrangements. The absolute number of sequences obtained for each set is shown above the corresponding bar.
Figure 5B:
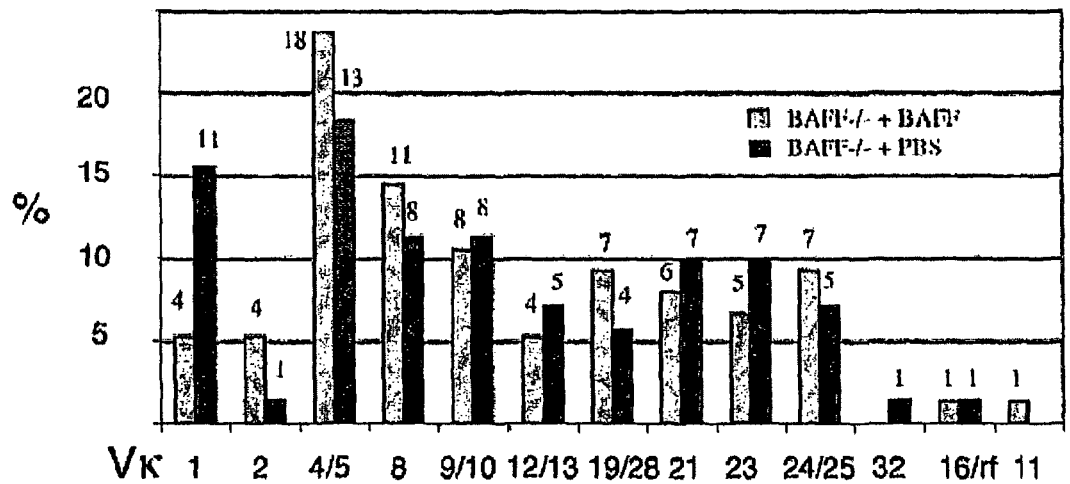

Since OBF-1 also regulates expression of a selected subset of Vκ genes (Casellas et al. (2002) Cell, 110:575-585), we next analyzed changes in Vκ gene repertoires in wildtype mice treated with BAFF-R:Fc or in BAFF-deficient mice treated with BAFF. Here a longer treatment regime than that used in the transcript profiling study was employed as any change in Vκ usage may be secondary to the OBF-1 modulation that occurred earlier. Treatment of wildtype mice with BAFF-R:Fc for 7 days led to the reduced usage of Vκ2, Vκ4/5, Vκ8, and Vκ21 genes (FIG. 5A), and treatment of BAFF-deficient mice with BAFF for 2 days led to the increased usage of Vκ2, Vκ4/5, Vκ8, Vκ19/28 and Vκ24/25 (FIG. 5B). Such non-identical, yet similar, changes in Vκ repertoire are likely due to the fact that BAFF blockade and supplementation will have different effects on different B cell populations. Specifically, BAFF blockade in wildtype mice results in loss of the large mature B cell pool, while BAFF supplementation to BAFF-deficient mice leads to a marked increase in the generation of B cell populations spanning all developmental stages, including B cells carrying Vκ chains that still have not undergone positive or negative selection. Furthermore, changes in the Vκ repertoire caused by BAFF manipulations are similar to those reported for OBF deficient mice (Casellas, supra). The fact that BAFF and OBF-1 have similar effects on the Vκ repertoire strongly suggests that BAFF controls Vκ repertoire selection through regulation of OBF-1 expression.

The embodiments within the specification provide an illustration of embodiments of the invention and should not be construed to limit the scope of the invention. The skilled artisan readily recognizes that many other embodiments are encompassed by the invention. All publications, patents, and sequences from public sequences databases (referred to by their accession numbers) cited in this disclosure are incorporated by reference in their entirety. To the extent the material incorporated by reference contradicts or is inconsistent with this specification, the specification will supersede any such material. The citation of any references herein is not an admission that such references are prior art to the present invention.

SEQUENCE LISTING

<160> NUMBER OF SEQ ID NOS: 29

<210> SEQ ID NO 1
<211> LENGTH: 2578
<212> TYPE: DNA
<213> ORGANISM: Mus musculus

<400> SEQUENCE: 1

| | | | | | | |
|---|---|---|---|---|---|---|
| taaacggtgg | ttccacggga | ggaaagcacg | cccagtcaca | ttaaagaagc | caaactgtct | 60 |
| gcttcaaaga | gaaaaggcaa | catcctgtca | caagccatgc | tctggcaaaa | atccacagct | 120 |
| ccagagcaag | ctcctgcccc | accaaggcca | taccagggtg | ttcgagtcaa | ggagccagtg | 180 |
| aaggagctac | tgagaagaaa | gcgtggccat | accagcgttg | gggcagctgg | gccaccgacc | 240 |
| gcggtggtac | tgccccacca | gcccctggcc | acctacagca | ctgtgggtcc | ttcctgcctt | 300 |
| gacatggagg | tttctgcttc | cacagtgaca | gaggagggaa | cattatgtgc | tggctggctc | 360 |
| tcccaacctg | ccccggccac | tcttcagcca | ttggctccat | ggacacccta | cacggagtat | 420 |
| gtgtcccatg | aagctgtcag | ctgcccctac | tccactgaca | tgtacgtgca | gcctgtgtgc | 480 |
| cccagctaca | cagtggtggg | accctcctcg | gtgttgacct | atgcttctcc | accactcatc | 540 |
| actaatgtca | cgccaagaag | cactgctaca | cccgcggtgg | ggcccagct | ggagggtccc | 600 |
| gagcaccagg | cgcccctcac | ttatttcccg | tggcctcagc | ccctttccac | actgcccacc | 660 |
| tccagcctgc | agtatcaacc | tcctgcccca | acctgtctg | gccccagtt | tgtccagctc | 720 |
| cccatctcta | tcccagagcc | agtccttcag | gacatggatg | accccagaag | ggccatcagc | 780 |
| tccctgacca | ttgacaagct | gcttctggag | gaagaggaaa | gcaacacgta | cgagctcaac | 840 |
| cacaccctct | ccgtggaggg | cttttagggc | tggcttgcat | ctaacagatg | tttcacccat | 900 |
| agctgagatt | ttaaaagtgt | tcaatagagc | ccagacttct | gtttgaagta | gctatttcac | 960 |
| aggcttcctt | tcttcctaaa | gctaaattgt | atcccttctt | tctcccttct | tccttccctc | 1020 |
| gcttccttcc | ttcccccact | gccatcttgc | ttatttctta | tttctccttc | cagttttctt | 1080 |
| cctctggagc | ggcaaatgat | agtgatatta | tgaacaacgc | tttatacgga | atgtcaccaa | 1140 |
| gtctgcagct | cagggttttc | ctttggtggc | acatcattgg | ggaagcaacc | ttctttcagg | 1200 |
| tgcccccgt | ttcctggtag | cagtagcttt | atagatctac | tctatgatac | gttctgcgcc | 1260 |
| ccagttttgt | tttgtgtgct | gttctcagcc | ttggccagat | atactatcta | agtggatgtt | 1320 |
| tctggtctgg | ttacaggggg | atgggacagg | accatcaggg | tgggtaggga | cagtgagtga | 1380 |
| gtgatgggag | acggggctga | ggagcagcag | gacacacatg | tgtgtctgtg | gttagagagg | 1440 |
| gagtgaggag | gggcagggga | aggagtgatc | taacagctct | gaaaaaaat | accactttaa | 1500 |
| tgtggtttag | ctgttcttgt | cagcgattag | gaggaaagct | ggatatggta | tggaggataa | 1560 |
| atgacgagtc | tgcttatttc | tgcctctctg | caggcccgct | aacatgatgc | cagcacttaa | 1620 |
| aatacttctg | tcagcatatt | gccatagcaa | caggaaaaga | aacaggtgaa | gccgatcatt | 1680 |
| gaggaggctt | gcacttagtc | cttccacgtg | ggcttttaat | tcctgttgtg | actcacccag | 1740 |
| ggccatcctg | acgcgttgct | atggattctt | gcgcccactc | accggctgtc | tctggggtcc | 1800 |
| tgaagtcctg | gtcagcaggc | ccactggctt | cattttcagt | tttatcagtt | ttattgcagt | 1860 |
| ttttgctgga | gaagcataac | acttgctgtt | gagtgttttg | ctgtctccta | gtgctttgct | 1920 |
| cctgaagtgg | atgtgtcttt | gggaactggc | ccattgttta | ctaatgatac | catcattaca | 1980 |
| catacacaag | ttttagtctg | tagaatccat | gtagaaccaa | tagatcttct | agaaatgaca | 2040 |

```
gtttctttga tatcccaccc tctttctttc tgcttccaat gaaaacttag agctacctgt    2100
tttttttttc ttcttcttct tctttctttc tctgctttct ctttattttg attcagacat    2160
ctcattatct acctgaagtc ctggtatact tagcttgaat tgttattcc tctttaatat     2220 ttagattaaa tgctagactg aatggtaggt ttacgacttc tgttggtggt taccatgaac    2280
aagaaaggga gagggagcct cagcctattt aattaagacc ttgttgcact aaaacactat    2340
ttaagatttc ccagctactt ggagtttgag gcaatcacag aggagttaac actgggaaaa    2400
caaacaaaac agcaaagaaa gtagtgtgag cggttgctgg gattgaattg gcatcttttt    2460
cgcttcttat cttgagacct cacgtcttgg ctgcaggcat ccaaacagat ttcctccaga    2520
gcctcatttg caacattttc aataaagatt ggttagatga aaaaaaaaaa aaaaaaa       2578
```

<210> SEQ ID NO 2
<211> LENGTH: 1285
<212> TYPE: DNA
<213> ORGANISM: Mus musculus

<400> SEQUENCE: 2

```
ggagttactg ggtacaagtt taggatctca ggaggggctg agtgacttgg cgccacataa    60
gcagcaagga gcaaggggcc tgagcaagag gtaccatatt tacctcagtg tgtgaagatc    120
atttgtccag gctggggcag gagagaacct gaggcccctg caggaggtgc caggggcct     180 ggccttcctg caccttcaga gagtgaaaca tggctgcact ctggctgctg ctgctggtcc    240
tcagtctgga ctgtatgggg gcaggtggct ttgtggctca tgtggaaagc acgtgcgtgc    300
tggatgatgc tgggacccca caggacttca catactgtgt ttccttcaac aaagatctgc    360
tggcctgctg ggatccagat gtgggaaaaa tagtcccctg tgaatttggg gtgctgtatc    420
catgggccga aaattttca aggatcctca acaaagaaga gagccttctc cagcgtttgc     480
aaaacgggct tctggactgt gcctcccaca cccagccctt ctggaatgcg ctgacccaca    540
gaacgagagc gccatctgtc cgagtagccc aaaccacacc ttttaacaca agggagccgg    600
tgatgctggc ctgctacgtc tggggcttct atccagcgga tgtgaccatc acatggatga    660
agaatgggca gcttgtccct tcccacagca acaaggagaa gacggctcag cccaatggag    720
actggacata ccagacagtc tcctacctag ccctaacccc ttcctacggg gacgtctaca    780
cctgcgtggt tcagcacagc gggacctctg agcccatccg aggggactgg acacctgggc    840
tgtcccccat ccagacagtg aaggtctctg tgtctgcagc caccctgggc ctgggcttca    900
tcatcttctg tgttggcttc ttcagatggc gcaagtctca ttcctccagc tacactcctc    960
tctctggatc cacctacccg gaaggacagc attagagagc agaacccgga accaaggaga    1020
ttcagactcc tgaggattcc ttaatgcccc aacatcttca ggacacccca ctttcttgtg    1080
tcatactgcc tctattcagg tccccttcct gaaataaata ttagtagttt ggggggtat     1140 ttataatgaa gtctgtccca ggtggggag ctgaggtgag ctgaaatgag gtgggggttc     1200
aaggcctcct gagagcccct ccttgtcacg agggcaccgt gtcttaggtg atcactaaga    1260
aataaactgg tggacttttg atttc                                          1285
```

<210> SEQ ID NO 3
<211> LENGTH: 2059
<212> TYPE: DNA
<213> ORGANISM: Mus musculus

<400> SEQUENCE: 3

```
gtctgcagtc ctgcccaaga gagctgaaga cagcagctgc cacttgagcc atggctgggc    60
```

-continued

| | |
|---|---|
| tggccctgcg tcttgtcctg gcggccaccc tccttggtct ggcaggctct ctggactgga | 120 |
| aggcagcctc cagcttgaac cctattgaga agtgtatgga ggaccacgat tatgagcagc | 180 |
| tactcaaggt ggtgaccttg ggcctcaatc ggacttcgaa gccccagaag gtggtagtgg | 240 |
| ttggtgcagg cgtggcaggg ctggtagcag ccaagatgct cagtgatgca ggacacaagg | 300 |
| tcaccatcct ggaggcagat aacaggattg ggggccgtat cttcactttc cgggatgaga | 360 |
| agacaggctg gataggggag cttggggcca tgcgaatgcc cagctctcac aggatcttgc | 420 |
| acaagctctg caggaccctg ggcctcaacc tgactcagtt cacacagtat gatgagaaca | 480 |
| cgtggacgga ggtgcataat gtgaagctgc gaaactatgt ggtggagaag atgccagaaa | 540 |
| agctgggcta caacctgaac aacagggaaa ggggccattc cccagaggac atctaccaga | 600 |
| tggcactcaa caaggccttc aaagacctca aggccttggg ctgcaagaaa gccatgaata | 660 |
| agttcaacaa gcatacgctt ctggaatacc tcctcgagga gggcaacctg tcccggccgg | 720 |
| ctgtgcagct cctgggagat gtgatgtccg aggagggctt cttctacctc agctttgcag | 780 |
| aagccttacg tgcgcacgcc tgcctgagcg atagactccg gtacagccgc atcgtaggtg | 840 |
| gctgggacct gcttccgcga gctctgctga gctcactgtc cggggcgctg ctactgaacg | 900 |
| cgcctgtggt gtcgatcact caggggagga acgatgtacg cgtgcacatt gccacctcgc | 960 |
| ttcacagcga gaagacgctg acagccgacg tggtgctgct gactgccagt ggacccgcgc | 1020 |
| tgcagcgcat taccttctcg ccgcccttga ctcgcaagag gcaggaggca ctgcgcgcgc | 1080 |
| ttcactacgt agcagccagc aaggtttttc tgagtttccg tcggcccttc tggcacgagg | 1140 |
| agcacatcga gggcggccac tccaacactg accgccatc gcgcctcata ttctatcccg | 1200 |
| cgcggggcga gggctcactg cttctggcct cctacgcgtg gtcggacgct gcagcccccct | 1260 |
| tcgctggact gagcaccgac cagaccctgc gtttggtgct ccaggacgtg gcggccctgc | 1320 |
| acgggcctgt ggtgttccgg ctgtgggacg gcaggggtgt ggtcaagcgc tgggcagagg | 1380 |
| acccgcatag ccagggaggc ttcgtggtgc agccgccatt gtacgggcgc gaggctgagg | 1440 |
| actatgactg gtcagccccc ttcggccgca tttacttcgc gggcgagcac acagctctcc | 1500 |
| cgcatggctg ggtagagacc gctgtcaagt ccgggttgcg ggccgcggtg agaatcaata | 1560 |
| ataactatgg gtacggggag gtcgaccccc agatgatgga gcatgcatat gcagaggcca | 1620 |
| actatctgga ccagtatcct gaaggggaga ggcccgagga gcagcaggcg cggaagaag | 1680 |
| tcagcccaga tgaacaggag ccctctcaca aacacttgtt ggtggaaacg agccccgagg | 1740 |
| ggcagcaaca cgcgtttgtg gaggccattc ccgagctgca gggacacgtg ttcgtggaga | 1800 |
| ctgtcccccca ggagaagggg cacgcccacc agaatatata tccttcggag catgtacagg | 1860 |
| tgcatgggga agtcatccct gagtggcatg gtcatggggg atctggcacc ccgcaaatgc | 1920 |
| accgagtggg ggaccactcc taatcgcaaa gaggaagtga gcacccagct cctaagccag | 1980 |
| ccctcttcag ggcagacaga ccacctacac taatagccca caataaagtt attttttgtta | 2040 |
| aaccacaaaa aaaaaaaaa | 2059 |

<210> SEQ ID NO 4
<211> LENGTH: 3131
<212> TYPE: DNA
<213> ORGANISM: Mus musculus

<400> SEQUENCE: 4

| | |
|---|---|
| ggaaccagag ccgccaccac ggtgagtggc cgggttcaga tccctgagtg tctagggaat | 60 |
| ggagagggag ggaaggagga ctttagatga caggctgggg ctggacgcca cctccagtga | 120 |

```
gcgcgcacag gaacaggaca ctttgctaca catcagcgac acgcgggcgt ccgaaactct    180
ggaaagctga accggggccc gaagccgcaa gacacagcag ggcctagccc agagatatgg    240
acaattgcta cgatccaggc ctggatggca tccccgaata tgatgatttt gaattcagcc    300
cctccatcgt ggagcctaag gatccagccc ctgagacagc tgatggcccc tatctggtga    360
ttgtggaaca gcccaaacag cgaggcttca gatttcgata tggctgtgaa ggcccctccc    420
atggaggttt gccaggtgcc tccagtgaga agggccggaa gacctatcct actgtcaaga    480
tctgtaacta tgagggaccg gccaagattg aggtggacct ggtgacacac agtgacccac    540
ctcgtgcgca tgcccacagt ctggtgggca agcagtgttc agagttggga gtgtgcgctg    600
tgtctgtagg acccaaggac atgactgctc aatttaataa tctgggtgtc ctgcatgtaa    660
ccaagaagaa catgatggag attatgatcc agaaacttca gaggcagcgt ctccgctcca    720
agcctcaggg ccttacagag gctgagcggc gggagctaga gcaggaggcc aaggagctga    780
agaaagtcat ggatctgagc attgtacggc tgcgcttctc agctttcctt cgagctagcg    840
atggctcctt ctccttgccc ctgaagcctg tgatctccca gcccatccat gacagcaagt    900
ctccaggggc ctcgaacctg aagatctccc gaatggacaa gacagcgggt tccgtgcgcg    960
gtggagacga agtttatttg ctctgtgata aggtgcaaaa agacgacatt gaggttcggt    1020
tctatgagga tgatgagaat ggatggcaag cctttgggga cttctctccc acagacgttc    1080
ataaacagta tgccattgtg ttccggacac cgccctatca caagatgaag atcgagaggc    1140
ctgtaacagt gttcctgcag ctgaaacgca agcgtggggg cgatgtctcg gactccaaac    1200
agttcacata ttaccctctg gtggaagaca aggaggaagt gcagaggaag cggagaaagg    1260
ccttgcccac cttctcccag cccttcgggg gcggatccca catgggtgga ggttctgggg    1320
gctccgctgg gggttatgga ggcgctggag gaggtggcag cctcggcttt ttctcctcct    1380
ccttggccta caacccctac caatccggtg cagccccaat gggctgttat ccgggtgggg    1440
gaggtggagc gcagatggcc ggttctagac gggacaccga tgctggcgag ggggcagagg    1500
agcccaggac gccccggag gctcccagg gcgaaccaca ggcccttgac acactgcagc    1560
gagctcgcga gtacaacgcg cgcctgttcg gtctggcgca gcgcagcgcc cgagcgttgc    1620
tggactacgg cgtcaccgca gacgcgcgtg ctctgctagc gggacagcgc cacctgctga    1680
tggcacagga cgagaacgga gacacgccac tgcacctggc catcatccat gggcagactg    1740
gtgtcattga gcagatagcc cacgtcattt atcacgctca gtacctcggc gtcatcaacc    1800
tcaccaacca cctgcaccag acgcctctgc acctggcggt aatcactggg cagacaaggg    1860
tggtgagctt cctgctgcag gtgggtgcag accccacgct gctggatcgg cacggagact    1920 ccgcccteca cttggctctc cgggcaggtg ctgcagcccc agagctgttg caggcactgt    1980
tgcgcagcgg agcccatgct gtgcccaaaa tattgcacat gcctgatttt gagggactat    2040
accctgtaca cctggcagtc catgcccgaa gccctgagtg cctggatctg ttagttgact    2100
gtggagctga agtggaggcc ccagagaggc aaggggccg aactgccctg catctagcca    2160
cagagatgga ggagttgggg ctggtcaccc atcagtcac caagctccat gctaatgtga    2220
atgcccggac ctttgctgga aacacacccc tccacctggc agctggactc gggtccccaa    2280
ctcttactcg cctccttcta aaggctggtg ctgacatcca tgcagagaat gaggagcctc    2340
tgtgcccgct gccctcaccc tcgacctctg ggagcgactc cgactctgaa gggcctgaga    2400 gggatacccaa agaaacttc cgaggccata cccctcttga cctcacttgc agtaccaagg    2460
tgaagactct gctgctaaat gctgctcaga acaccacgga gccaccctg gccccaccca    2520
```

```
gccctgcagg gccagggctg tccctgggggg atgcagccct gcagaacctg gagcaactgc    2580
tggatggtcc cgaagcccag ggcagctggg cagagctggc agagcgactg gggttgagaa    2640
gcctggtgga cacatacagg aagaccccgt ctcccagcgg cagtctcctt cgtagttaca    2700
agctggctgg tggggacttg gtgggtctat tggaggcctt gtctgacatg gtctccatg     2760 agggagtcag gctgctgaaa ggtcctgaga cccgcgacaa gctgcccagc acagaggtga    2820
aagaagacag tgcctatggg agccagtcag tggagcagga ggcagagaag ctgtgtccac    2880
cccctgagcc tccaggaggg ctctgccacg gcaccccca gcctcaggtg cactgaatgg     2940
ccccggtcaa cttccaccca gatccctctg tacagcatcc ctgtctaatc gaaatcttat    3000
ttaaacctca agcccacatc tcggtgggtc aaataaaggg gaagaccctc cccaacttac    3060
ggtacagcaa ccccaatgtg ctgcccatcc cagtccctga gcgagaatag aggaggaggc    3120
ccagccagca a                                                        3131

<210> SEQ ID NO 5
<211> LENGTH: 2237
<212> TYPE: DNA
<213> ORGANISM: Mus musculus

<400> SEQUENCE: 5
ggagaagact actgtcttca acacactagc ctgagctacc ttatccaagt gctccacata     60
ttccagaagg agaaggacag acttcaagtt caaatcactt ccagagctgt gagtgacaag    120
tgccttggca ggtagtgcac gcctcatcac tgaaaggatc caaacaagac tgccatggaa    180
gaaaatgaat actcaggata ctgggaacct cctagaaagc gttgctgctg tgcaagacgt    240
gggacacagc tcatgttggt ggggctgctg agcacagcaa tgtgggctgg cctgctggcc    300
ctgcttcttc tgtggcactg ggaaacggag aagaatctaa aacagctggg agacactgca    360
attcagaatg tctctcatgt taccaaggac ttacaaaaat tccagagtaa tcaattggcc    420
cagaagtccc aggttgttca gatgtcacaa aacttgcaag aactccaagc tgaacagaag    480
caaatgaaag ctcaggactc tcggctctcc cagaacctga ccggactcca ggaggatcta    540
aggaacgccc aatcccagaa ctcaaaactc tcccagaacc tgaacagact ccaagacgat    600
ctagtcaaca tcaaatccct gggcttgaat gagaagcgca cagcctccga ttctctagag    660
aaactccagg aagaggtggc aaagctgtgg atagagatac tgatttcaaa gggaactgca    720
tgcaacatat gtcccaagaa ctggctccat ttccaacaga agtgctacta ttttggcaag    780
ggctccaagc agtggatcca ggccaggttc gcctgcagtg acctgcaagg gcgactagtc    840
agcatccaca gccaaaagga acaggacttc ctgatgcaac acatcaacaa gaaggattcc    900
tggattggcc tccaggatct caatatgagg ggagagtttg tatggtcgga cgggagccct    960
gtgggttata gcaactggaa tccaggggag cccaataacg ggggccaggg tgaggactgt    1020
gtgatgatgc gggatccgg ccagtggaac gacgccttct gccgcagcta cttggatgca    1080
tgggtgtgtg agcagctggc aacatgtgag atatctgccc ccttagcctc tgtgactcca    1140
acaaggccca cccaaaaag tgaacccgta caaacttctg ctcacactct tctggatttc    1200
tcctctacct ttatcgtgga aacagctggg ccctgaggat accccatca gggcccaggg    1260 ctctctgtga ccgaaggctt tgattatgtt cccaccccata ctgaagcagc tggtggatgc    1320
cagctcctgc cagctaccca gaaaccctct ccagctctcc agctaagctg gccatcccat    1380
tccatctgcc ttcctcaaac ctgggcccca gccttgctag ctccctgact acgggcatgc    1440
atgtgggcag ctgagccaac cagggagctg ctgagaacaa agatttcgaa ggcttctttt    1500
```

```
gcagtcccca cctcctatca agttcccac tttctccccc tcggcatcag agaacagggg    1560 ttcccttttcc ccaggatctg ggatgagtcc tcccatcaag tttgcatcag tggtcccagg   1620
actccgaccc tccttggagg ctaccaggtg tgctcctggt gcgggaggta ttgaaggaac    1680
tctaaacagc tccagcaagg cgagcctggc tctgtctggt aggcctggcc cttctctccc    1740
attccttcta ccttactaaa agctgttaga gaacagtcct aaagctagcc cccaaggtct    1800
attcccttat ttggccactt cctcctcctg aggctgacta caaggtccag ctatccaagt    1860
actgaagtct aacatcaaaa gccccctttg tctcacctaa gtagcaatgc ccaatcaaaa    1920
tacaccatca catcatagcc cagtctaaca gaccgcccct tttctcttca taaaattaca    1980
cctgcaacca ggcgtagtgg tgcaggcctt tagtcccagc acttgggagg cagagacaag    2040
cgaatttctg agttcgaggc cagcctggtc tacaaagtga gttccaggac agccagggct    2100
acacagagaa accctgtctc gaagaaagaa aaaaaaaaa aattacacct gcgaggtcac     2160
ttgggctgct gttttctgc ctgagtcaga gggcagccac ttaacttttc ttccctgctt     2220
aataaaggat ctctgtg                                                   2237

<210> SEQ ID NO 6
<211> LENGTH: 909
<212> TYPE: DNA
<213> ORGANISM: Homo sapiens

<400> SEQUENCE: 6
gcggtggctc cactggagga aaacacaccc cggtctcaca ttaaagaagc caaactgtcg     60
gcttcaaaga gaaaaggcaa catcctgtca caggccatgc tctggcaaaa acccacagct   120
ccggagcaag ccccagcccc ggcccggcca taccagggcg tccgtgtgaa ggagccagtg   180
aaggaactgc tgaggaggaa gcgaggccac gccagcagtg gggcagcacc tgcacctacg   240
gcggtggtgc tgccccatca gcccctggcg acctacacca cagtgggtcc ttcctgcctg   300
gacatggaag gttctgtgtc tgcagtgaca gaggaggctg ccctgtgtgc cggctggctc   360
tcccagccca ccccggccac cctgcagccc ctggccccat ggacacccta caccgagtat   420
gtgccccatg aagctgtcag ctgccccctac tcagctgaca tgtatgtgca gcccgtgtgc   480
cccagctaca cggtggtggg gccctcctca gtgttgacct atgcctctcc gccactcatc   540
accaatgtca cgacaagaag ctccgccacg cccgcagtgg ggccccccgct ggagggccca   600 gagcaccagg caccctcac ctatttcccg tggcctcagc cccttccac actacccacc    660 tccaccctgc agtaccagcc tccggcccca gccctacctg ggcccagtt tgtccagctc   720 cccatctcta tcccagagcc agtccttcag gacatggaag accccagaag agccgccagc   780
tcgttgacca tcgacaagct gcttttggag aagaggata gcgacgccta tgcgcttaac   840
cacactctct ctgtggaagg ctttttaggcg tggctcccac ctgagtcctg ttccctgaaa   900
ctgggattt                                                          909

<210> SEQ ID NO 7
<211> LENGTH: 1362
<212> TYPE: DNA
<213> ORGANISM: Homo sapiens

<400> SEQUENCE: 7
cctgtttggg acactggact cccgtgagct ggaaggaaca gatttaatat ctaggggctg     60
ggtatcccca catcactcat ttggggggtc aagggacccg ggcaatatag tattctgctc   120
agtgtctgga gatcatctac ccaggctggg gcttctggga caggcgagga cccacggacc   180
```

```
ctggaagagc tggtccaggg gactgaactc ccggcatctt tacagagcag agcatgatca    240
cattcctgcc gctgctgctg gggctcagcc tgggctgcac aggagcaggt ggcttcgtgg    300
cccatgtgga aagcacctgt ctgttggatg atgctgggac tccaaaggat ttcacatact    360
gcatctcctt caacaaggat ctgctgacct gctgggatcc agaggagaat aagatggccc    420
cttgcgaatt tggggtgctg aatagcttgg cgaatgtcct ctcacagcac ctcaaccaaa    480 aagcaccct gatgcagcgc ttgcgcaatg gcttcagaa ttgtgccaca cacacccagc    540
ccttctgggg atcactgacc aacaggacac ggccaccatc tgtgcaagta gccaaaacca    600
ctccttttaa cacgagggag cctgtgatgc tggcctgcta tgtgtggggc ttctatccag    660
cagaagtgac tatcacgtgg aggaagaacg ggaagcttgt catgcctcac agcagtgcgc    720
acaagactgc ccagcccaat ggagactgga cataccagac cctctcccat ttagccttaa    780
ccccctctta cggggacact tacacctgtg tggtagagca cattggggct cctgagccca    840
tccttcggga ctggacacct gggctgtccc ccatgcagac cctgaaggtt tctgtgtctg    900
cagtgactct gggcctgggc tcatcatct tctctcttgg tgtgatcagc tggcggagag    960
ctggccactc tagttacact cctcttcctg ggtccaatta ttcagaagga tggcacattt   1020
cctagaggca gaatcctaca acttccactc caagtgagaa ggagattcaa actcaatgat   1080
gctaccatgc ctctccaaca tcttcaaccc cctgacatta tcttggatcc tatggttct   1140 ccatccaatt ctttgaattt cccagtctcc cctatgtaaa acttagcaac ttgggggacc   1200
tcattcctgg gactatgctg taaccaaatt attgtccaag gctatatttc tgggatgaat   1260
ataatctgag gaagggagtt aaagaccctc ctgggctct cagtgtgcca tagaggacag   1320
caactggtga ttgtttcaga gaaataaact ttggtggaaa aa                      1362
```

<210> SEQ ID NO 8
<211> LENGTH: 1844
<212> TYPE: DNA
<213> ORGANISM: Homo sapiens

<400> SEQUENCE: 8

```
gacagtggag ggcagtggag aggaccgcgc tgtcctgctg tcaccaagag ctggagacac     60
catctcccac cgagagtcat ggccccattg gccctgcacc tcctcgtcct cgtccccatc    120
ctcctcagcc tggtggcctc ccaggactgg aaggctgaac gcagccaaga ccccttcgag    180
aaatgcatgc aggatcctga ctatgagcag ctgctcaagg tggtgacctg ggggctcaat    240
cggaccctga agccccagag ggtgattgtg gttggcgctg gtgtggccgg gctggtggcc    300
gccaaggtgc tcagcgatgc tggacacaag gtcaccatcc tggaggcaga taacaggatc    360
gggggccgca tcttcaccta ccgggaccag aacacgggct ggattgggga gctgggagcc    420
atgcgcatgc ccagctctca caggatcctc acaagctct gccagggcct ggggctcaac    480
ctgaccaagt tcacccagta cgacaagaac acgtggacgg aggtgcacga agtgaagctg    540
cgcaactatg tggtggagaa ggtgcccgag aagctgggct acgccttgcg tccccaggaa    600
aagggccact cgcccgaaga catctaccag atggctctca accaggccct caaagacctc    660
aaggcactgg gctgcagaaa ggcgatgaag aagtttgaaa ggcacacgct cttggaatat    720
cttctcgggg aggggaacct gagccggccg gccgtgcagc ttctgggaga cgtgatgtcc    780
gaggatggct tcttctatct cagcttcgcc gaggccctcc gggcccacag ctgcctcagc    840
gacagactcc agtacagccg catcgtgggt ggctgggacc tgctgccgcg cgcgctgctg    900
agctcgctgt ccgggcttgt gctgttgaac gcgcccgtgg tggcgatgac ccagggaccg    960
```

-continued

| | | |
|---|---|---|
| cacgatgtgc acgtgcagat cgagacctct cccccggcgc ggaatctgaa ggtgctgaag | 1020 |
| gccgacgtgg tgctgctgac ggcgagcgga ccggcggtga agcgcatcac cttctcgccg | 1080 |
| ccgctgcccc gccacatgca ggaggcgctg cggaggctgc actacgtgcc ggccaccaag | 1140 |
| gtgttcctaa gcttccgcag gcccttctgg cgcgaggagc acattgaagg cggccactca | 1200 |
| aacaccgatc gcccgtcgcg catgattttc tacccgccgc cgcgcgaggg cgcgctgctg | 1260 |
| ctggcctcgt acacgtggtc ggacgcggcg gcagcgttcg ccggcttgag ccgggaagag | 1320 |
| gcgttgcgct tggcgctcga cgacgtggcg gcattgcacg ggcctgtcgt gcgccagctc | 1380 |
| tgggacggca ccgcgtcgt caagcgttgg gcggaggacc agcacagcca gggtggcttt | 1440 |
| gtggtacagc cgccggcgct ctggcaaacc gaaaaggatg actggacggt cccttatggc | 1500 |
| cgcatctact tgccggcga gcacaccgcc tacccgcacg gctgggtgga cggcggtc | 1560 |
| aagtcggcgc tgcgcgccgc catcaagatc aacagccgga aggggcctgc atcggacacg | 1620 |
| gccagccccg aggggcacgc atctgacatg gaggggcagg gcatgtgca tggggtggcc | 1680 |
| agcagcccct cgcatgacct ggcaaaggaa gaaggcagcc accctccagt ccaaggccag | 1740 |
| ttatctctcc aaaacacgac ccacacgagg acctcgcatt aaagtatttt cggaaaaaaa | 1800 |
| aaaaaaaaaa aaaaaaaaaa aaaaaaaaaa aaaaaaaaaa aaaa | 1844 |

<210> SEQ ID NO 9
<211> LENGTH: 3016
<212> TYPE: DNA
<213> ORGANISM: Homo sapiens

<400> SEQUENCE: 9

| | | |
|---|---|---|
| agaagccgca accagagccg ccgccacggc gggcgtctaa aattctggga agcagaacct | 60 |
| ggccggagcc actagacaga gccgggccta gcccagagac atggagagtt gctacaaccc | 120 |
| aggtctggat ggtattattg aatatgatga tttcaaattg aactcctcca ttgtggaacc | 180 |
| caaggagcca gccccagaaa cagctgatgg cccctacctg gtgatcgtgg aacagcctaa | 240 |
| gcagagaggc ttccgatttc gatatggctg tgaaggcccc tcccatggag gactgcccgg | 300 |
| tgcctccagt gagaagggcc gaaagaccta tcccactgtc aagatctgta actacgaggg | 360 |
| accagccaag atcgaggtgg acctggtaac acacagtgac ccacctcgtg ctcatgccca | 420 |
| cagtctggtg ggcaagcaat gctcggagct ggggatctgc gccgtttctg tggggcccaa | 480 |
| ggacatgact gcccaattta acaacctggg tgtcctgcat gtgactaaga gaacatgat | 540 |
| ggggactatg atacaaaaac ttcagaggca gcggctccgc tctaggcccc agggccttac | 600 |
| ggaggccgag cagcgggagc tggagcaaga ggccaaagaa ctgaagaagg tgatggatct | 660 |
| gagtatagtg cggctgcgct ctctgcctt cctagagcc agtgatggct ccttctccct | 720 |
| gcccctgaag ccagtcatct cccagcccat ccatgacagc aaatctccgg gggcatcaaa | 780 |
| cctgaagatt tctcgaatgg acaagacagc aggctctgtg cggggtggag atgaagttta | 840 |
| tctgctttgt gacaaggtgc agaaagatga cattgaggtt cggttctatg aggatgatga | 900 |
| gaatggatgg caggcctttg gggacttctc tcccacagat gtgcataaac agtatgccat | 960 |
| tgtgttccgg acacccccct atcacaagat gaagattgag cggcctgtaa cagtgtttct | 1020 |
| gcaactgaaa cgcaagcgag gagggacgt gtctgattcc aaacagttca cctattaccc | 1080 |
| tctggtggaa gacaaggaag aggtgcagcg gaagcggagg aaggccttgc caccttctc | 1140 |
| ccagcccttc gggggtggct cccacatggg tggaggctct gggggtgcag ccgggggcta | 1200 |
| cggaggagct ggaggaggtg gcagcctcgg tttcttcccc cctccctgg cctacagccc | 1260 |

-continued

| | |
|---|---|
| ctaccagtcc ggcgcgggcc ccatgggctg ctacccggga ggcgggggcg gggcgcagat | 1320 |
| ggccgccacg gtgcccagca gggactccgg ggaggaagcc gcggagccga gcgccccctc | 1380 |
| caggacccc cagtgcgagc cgcaggcccc ggagatgctg cagcgagctc gagagtacaa | 1440 |
| cgcgcgcctg ttcggcctgg cgcagcgcag cgcccgagcc ctactcgact acggcgtcac | 1500 |
| cgcggacgcg cgcgcgctgc tggcgggaca gcgccacctg ctgacggcgc aggacgagaa | 1560 |
| cggagacaca ccactgcacc tagccatcat ccacgggcag accagtgtca ttgagcagat | 1620 |
| agtctatgtc atccaccacg cccaggacct cggcgttgtc aacctcacca accacctgca | 1680 |
| ccagacgccc ctgcacctgg cggtgatcac ggggcagacg agtgtggtga gctttctgct | 1740 |
| gcgggtaggt gcagacccag ctctgctgga tcggcatgga gactcagcca tgcatctggc | 1800 |
| gctgcgggca ggcgctggtg ctcctgagct gctgcgtgca ctgcttcaga gtggagctcc | 1860 |
| tgctgtgccc cagctgttgc atatgcctga cttgaggga ctgtatccag tacacctggc | 1920 |
| ggtccgagcc cgaagccctg agtgcctgga tctgctggtg gacagtgggg ctgaagtgga | 1980 |
| ggccactgag cggcaggggg gacgaacagc cttgcatcta gccacagaga tggaggagct | 2040 |
| ggggttggtc acccatctgg tcaccaagct ccgggccaac gtgaacgctc gcacctttgc | 2100 |
| gggaaacaca cccctgcacc tggcagctgg actgggtac ccgaccctca cccgcctcct | 2160 |
| tctgaaggct ggtgctgaca tccatgctga aaacgaggag cccctgtgcc cactgccttc | 2220 |
| acccccctacc tctgatagcg actcggactc tgaagggcct gagaaggaca cccgaagcag | 2280 |
| cttccggggc cacacgcctc ttgacctcac ttgcagcacc aaggtgaaga ccttgctgct | 2340 |
| aaatgctgct cagaacacca tggagccacc cctgaccccg cccagcccag cagggccggg | 2400 |
| actgtcactt ggtgatacag ctctgcagaa cctggagcag ctgctagacg gccagaagc | 2460 |
| ccagggcagc tgggcagagc tggcagagcg tctgggctg cgcagcctgg tagacacgta | 2520 |
| ccgacagaca acctcaccca gtggcagcct cctgcgcagc tacgagctgg ctggcgggga | 2580 |
| cctggcaggt ctactggagg ccctgtctga catgggccta aggagggag tgaggctgct | 2640 |
| gaggggtcca gaaacccgag acaagctgcc cagcacagag gtgaaggaag acagtgcgta | 2700 |
| cgggagccag tcagtggagc aggaggcaga gaagctgggc ccaccccctg agccaccagg | 2760 |
| agggctctgc cacgggcacc cccagcctca ggtgcactga cctgctgcct gcccccagcc | 2820 |
| cccttcccgg accccctgta cagcgtcccc acctatttca aatcttattt aacaccccac | 2880 |
| acccaccccct cagttgggac aaataaagga ttctcatggg aaggggagga cccctccttc | 2940 |
| ccaacttaaa aaaaaaaaa aaaaaaaaaa aaaaaaaaa aaaaaaaaa aaaaaaaaa | 3000 |
| aaaaaaaaaa aaaaaa | 3016 |

```
<210> SEQ ID NO 10
<211> LENGTH: 1650
<212> TYPE: DNA
<213> ORGANISM: Homo sapiens

<400> SEQUENCE: 10
```

| | |
|---|---|
| tctgtctctg acggtccctg ccaatcgctc tggtcgaccc caacacacta ggaggacaga | 60 |
| cacaggctcc aaactccact aagtgaccag agctgtgatt gtgcccgctg agtggactgc | 120 |
| gttgtcaggg agtgagtgct ccatcatcgg agaatccaa gcaggaccgc catgaggaa | 180 |
| ggtcaatatt cagagatcga ggagcttccc aggaggcggt gttgcaggcg tgggactcag | 240 |
| atcgtgctgc tggggctggt gaccgccgct ctgtgggctg gctgctgac tctgcttctc | 300 |
| ctgtggcact gggacaccac acagagtcta aaacagctgg aagagagggc tgcccggaac | 360 |

```
gtctctcaag tttccaagaa cttggaaagc caccacggtg accagatggc gcagaaatcc    420
cagtccacgc agatttcaca ggaactggag gaacttcgag ctgaacagca gagattgaaa    480
tctcaggact tggagctgtc ctggaacctg aacgggcttc aagcagatct gagcagcttc    540
aagtcccagg aattgaacga gaggaacgaa gcttcagatt tgctggaaag actccgggag    600
gaggtgacaa agctaaggat ggagttgcag gtgtccagcg gctttgtgtg caacacgtgc    660
cctgaaaagt ggatcaattt ccaacggaag tgctactact tcggcaaggg caccaagcag    720
tgggtccacg cccggtatgc ctgtgacgac atggaagggc agctggtcag catccacagc    780
ccggaggagc aggacttcct gaccaagcat gccagccaca ccggctcctg gattggcctt    840
cggaacttgg acctgaaggg ggagtttatc tgggtggatg ggagccacgt ggactacagc    900
aactgggctc caggggagcc caccagccgg agccagggcg aggactgcgt gatgatgcgg    960
ggctccggtc gctggaacga cgccttctgc gaccgtaagc tgggcgcctg ggtgtgcgac    1020
cggctggcca catgcacgcc gccagccagc gaaggttccg cggagtccat gggacctgat    1080
tcaagaccag accctgacgg ccgcctgccc acccctctg ccctctcca ctcttgagca    1140 tggatacagc caggcccaga gcaagaccct gaagaccccc aaccacggcc taaaagcctc    1200
tttgtggctg aaaggtccct gtgacatttt ctgccaccca acggaggca gctgacacat    1260 ctcccgctcc tctatggccc ctgccttccc aggagtacac cccaacagca ccctctccag    1320
atgggagtgc ccccaacagc accctctcca gatgagagta caccccaaca gcaccctctc    1380
cagatgagag tacaccccaa cagcaccctc tccagatgag agtacacccc aacagcaccc    1440
tctccagatg cagccccatc tcctcagcac cccaggacct gagtatcccc agctcaggtg    1500
gtgagtcctc ctgtccagcc tgcatcaata aatggggca gtgatggcct cccaaaaaaa    1560
aaaaaaaaaa aaaaaaaaaa aaaaaaaaaa aaaaaaaaaa aaaaaaaaaa aaaaaaaaaa    1620
aaaaaaaaaa aaaaaaaaaa aaaaaaaaa                                     1650
```

<210> SEQ ID NO 11
<211> LENGTH: 256
<212> TYPE: PRT
<213> ORGANISM: Mus musculus

<400> SEQUENCE: 11

```
Met Leu Trp Gln Lys Ser Thr Ala Pro Glu Gln Ala Pro Ala Pro Pro
1               5                   10                  15

Arg Pro Tyr Gln Gly Val Arg Val Lys Glu Pro Val Lys Glu Leu Leu
            20                  25                  30

Arg Arg Lys Arg Gly His Thr Ser Val Gly Ala Ala Gly Pro Pro Thr
        35                  40                  45

Ala Val Val Leu Pro His Gln Pro Leu Ala Thr Tyr Ser Thr Val Gly
    50                  55                  60

Pro Ser Cys Leu Asp Met Glu Val Ser Ala Ser Thr Val Thr Glu Glu
65                  70                  75                  80

Gly Thr Leu Cys Ala Gly Trp Leu Ser Gln Pro Ala Pro Ala Thr Leu
                85                  90                  95

Gln Pro Leu Ala Pro Trp Thr Pro Tyr Thr Glu Tyr Val Ser His Glu
            100                 105                 110

Ala Val Ser Cys Pro Tyr Ser Thr Asp Met Tyr Val Gln Pro Val Cys
        115                 120                 125

Pro Ser Tyr Thr Val Val Gly Pro Ser Val Leu Thr Tyr Ala Ser
    130                 135                 140

Pro Pro Leu Ile Thr Asn Val Thr Pro Arg Ser Thr Ala Thr Pro Ala
```

```
                   145                 150                 155                 160

Val Gly Pro Gln Leu Glu Gly Pro Glu His Gln Ala Pro Leu Thr Tyr
                     165                 170                 175

Phe Pro Trp Pro Gln Pro Leu Ser Thr Leu Pro Thr Ser Ser Leu Gln
                     180                 185                 190

Tyr Gln Pro Pro Ala Pro Thr Leu Ser Gly Pro Gln Phe Val Gln Leu
                     195                 200                 205

Pro Ile Ser Ile Pro Glu Pro Val Leu Gln Asp Met Asp Asp Pro Arg
                     210                 215                 220

Arg Ala Ile Ser Ser Leu Thr Ile Asp Lys Leu Leu Leu Glu Glu Glu
     225                 230                 235                 240

Glu Ser Asn Thr Tyr Glu Leu Asn His Thr Leu Ser Val Glu Gly Phe
                     245                 250                 255

<210> SEQ ID NO 12
<211> LENGTH: 261
<212> TYPE: PRT
<213> ORGANISM: Mus musculus

<400> SEQUENCE: 12

Met Ala Ala Leu Trp Leu Leu Leu Leu Val Leu Ser Leu Asp Cys Met
1               5                   10                  15

Gly Ala Gly Gly Phe Val Ala His Val Glu Ser Thr Cys Val Leu Asp
                20                  25                  30

Asp Ala Gly Thr Pro Gln Asp Phe Thr Tyr Cys Val Ser Phe Asn Lys
            35                  40                  45

Asp Leu Leu Ala Cys Trp Asp Pro Asp Val Gly Lys Ile Val Pro Cys
        50                  55                  60

Glu Phe Gly Val Leu Tyr Pro Trp Ala Glu Asn Phe Ser Arg Ile Leu
65                  70                  75                  80

Asn Lys Glu Glu Ser Leu Leu Gln Arg Leu Gln Asn Gly Leu Leu Asp
                85                  90                  95

Cys Ala Ser His Thr Gln Pro Phe Trp Asn Ala Leu Thr His Arg Thr
            100                 105                 110

Arg Ala Pro Ser Val Arg Val Ala Gln Thr Thr Pro Phe Asn Thr Arg
        115                 120                 125

Glu Pro Val Met Leu Ala Cys Tyr Val Trp Gly Phe Tyr Pro Ala Asp
    130                 135                 140

Val Thr Ile Thr Trp Met Lys Asn Gly Gln Leu Val Pro Ser His Ser
145                 150                 155                 160

Asn Lys Glu Lys Thr Ala Gln Pro Asn Gly Asp Trp Thr Tyr Gln Thr
                165                 170                 175

Val Ser Tyr Leu Ala Leu Thr Pro Ser Tyr Gly Asp Val Tyr Thr Cys
            180                 185                 190

Val Val Gln His Ser Gly Thr Ser Glu Pro Ile Arg Gly Asp Trp Thr
        195                 200                 205

Pro Gly Leu Ser Pro Ile Gln Thr Val Lys Val Ser Val Ser Ala Ala
    210                 215                 220

Thr Leu Gly Leu Gly Phe Ile Ile Phe Cys Val Gly Phe Phe Arg Trp
225                 230                 235                 240

Arg Lys Ser His Ser Ser Ser Tyr Thr Pro Leu Ser Gly Ser Thr Tyr
                245                 250                 255

Pro Glu Gly Gln His
            260
```

<210> SEQ ID NO 13
<211> LENGTH: 630
<212> TYPE: PRT
<213> ORGANISM: Mus musculus

<400> SEQUENCE: 13

```
Met Ala Gly Leu Ala Leu Arg Leu Val Leu Ala Thr Leu Leu Gly
1               5                   10                  15

Leu Ala Gly Ser Leu Asp Trp Lys Ala Ala Ser Ser Leu Asn Pro Ile
                20                  25                  30

Glu Lys Cys Met Glu Asp His Asp Tyr Glu Gln Leu Leu Lys Val Val
            35                  40                  45

Thr Leu Gly Leu Asn Arg Thr Ser Lys Pro Gln Lys Val Val Val
50                  55                  60

Gly Ala Gly Val Ala Gly Leu Val Ala Ala Lys Met Leu Ser Asp Ala
65                  70                  75                  80

Gly His Lys Val Thr Ile Leu Glu Ala Asp Asn Arg Ile Gly Gly Arg
                85                  90                  95

Ile Phe Thr Phe Arg Asp Glu Lys Thr Gly Trp Ile Gly Glu Leu Gly
            100                 105                 110

Ala Met Arg Met Pro Ser Ser His Arg Ile Leu His Lys Leu Cys Arg
        115                 120                 125

Thr Leu Gly Leu Asn Leu Thr Gln Phe Thr Gln Tyr Asp Glu Asn Thr
130                 135                 140

Trp Thr Glu Val His Asn Val Lys Leu Arg Asn Tyr Val Val Glu Lys
145                 150                 155                 160

Met Pro Glu Lys Leu Gly Tyr Asn Leu Asn Asn Arg Glu Arg Gly His
                165                 170                 175

Ser Pro Glu Asp Ile Tyr Gln Met Ala Leu Asn Lys Ala Phe Lys Asp
            180                 185                 190

Leu Lys Ala Leu Gly Cys Lys Lys Ala Met Asn Lys Phe Asn Lys His
        195                 200                 205

Thr Leu Leu Glu Tyr Leu Leu Glu Glu Gly Asn Leu Ser Arg Pro Ala
210                 215                 220

Val Gln Leu Leu Gly Asp Val Met Ser Glu Gly Phe Phe Tyr Leu
225                 230                 235                 240

Ser Phe Ala Glu Ala Leu Arg Ala His Ala Cys Leu Ser Asp Arg Leu
                245                 250                 255

Arg Tyr Ser Arg Ile Val Gly Gly Trp Asp Leu Leu Pro Arg Ala Leu
            260                 265                 270

Leu Ser Ser Leu Ser Gly Ala Leu Leu Leu Asn Ala Pro Val Val Ser
        275                 280                 285

Ile Thr Gln Gly Arg Asn Asp Val Arg Val His Ile Ala Thr Ser Leu
290                 295                 300

His Ser Glu Lys Thr Leu Thr Ala Asp Val Val Leu Leu Thr Ala Ser
305                 310                 315                 320

Gly Pro Ala Leu Gln Arg Ile Thr Phe Ser Pro Pro Leu Thr Arg Lys
                325                 330                 335

Arg Gln Glu Ala Leu Arg Ala Leu His Tyr Val Ala Ala Ser Lys Val
            340                 345                 350

Phe Leu Ser Phe Arg Arg Pro Phe Trp His Glu Glu His Ile Glu Gly
        355                 360                 365

Gly His Ser Asn Thr Asp Arg Pro Ser Arg Leu Ile Phe Tyr Pro Ala
370                 375                 380
```

Arg Gly Glu Gly Ser Leu Leu Ala Ser Tyr Thr Trp Ser Asp Ala
385                 390                 395                 400

Ala Ala Pro Phe Ala Gly Leu Ser Thr Asp Gln Thr Leu Arg Leu Val
            405                 410                 415

Leu Gln Asp Val Ala Ala Leu His Gly Pro Val Val Phe Arg Leu Trp
        420                 425                 430

Asp Gly Arg Gly Val Val Lys Arg Trp Ala Glu Asp Pro His Ser Gln
    435                 440                 445

Gly Gly Phe Val Val Gln Pro Pro Leu Tyr Gly Arg Glu Ala Glu Asp
450                 455                 460

Tyr Asp Trp Ser Ala Pro Phe Gly Arg Ile Tyr Phe Ala Gly Glu His
465                 470                 475                 480

Thr Ala Leu Pro His Gly Trp Val Glu Thr Ala Val Lys Ser Gly Leu
            485                 490                 495

Arg Ala Ala Val Arg Ile Asn Asn Asn Tyr Gly Tyr Gly Glu Val Asp
        500                 505                 510

Pro Gln Met Met Glu His Ala Tyr Ala Glu Ala Asn Tyr Leu Asp Gln
    515                 520                 525

Tyr Pro Glu Gly Glu Arg Pro Glu Gln Gln Ala Arg Glu Glu Val
530                 535                 540

Ser Pro Asp Glu Gln Glu Pro Ser His Lys His Leu Leu Val Glu Thr
545                 550                 555                 560

Ser Pro Glu Gly Gln Gln His Ala Phe Val Glu Ala Ile Pro Glu Leu
            565                 570                 575

Gln Gly His Val Phe Val Glu Thr Val Pro Gln Glu Lys Gly His Ala
        580                 585                 590

His Gln Asn Ile Tyr Pro Ser Glu His Val Gln Val His Gly Glu Val
    595                 600                 605

Ile Pro Glu Trp His Gly His Gly Ser Gly Thr Pro Gln Met His
610                 615                 620

Arg Val Gly Asp His Ser
625                 630

<210> SEQ ID NO 14
<211> LENGTH: 899
<212> TYPE: PRT
<213> ORGANISM: Mus musculus

<400> SEQUENCE: 14

Met Asp Asn Cys Tyr Asp Pro Gly Leu Asp Gly Ile Pro Glu Tyr Asp
1               5                   10                  15

Asp Phe Glu Phe Ser Pro Ser Ile Val Glu Pro Lys Asp Pro Ala Pro
            20                  25                  30

Glu Thr Ala Asp Gly Pro Tyr Leu Val Ile Val Glu Gln Pro Lys Gln
        35                  40                  45

Arg Gly Phe Arg Phe Arg Tyr Gly Cys Glu Gly Pro Ser His Gly Gly
    50                  55                  60

Leu Pro Gly Ala Ser Ser Glu Lys Gly Arg Lys Thr Tyr Pro Thr Val
65                  70                  75                  80

Lys Ile Cys Asn Tyr Glu Gly Pro Ala Lys Ile Glu Val Asp Leu Val
                85                  90                  95

Thr His Ser Asp Pro Pro Arg Ala His Ala His Ser Leu Val Gly Lys
            100                 105                 110

Gln Cys Ser Glu Leu Gly Val Cys Ala Val Ser Val Gly Pro Lys Asp
        115                 120                 125

```
Met Thr Ala Gln Phe Asn Asn Leu Gly Val Leu His Val Thr Lys Lys
130                 135                 140

Asn Met Met Glu Ile Met Ile Gln Lys Leu Gln Arg Gln Arg Leu Arg
145                 150                 155                 160

Ser Lys Pro Gln Gly Leu Thr Glu Ala Glu Arg Arg Glu Leu Glu Gln
        165                 170                 175

Glu Ala Lys Glu Leu Lys Lys Val Met Asp Leu Ser Ile Val Arg Leu
            180                 185                 190

Arg Phe Ser Ala Phe Leu Arg Ala Ser Asp Gly Ser Phe Ser Leu Pro
        195                 200                 205

Leu Lys Pro Val Ile Ser Gln Pro Ile His Asp Ser Lys Ser Pro Gly
210                 215                 220

Ala Ser Asn Leu Lys Ile Ser Arg Met Asp Lys Thr Ala Gly Ser Val
225                 230                 235                 240

Arg Gly Gly Asp Glu Val Tyr Leu Leu Cys Asp Lys Val Gln Lys Asp
            245                 250                 255

Asp Ile Glu Val Arg Phe Tyr Glu Asp Glu Asn Gly Trp Gln Ala
        260                 265                 270

Phe Gly Asp Phe Ser Pro Thr Asp Val His Lys Gln Tyr Ala Ile Val
        275                 280                 285

Phe Arg Thr Pro Pro Tyr His Lys Met Lys Ile Glu Arg Pro Val Thr
290                 295                 300

Val Phe Leu Gln Leu Lys Arg Lys Arg Gly Gly Asp Val Ser Asp Ser
305                 310                 315                 320

Lys Gln Phe Thr Tyr Tyr Pro Leu Val Glu Asp Lys Glu Glu Val Gln
                325                 330                 335

Arg Lys Arg Arg Lys Ala Leu Pro Thr Phe Ser Gln Pro Phe Gly Gly
            340                 345                 350

Gly Ser His Met Gly Gly Gly Ser Gly Gly Ser Ala Gly Gly Tyr Gly
        355                 360                 365

Gly Ala Gly Gly Gly Gly Ser Leu Gly Phe Phe Ser Ser Ser Leu Ala
370                 375                 380

Tyr Asn Pro Tyr Gln Ser Gly Ala Ala Pro Met Gly Cys Tyr Pro Gly
385                 390                 395                 400

Gly Gly Gly Gly Ala Gln Met Ala Gly Ser Arg Arg Asp Thr Asp Ala
            405                 410                 415

Gly Glu Gly Ala Glu Glu Pro Arg Thr Pro Glu Ala Pro Gln Gly
            420                 425                 430

Glu Pro Gln Ala Leu Asp Thr Leu Gln Arg Ala Arg Glu Tyr Asn Ala
        435                 440                 445

Arg Leu Phe Gly Leu Ala Gln Arg Ser Ala Arg Ala Leu Leu Asp Tyr
        450                 455                 460

Gly Val Thr Ala Asp Ala Arg Ala Leu Leu Ala Gly Gln Arg His Leu
465                 470                 475                 480

Leu Met Ala Gln Asp Glu Asn Gly Asp Thr Pro Leu His Leu Ala Ile
            485                 490                 495

Ile His Gly Gln Thr Gly Val Ile Glu Gln Ile Ala His Val Ile Tyr
        500                 505                 510

His Ala Gln Tyr Leu Gly Val Ile Asn Leu Thr Asn His Leu His Gln
        515                 520                 525

Thr Pro Leu His Leu Ala Val Ile Thr Gly Gln Thr Arg Val Val Ser
530                 535                 540

Phe Leu Leu Gln Val Gly Ala Asp Pro Thr Leu Leu Asp Arg His Gly
```

```
                545                 550                 555                 560
Asp Ser Ala Leu His Leu Ala Leu Arg Ala Gly Ala Ala Pro Glu
                565                 570                 575

Leu Leu Gln Ala Leu Leu Arg Ser Gly Ala His Ala Val Pro Gln Ile
                580                 585                 590

Leu His Met Pro Asp Phe Glu Gly Leu Tyr Pro Val His Leu Ala Val
                595                 600                 605

His Ala Arg Ser Pro Glu Cys Leu Asp Leu Leu Val Asp Cys Gly Ala
            610                 615                 620

Glu Val Glu Ala Pro Glu Arg Gln Gly Gly Arg Thr Ala Leu His Leu
625                 630                 635                 640

Ala Thr Glu Met Glu Glu Leu Gly Leu Val Thr His Leu Val Thr Lys
                645                 650                 655

Leu His Ala Asn Val Asn Ala Arg Thr Phe Ala Gly Asn Thr Pro Leu
                660                 665                 670

His Leu Ala Ala Gly Leu Gly Ser Pro Thr Leu Thr Arg Leu Leu Leu
            675                 680                 685

Lys Ala Gly Ala Asp Ile His Ala Glu Asn Glu Glu Pro Leu Cys Pro
            690                 695                 700

Leu Pro Ser Pro Ser Thr Ser Gly Ser Asp Ser Asp Ser Glu Gly Pro
705                 710                 715                 720

Glu Arg Asp Thr Gln Arg Asn Phe Arg Gly His Thr Pro Leu Asp Leu
                725                 730                 735

Thr Cys Ser Thr Lys Val Lys Thr Leu Leu Leu Asn Ala Ala Gln Asn
                740                 745                 750

Thr Thr Glu Pro Pro Leu Ala Pro Pro Ser Pro Ala Gly Pro Gly Leu
            755                 760                 765

Ser Leu Gly Asp Ala Ala Leu Gln Asn Leu Glu Gln Leu Leu Asp Gly
            770                 775                 780

Pro Glu Ala Gln Gly Ser Trp Ala Glu Leu Ala Glu Arg Leu Gly Leu
785                 790                 795                 800

Arg Ser Leu Val Asp Thr Tyr Arg Lys Thr Pro Ser Pro Ser Gly Ser
                805                 810                 815

Leu Leu Arg Ser Tyr Lys Leu Ala Gly Gly Asp Leu Val Gly Leu Leu
                820                 825                 830

Glu Ala Leu Ser Asp Met Gly Leu His Glu Gly Val Arg Leu Leu Lys
            835                 840                 845

Gly Pro Glu Thr Arg Asp Lys Leu Pro Ser Thr Glu Val Lys Glu Asp
850                 855                 860

Ser Ala Tyr Gly Ser Gln Ser Val Glu Gln Glu Ala Glu Lys Leu Cys
865                 870                 875                 880

Pro Pro Pro Glu Pro Pro Gly Gly Leu Cys His Gly His Pro Gln Pro
                885                 890                 895

Gln Val His

<210> SEQ ID NO 15
<211> LENGTH: 331
<212> TYPE: PRT
<213> ORGANISM: Mus musculus

<400> SEQUENCE: 15

Met Glu Glu Asn Glu Tyr Ser Gly Tyr Trp Glu Pro Pro Arg Lys Arg
1               5                   10                  15

Cys Cys Cys Ala Arg Arg Gly Thr Gln Leu Met Leu Val Gly Leu Leu
                20                  25                  30
```

```
Ser Thr Ala Met Trp Ala Gly Leu Leu Ala Leu Leu Leu Trp His
        35                  40                  45

Trp Glu Thr Glu Lys Asn Leu Lys Gln Leu Gly Asp Thr Ala Ile Gln
 50                  55                  60

Asn Val Ser His Val Thr Lys Asp Leu Gln Lys Phe Gln Ser Asn Gln
 65                  70                  75                  80

Leu Ala Gln Lys Ser Gln Val Val Gln Met Ser Gln Asn Leu Gln Glu
                 85                  90                  95

Leu Gln Ala Glu Gln Lys Gln Met Lys Ala Gln Asp Ser Arg Leu Ser
            100                 105                 110

Gln Asn Leu Thr Gly Leu Gln Glu Asp Leu Arg Asn Ala Gln Ser Gln
        115                 120                 125

Asn Ser Lys Leu Ser Gln Asn Leu Asn Arg Leu Gln Asp Asp Leu Val
    130                 135                 140

Asn Ile Lys Ser Leu Gly Leu Asn Glu Lys Arg Thr Ala Ser Asp Ser
145                 150                 155                 160

Leu Glu Lys Leu Gln Glu Val Ala Lys Leu Trp Ile Glu Ile Leu
                165                 170                 175

Ile Ser Lys Gly Thr Ala Cys Asn Ile Cys Pro Lys Asn Trp Leu His
            180                 185                 190

Phe Gln Gln Lys Cys Tyr Tyr Phe Gly Lys Gly Ser Lys Gln Trp Ile
        195                 200                 205

Gln Ala Arg Phe Ala Cys Ser Asp Leu Gln Gly Arg Leu Val Ser Ile
    210                 215                 220

His Ser Gln Lys Glu Gln Asp Phe Leu Met Gln His Ile Asn Lys Lys
225                 230                 235                 240

Asp Ser Trp Ile Gly Leu Gln Asp Leu Asn Met Glu Gly Glu Phe Val
                245                 250                 255

Trp Ser Asp Gly Ser Pro Val Gly Tyr Ser Asn Trp Asn Pro Gly Glu
            260                 265                 270

Pro Asn Asn Gly Gly Gln Gly Glu Asp Cys Val Met Met Arg Gly Ser
        275                 280                 285

Gly Gln Trp Asn Asp Ala Phe Cys Arg Ser Tyr Leu Asp Ala Trp Val
    290                 295                 300

Cys Glu Gln Leu Ala Thr Cys Glu Ile Ser Ala Pro Leu Ala Ser Val
305                 310                 315                 320

Thr Pro Thr Arg Pro Thr Pro Lys Ser Glu Pro
                325                 330

<210> SEQ ID NO 16
<211> LENGTH: 256
<212> TYPE: PRT
<213> ORGANISM: Homo sapiens

<400> SEQUENCE: 16

Met Leu Trp Gln Lys Pro Thr Ala Pro Glu Gln Ala Pro Ala Pro Ala
 1               5                  10                  15

Arg Pro Tyr Gln Gly Val Arg Val Lys Glu Pro Val Lys Glu Leu Leu
                20                  25                  30

Arg Arg Lys Arg Gly His Ala Ser Ser Gly Ala Ala Pro Ala Pro Thr
            35                  40                  45

Ala Val Val Leu Pro His Gln Pro Leu Ala Thr Tyr Thr Thr Val Gly
        50                  55                  60

Pro Ser Cys Leu Asp Met Glu Gly Ser Val Ser Ala Val Thr Glu Glu
 65                  70                  75                  80
```

```
Ala Ala Leu Cys Ala Gly Trp Leu Ser Gln Pro Thr Pro Ala Thr Leu
                85                  90                  95

Gln Pro Leu Ala Pro Trp Thr Pro Tyr Thr Glu Tyr Val Pro His Glu
            100                 105                 110

Ala Val Ser Cys Pro Tyr Ser Ala Asp Met Tyr Val Gln Pro Val Cys
        115                 120                 125

Pro Ser Tyr Thr Val Val Gly Pro Ser Ser Val Leu Thr Tyr Ala Ser
    130                 135                 140

Pro Pro Leu Ile Thr Asn Val Thr Thr Arg Ser Ser Ala Thr Pro Ala
145                 150                 155                 160

Val Gly Pro Pro Leu Glu Gly Pro Glu His Gln Ala Pro Leu Thr Tyr
                165                 170                 175

Phe Pro Trp Pro Gln Pro Leu Ser Thr Leu Pro Thr Ser Thr Leu Gln
            180                 185                 190

Tyr Gln Pro Pro Ala Pro Ala Leu Pro Gly Pro Gln Phe Val Gln Leu
        195                 200                 205

Pro Ile Ser Ile Pro Glu Pro Val Leu Gln Asp Met Glu Asp Pro Arg
    210                 215                 220

Arg Ala Ala Ser Ser Leu Thr Ile Asp Lys Leu Leu Leu Glu Glu Glu
225                 230                 235                 240

Asp Ser Asp Ala Tyr Ala Leu Asn His Thr Leu Ser Val Glu Gly Phe
                245                 250                 255

<210> SEQ ID NO 17
<211> LENGTH: 263
<212> TYPE: PRT
<213> ORGANISM: Homo sapiens

<400> SEQUENCE: 17

Met Ile Thr Phe Leu Pro Leu Leu Gly Leu Ser Leu Gly Cys Thr
1               5                   10                  15

Gly Ala Gly Gly Phe Val Ala His Val Glu Ser Thr Cys Leu Leu Asp
                20                  25                  30

Asp Ala Gly Thr Pro Lys Asp Phe Thr Tyr Cys Ile Ser Phe Asn Lys
            35                  40                  45

Asp Leu Leu Thr Cys Trp Asp Pro Glu Glu Asn Lys Met Ala Pro Cys
50                  55                  60

Glu Phe Gly Val Leu Asn Ser Leu Ala Asn Val Leu Ser Gln His Leu
65                  70                  75                  80

Asn Gln Lys Asp Thr Leu Met Gln Arg Leu Arg Asn Gly Leu Gln Asn
                85                  90                  95

Cys Ala Thr His Thr Gln Pro Phe Trp Gly Ser Leu Thr Asn Arg Thr
            100                 105                 110

Arg Pro Pro Ser Val Gln Val Ala Lys Thr Thr Pro Phe Asn Thr Arg
        115                 120                 125

Glu Pro Val Met Leu Ala Cys Tyr Val Trp Gly Phe Tyr Pro Ala Glu
    130                 135                 140

Val Thr Ile Thr Trp Arg Lys Asn Gly Lys Leu Val Met Pro His Ser
145                 150                 155                 160

Ser Ala His Lys Thr Ala Gln Pro Asn Gly Asp Trp Thr Tyr Gln Thr
                165                 170                 175

Leu Ser His Leu Ala Leu Thr Pro Ser Tyr Gly Asp Thr Tyr Thr Cys
            180                 185                 190

Val Val Glu His Ile Gly Ala Pro Glu Pro Ile Leu Arg Asp Trp Thr
        195                 200                 205
```

```
Pro Gly Leu Ser Pro Met Gln Thr Leu Lys Val Ser Val Ser Ala Val
    210                 215                 220

Thr Leu Gly Leu Gly Leu Ile Ile Phe Ser Leu Gly Val Ile Ser Trp
225                 230                 235                 240

Arg Arg Ala Gly His Ser Ser Tyr Thr Pro Leu Pro Gly Ser Asn Tyr
                    245                 250                 255

Ser Glu Gly Trp His Ile Ser
                260

<210> SEQ ID NO 18
<211> LENGTH: 567
<212> TYPE: PRT
<213> ORGANISM: Homo sapiens

<400> SEQUENCE: 18

Met Ala Pro Leu Ala Leu His Leu Leu Val Leu Val Pro Ile Leu Leu
1               5                   10                  15

Ser Leu Val Ala Ser Gln Asp Trp Lys Ala Glu Arg Ser Gln Asp Pro
                20                  25                  30

Phe Glu Lys Cys Met Gln Asp Pro Asp Tyr Glu Gln Leu Leu Lys Val
            35                  40                  45

Val Thr Trp Gly Leu Asn Arg Thr Leu Lys Pro Gln Arg Val Ile Val
        50                  55                  60

Val Gly Ala Gly Val Ala Gly Leu Val Ala Ala Lys Val Leu Ser Asp
65                  70                  75                  80

Ala Gly His Lys Val Thr Ile Leu Glu Ala Asp Asn Arg Ile Gly Gly
                85                  90                  95

Arg Ile Phe Thr Tyr Arg Asp Gln Asn Thr Gly Trp Ile Gly Glu Leu
            100                 105                 110

Gly Ala Met Arg Met Pro Ser Ser His Arg Ile Leu His Lys Leu Cys
        115                 120                 125

Gln Gly Leu Gly Leu Asn Leu Thr Lys Phe Thr Gln Tyr Asp Lys Asn
130                 135                 140

Thr Trp Thr Glu Val His Glu Val Lys Leu Arg Asn Tyr Val Val Glu
145                 150                 155                 160

Lys Val Pro Glu Lys Leu Gly Tyr Ala Leu Arg Pro Gln Glu Lys Gly
                165                 170                 175

His Ser Pro Glu Asp Ile Tyr Gln Met Ala Leu Asn Gln Ala Leu Lys
            180                 185                 190

Asp Leu Lys Ala Leu Gly Cys Arg Lys Ala Met Lys Lys Phe Glu Arg
        195                 200                 205

His Thr Leu Leu Glu Tyr Leu Leu Gly Glu Gly Asn Leu Ser Arg Pro
210                 215                 220

Ala Val Gln Leu Leu Gly Asp Val Met Ser Glu Asp Gly Phe Phe Tyr
225                 230                 235                 240

Leu Ser Phe Ala Glu Ala Leu Arg Ala His Ser Cys Leu Ser Asp Arg
                245                 250                 255

Leu Gln Tyr Ser Arg Ile Val Gly Gly Trp Asp Leu Leu Pro Arg Ala
            260                 265                 270

Leu Leu Ser Ser Leu Ser Gly Leu Val Leu Asn Ala Pro Val Val
        275                 280                 285

Ala Met Thr Gln Gly Pro His Asp Val His Val Gln Ile Glu Thr Ser
290                 295                 300

Pro Pro Ala Arg Asn Leu Lys Val Leu Lys Ala Asp Val Val Leu Leu
305                 310                 315                 320
```

```
Thr Ala Ser Gly Pro Ala Val Lys Arg Ile Thr Phe Ser Pro Pro Leu
                325                 330                 335

Pro Arg His Met Gln Glu Ala Leu Arg Arg Leu His Tyr Val Pro Ala
            340                 345                 350

Thr Lys Val Phe Leu Ser Phe Arg Arg Pro Phe Trp Arg Glu Glu His
        355                 360                 365

Ile Glu Gly Gly His Ser Asn Thr Asp Arg Pro Ser Arg Met Ile Phe
370                 375                 380

Tyr Pro Pro Pro Arg Glu Gly Ala Leu Leu Ala Ser Tyr Thr Trp
385                 390                 395                 400

Ser Asp Ala Ala Ala Phe Ala Gly Leu Ser Arg Glu Glu Ala Leu
                405                 410                 415

Arg Leu Ala Leu Asp Asp Val Ala Leu His Gly Pro Val Val Arg
            420                 425                 430

Gln Leu Trp Asp Gly Thr Gly Val Val Lys Arg Trp Ala Glu Asp Gln
        435                 440                 445

His Ser Gln Gly Gly Phe Val Val Gln Pro Ala Leu Trp Gln Thr
    450                 455                 460

Glu Lys Asp Asp Trp Thr Val Pro Tyr Gly Arg Ile Tyr Phe Ala Gly
465                 470                 475                 480

Glu His Thr Ala Tyr Pro His Gly Trp Val Glu Thr Ala Val Lys Ser
                485                 490                 495

Ala Leu Arg Ala Ala Ile Lys Ile Asn Ser Arg Lys Gly Pro Ala Ser
            500                 505                 510

Asp Thr Ala Ser Pro Glu Gly His Ala Ser Asp Met Glu Gly Gln Gly
        515                 520                 525

His Val His Gly Val Ala Ser Ser Pro Ser His Asp Leu Ala Lys Glu
    530                 535                 540

Glu Gly Ser His Pro Pro Val Gln Gly Gln Leu Ser Leu Gln Asn Thr
545                 550                 555                 560

Thr His Thr Arg Thr Ser His
                565

<210> SEQ ID NO 19
<211> LENGTH: 899
<212> TYPE: PRT
<213> ORGANISM: Homo sapiens

<400> SEQUENCE: 19

Met Glu Ser Cys Tyr Asn Pro Gly Leu Asp Gly Ile Ile Glu Tyr Asp
1               5                   10                  15

Asp Phe Lys Leu Asn Ser Ser Ile Val Glu Pro Lys Glu Pro Ala Pro
            20                  25                  30

Glu Thr Ala Asp Gly Pro Tyr Leu Val Ile Val Glu Gln Pro Lys Gln
        35                  40                  45

Arg Gly Phe Arg Phe Arg Tyr Gly Cys Glu Gly Pro Ser His Gly Gly
    50                  55                  60

Leu Pro Gly Ala Ser Ser Glu Lys Gly Arg Lys Thr Tyr Pro Thr Val
65                  70                  75                  80

Lys Ile Cys Asn Tyr Glu Gly Pro Ala Lys Ile Glu Val Asp Leu Val
                85                  90                  95

Thr His Ser Asp Pro Pro Arg Ala His Ala His Ser Leu Val Gly Lys
            100                 105                 110

Gln Cys Ser Glu Leu Gly Ile Cys Ala Val Ser Val Gly Pro Lys Asp
        115                 120                 125
```

```
Met Thr Ala Gln Phe Asn Asn Leu Gly Val Leu His Val Thr Lys Lys
    130                 135                 140

Asn Met Met Gly Thr Met Ile Gln Lys Leu Gln Arg Gln Arg Leu Arg
145                 150                 155                 160

Ser Arg Pro Gln Gly Leu Thr Glu Ala Glu Gln Arg Glu Leu Glu Gln
                165                 170                 175

Glu Ala Lys Glu Leu Lys Lys Val Met Asp Leu Ser Ile Val Arg Leu
            180                 185                 190

Arg Phe Ser Ala Phe Leu Arg Ala Ser Asp Gly Ser Phe Ser Leu Pro
        195                 200                 205

Leu Lys Pro Val Ile Ser Gln Pro Ile His Asp Ser Lys Ser Pro Gly
    210                 215                 220

Ala Ser Asn Leu Lys Ile Ser Arg Met Asp Lys Thr Ala Gly Ser Val
225                 230                 235                 240

Arg Gly Gly Asp Glu Val Tyr Leu Leu Cys Asp Lys Val Gln Lys Asp
                245                 250                 255

Asp Ile Glu Val Arg Phe Tyr Glu Asp Glu Asn Gly Trp Gln Ala
            260                 265                 270

Phe Gly Asp Phe Ser Pro Thr Asp Val His Lys Gln Tyr Ala Ile Val
        275                 280                 285

Phe Arg Thr Pro Pro Tyr His Lys Met Lys Ile Glu Arg Pro Val Thr
    290                 295                 300

Val Phe Leu Gln Leu Lys Arg Lys Arg Gly Gly Asp Val Ser Asp Ser
305                 310                 315                 320

Lys Gln Phe Thr Tyr Tyr Pro Leu Val Glu Asp Lys Glu Glu Val Gln
                325                 330                 335

Arg Lys Arg Arg Lys Ala Leu Pro Thr Phe Ser Gln Pro Phe Gly Gly
            340                 345                 350

Gly Ser His Met Gly Gly Gly Ser Gly Gly Ala Ala Gly Gly Tyr Gly
        355                 360                 365

Gly Ala Gly Gly Gly Gly Ser Leu Gly Phe Phe Pro Ser Ser Leu Ala
    370                 375                 380

Tyr Ser Pro Tyr Gln Ser Gly Ala Gly Pro Met Gly Cys Tyr Pro Gly
385                 390                 395                 400

Gly Gly Gly Gly Ala Gln Met Ala Ala Thr Val Pro Ser Arg Asp Ser
                405                 410                 415

Gly Glu Glu Ala Ala Glu Pro Ser Ala Pro Ser Arg Thr Pro Gln Cys
            420                 425                 430

Glu Pro Gln Ala Pro Glu Met Leu Gln Arg Ala Arg Glu Tyr Asn Ala
        435                 440                 445

Arg Leu Phe Gly Leu Ala Gln Arg Ser Ala Arg Ala Leu Leu Asp Tyr
    450                 455                 460

Gly Val Thr Ala Asp Ala Arg Ala Leu Leu Ala Gly Gln Arg His Leu
465                 470                 475                 480

Leu Thr Ala Gln Asp Glu Asn Gly Asp Thr Pro Leu His Leu Ala Ile
                485                 490                 495

Ile His Gly Gln Thr Ser Val Ile Glu Gln Ile Val Tyr Val Ile His
            500                 505                 510

His Ala Gln Asp Leu Gly Val Val Asn Leu Thr Asn His Leu His Gln
        515                 520                 525

Thr Pro Leu His Leu Ala Val Ile Thr Gly Gln Thr Ser Val Val Ser
    530                 535                 540

Phe Leu Leu Arg Val Gly Ala Asp Pro Ala Leu Leu Asp Arg His Gly
```

```
                545                 550                 555                 560
Asp Ser Ala Met His Leu Ala Leu Arg Ala Gly Ala Gly Ala Pro Glu
                565                 570                 575

Leu Leu Arg Ala Leu Leu Gln Ser Gly Ala Pro Ala Val Pro Gln Leu
            580                 585                 590

Leu His Met Pro Asp Phe Glu Gly Leu Tyr Pro Val His Leu Ala Val
        595                 600                 605

Arg Ala Arg Ser Pro Glu Cys Leu Asp Leu Leu Val Asp Ser Gly Ala
    610                 615                 620

Glu Val Glu Ala Thr Glu Arg Gln Gly Gly Arg Thr Ala Leu His Leu
625                 630                 635                 640

Ala Thr Glu Met Glu Glu Leu Gly Leu Val Thr His Leu Val Thr Lys
                645                 650                 655

Leu Arg Ala Asn Val Asn Ala Arg Thr Phe Ala Gly Asn Thr Pro Leu
            660                 665                 670

His Leu Ala Ala Gly Leu Gly Tyr Pro Thr Leu Thr Arg Leu Leu Leu
        675                 680                 685

Lys Ala Gly Ala Asp Ile His Ala Glu Asn Glu Glu Pro Leu Cys Pro
    690                 695                 700

Leu Pro Ser Pro Pro Thr Ser Asp Ser Asp Ser Asp Ser Glu Gly Pro
705                 710                 715                 720

Glu Lys Asp Thr Arg Ser Ser Phe Arg Gly His Thr Pro Leu Asp Leu
                725                 730                 735

Thr Cys Ser Thr Lys Val Lys Thr Leu Leu Leu Asn Ala Ala Gln Asn
            740                 745                 750

Thr Met Glu Pro Pro Leu Thr Pro Pro Ser Pro Ala Gly Pro Gly Leu
        755                 760                 765

Ser Leu Gly Asp Thr Ala Leu Gln Asn Leu Glu Gln Leu Leu Asp Gly
    770                 775                 780

Pro Glu Ala Gln Gly Ser Trp Ala Glu Leu Ala Glu Arg Leu Gly Leu
785                 790                 795                 800

Arg Ser Leu Val Asp Thr Tyr Arg Gln Thr Thr Ser Pro Ser Gly Ser
                805                 810                 815

Leu Leu Arg Ser Tyr Glu Leu Ala Gly Gly Asp Leu Ala Gly Leu Leu
            820                 825                 830

Glu Ala Leu Ser Asp Met Gly Leu Glu Glu Gly Val Arg Leu Leu Arg
        835                 840                 845

Gly Pro Glu Thr Arg Asp Lys Leu Pro Ser Thr Glu Val Lys Glu Asp
    850                 855                 860

Ser Ala Tyr Gly Ser Gln Ser Val Glu Gln Glu Ala Glu Lys Leu Gly
865                 870                 875                 880

Pro Pro Pro Glu Pro Pro Gly Gly Leu Cys His Gly His Pro Gln Pro
                885                 890                 895

Gln Val His

<210> SEQ ID NO 20
<211> LENGTH: 321
<212> TYPE: PRT
<213> ORGANISM: Homo sapiens

<400> SEQUENCE: 20

Met Glu Glu Gly Gln Tyr Ser Glu Ile Glu Glu Leu Pro Arg Arg Arg
1               5                   10                  15

Cys Cys Arg Arg Gly Thr Gln Ile Val Leu Leu Gly Leu Val Thr Ala
            20                  25                  30
```

```
Ala Leu Trp Ala Gly Leu Leu Thr Leu Leu Leu Trp His Trp Asp
        35                  40                  45

Thr Thr Gln Ser Leu Lys Gln Leu Glu Glu Arg Ala Ala Arg Asn Val
 50                  55                  60

Ser Gln Val Ser Lys Asn Leu Glu Ser His His Gly Asp Gln Met Ala
 65                  70                  75                  80

Gln Lys Ser Gln Ser Thr Gln Ile Ser Gln Glu Leu Glu Glu Leu Arg
                 85                  90                  95

Ala Glu Gln Gln Arg Leu Lys Ser Gln Asp Leu Glu Leu Ser Trp Asn
            100                 105                 110

Leu Asn Gly Leu Gln Ala Asp Leu Ser Ser Phe Lys Ser Gln Glu Leu
        115                 120                 125

Asn Glu Arg Asn Glu Ala Ser Asp Leu Leu Glu Arg Leu Arg Glu Glu
    130                 135                 140

Val Thr Lys Leu Arg Met Glu Leu Gln Val Ser Ser Gly Phe Val Cys
145                 150                 155                 160

Asn Thr Cys Pro Glu Lys Trp Ile Asn Phe Gln Arg Lys Cys Tyr Tyr
                165                 170                 175

Phe Gly Lys Gly Thr Lys Gln Trp Val His Ala Arg Tyr Ala Cys Asp
            180                 185                 190

Asp Met Glu Gly Gln Leu Val Ser Ile His Ser Pro Glu Glu Gln Asp
        195                 200                 205

Phe Leu Thr Lys His Ala Ser His Thr Gly Ser Trp Ile Gly Leu Arg
    210                 215                 220

Asn Leu Asp Leu Lys Gly Glu Phe Ile Trp Val Asp Gly Ser His Val
225                 230                 235                 240

Asp Tyr Ser Asn Trp Ala Pro Gly Glu Pro Thr Ser Arg Ser Gln Gly
                245                 250                 255

Glu Asp Cys Val Met Met Arg Gly Ser Gly Arg Trp Asn Asp Ala Phe
            260                 265                 270

Cys Asp Arg Lys Leu Gly Ala Trp Val Cys Asp Arg Leu Ala Thr Cys
        275                 280                 285

Thr Pro Pro Ala Ser Glu Gly Ser Ala Glu Ser Met Gly Pro Asp Ser
    290                 295                 300

Arg Pro Asp Pro Asp Gly Arg Leu Pro Thr Pro Ser Ala Pro Leu His
305                 310                 315                 320

Ser

<210> SEQ ID NO 21
<211> LENGTH: 186
<212> TYPE: PRT
<213> ORGANISM: Homo sapiens
<220> FEATURE:
<221> NAME/KEY: misc_feature
<222> LOCATION: (1)..(1)
<223> OTHER INFORMATION: None, or any amino acid
<220> FEATURE:
<221> NAME/KEY: misc_feature
<222> LOCATION: (2)..(2)
<223> OTHER INFORMATION: Methionine, none, or any amino acid
<220> FEATURE:
<221> NAME/KEY: misc_feature
<222> LOCATION: (21)..(21)
<223> OTHER INFORMATION: Valine (wild type), asparagine, or another
      amino acid
<220> FEATURE:
<221> NAME/KEY: misc_feature
<222> LOCATION: (28)..(28)
<223> OTHER INFORMATION: Leucine (wild type), proline, or another amino
      acid
```

```
<220> FEATURE:
<221> NAME/KEY: misc_feature
<222> LOCATION: (47)..(47)
<223> OTHER INFORMATION: None, any amino acid, or alanine

<400> SEQUENCE: 21

Xaa Xaa Arg Arg Gly Pro Arg Ser Leu Arg Gly Arg Asp Ala Pro Ala
1               5                   10                  15

Pro Thr Pro Cys Xaa Pro Ala Glu Cys Phe Asp Xaa Leu Val Arg His
            20                  25                  30

Cys Val Ala Cys Gly Leu Leu Arg Thr Pro Arg Pro Lys Pro Xaa Ala
            35                  40                  45

Gly Ala Ser Ser Pro Ala Pro Arg Thr Ala Leu Gln Pro Gln Glu Ser
        50                  55                  60

Val Gly Ala Gly Ala Gly Glu Ala Ala Leu Pro Leu Pro Gly Leu Leu
65                  70                  75                  80

Phe Gly Ala Pro Ala Leu Leu Gly Leu Ala Leu Val Leu Ala Leu Val
                85                  90                  95

Leu Val Gly Leu Val Ser Trp Arg Arg Gln Arg Arg Leu Arg Gly
            100                 105                 110

Ala Ser Ser Ala Glu Ala Pro Asp Gly Asp Lys Asp Ala Pro Glu Pro
            115                 120                 125

Leu Asp Lys Val Ile Ile Leu Ser Pro Gly Ile Ser Asp Ala Thr Ala
130                 135                 140

Pro Ala Trp Pro Pro Gly Glu Asp Pro Gly Thr Thr Pro Pro Gly
145                 150                 155                 160

His Ser Val Pro Val Pro Ala Thr Glu Leu Gly Ser Thr Glu Leu Val
                165                 170                 175

Thr Thr Lys Thr Ala Gly Pro Glu Gln Gln
            180                 185

<210> SEQ ID NO 22
<211> LENGTH: 321
<212> TYPE: PRT
<213> ORGANISM: Homo sapiens
<220> FEATURE:
<221> NAME/KEY: misc_feature
<222> LOCATION: (41)..(41)
<223> OTHER INFORMATION: Valine, aspragine, or another amino acid
<220> FEATURE:
<221> NAME/KEY: misc_feature
<222> LOCATION: (48)..(48)
<223> OTHER INFORMATION: Leucine (wild type), proline, or another amino
      acid
<220> FEATURE:
<221> NAME/KEY: misc_feature
<222> LOCATION: (67)..(67)
<223> OTHER INFORMATION: None, any amino acid, or alanine

<400> SEQUENCE: 22

Met Glu Thr Asp Thr Leu Leu Leu Trp Val Leu Leu Leu Trp Val Pro
1               5                   10                  15

Gly Ser Thr Gly Asp Val Arg Arg Gly Pro Arg Ser Leu Arg Gly Arg
            20                  25                  30

Asp Ala Pro Ala Pro Thr Pro Cys Xaa Pro Ala Glu Cys Phe Asp Xaa
            35                  40                  45

Leu Val Arg His Cys Val Ala Cys Gly Leu Leu Arg Thr Pro Arg Pro
        50                  55                  60

Lys Pro Xaa Ala Gly Ala Ser Ser Pro Ala Pro Arg Thr Ala Leu Gln
65                  70                  75                  80

Pro Gln Glu Ser Val Gly Ala Gly Ala Gly Glu Ala Ala Val Asp Lys
```

```
                85                  90                  95
Thr His Thr Ser Pro Ser Pro Ala Pro Glu Leu Leu Gly Gly Pro
            100                 105                 110

Ser Val Phe Leu Phe Pro Pro Lys Pro Lys Asp Thr Leu Met Ile Ser
            115                 120                 125

Arg Thr Pro Glu Val Thr Cys Val Val Val Asp Val Ser His Glu Asp
            130                 135                 140

Pro Glu Val Lys Phe Asn Trp Tyr Val Asp Gly Val Glu Val His Asn
145                 150                 155                 160

Ala Lys Thr Lys Pro Arg Glu Glu Gln Tyr Asn Ser Thr Tyr Arg Val
                165                 170                 175

Val Ser Val Leu Thr Val Leu His Gln Asp Trp Leu Asn Gly Lys Glu
            180                 185                 190

Tyr Lys Cys Lys Val Ser Asn Lys Ala Leu Pro Ala Pro Ile Glu Lys
            195                 200                 205

Thr Ile Ser Lys Ala Lys Gly Gln Pro Arg Glu Pro Gln Val Tyr Thr
            210                 215                 220

Leu Pro Pro Ser Arg Asp Glu Leu Thr Lys Asn Gln Val Ser Leu Thr
225                 230                 235                 240

Cys Leu Val Lys Gly Phe Tyr Pro Ser Asp Ile Ala Val Glu Trp Glu
                245                 250                 255

Ser Asn Gly Gln Pro Glu Asn Asn Tyr Lys Thr Thr Pro Pro Val Leu
            260                 265                 270

Asp Ser Asp Gly Ser Phe Phe Leu Tyr Ser Lys Leu Thr Val Asp Lys
            275                 280                 285

Ser Arg Trp Gln Gln Gly Asn Val Phe Ser Cys Ser Val Met His Glu
            290                 295                 300

Ala Leu His Asn His Tyr Thr Gln Lys Ser Leu Ser Leu Ser Pro Gly
305                 310                 315                 320

Lys

<210> SEQ ID NO 23
<211> LENGTH: 175
<212> TYPE: PRT
<213> ORGANISM: Mus musculus

<400> SEQUENCE: 23

Met Gly Ala Arg Arg Leu Arg Val Arg Ser Gln Arg Ser Arg Asp Ser
1               5                   10                  15

Ser Val Pro Thr Gln Cys Asn Gln Thr Glu Cys Phe Asp Pro Leu Val
            20                  25                  30

Arg Asn Cys Val Ser Cys Glu Leu Phe His Thr Pro Asp Thr Gly His
            35                  40                  45

Thr Ser Ser Leu Glu Pro Gly Thr Ala Leu Gln Pro Gln Glu Gly Ser
        50                  55                  60

Ala Leu Arg Pro Asp Val Ala Leu Leu Val Gly Ala Pro Ala Leu Leu
65                  70                  75                  80

Gly Leu Ile Leu Ala Leu Thr Leu Val Gly Leu Val Ser Leu Val Ser
                85                  90                  95

Trp Arg Trp Arg Gln Gln Leu Arg Thr Ala Ser Pro Asp Thr Ser Glu
            100                 105                 110

Gly Val Gln Gln Glu Ser Leu Glu Asn Val Phe Val Pro Ser Ser Glu
            115                 120                 125

Thr Pro His Ala Ser Ala Pro Thr Trp Pro Pro Leu Lys Glu Asp Ala
            130                 135                 140
```

```
Asp Ser Ala Leu Pro Arg His Ser Val Pro Val Pro Ala Thr Glu Leu
145                 150                 155                 160

Gly Ser Thr Glu Leu Val Thr Thr Lys Thr Ala Gly Pro Glu Gln
            165                 170                 175

<210> SEQ ID NO 24
<211> LENGTH: 316
<212> TYPE: PRT
<213> ORGANISM: Mus musculus

<400> SEQUENCE: 24

Met Glu Thr Asp Thr Leu Leu Leu Trp Val Leu Leu Leu Trp Val Pro
1               5                   10                  15

Gly Ser Thr Gly Asp Val Gly Ala Arg Arg Leu Arg Val Arg Ser Gln
            20                  25                  30

Arg Ser Arg Asp Ser Ser Val Pro Thr Gln Cys Asn Gln Thr Glu Cys
        35                  40                  45

Phe Asp Pro Leu Val Arg Asn Cys Val Ser Cys Glu Leu Phe His Thr
    50                  55                  60

Pro Asp Thr Gly His Thr Ser Ser Leu Glu Pro Gly Thr Ala Leu Gln
65                  70                  75                  80

Pro Gln Glu Gly Ser Ala Leu Val Asp Val Pro Arg Asp Cys Gly Cys
                85                  90                  95

Lys Pro Cys Ile Cys Thr Val Pro Glu Val Ser Ser Val Phe Ile Phe
            100                 105                 110

Pro Pro Lys Pro Lys Asp Val Leu Thr Ile Thr Leu Thr Pro Lys Val
        115                 120                 125

Thr Cys Val Val Asp Ile Ser Lys Asp Asp Pro Glu Val Gln Phe
130                 135                 140

Ser Trp Phe Val Asp Asp Val Glu Val His Thr Ala Gln Thr Gln Pro
145                 150                 155                 160

Arg Glu Glu Gln Phe Asn Ser Thr Phe Arg Ser Val Ser Glu Leu Pro
                165                 170                 175

Ile Met His Gln Asp Trp Leu Asn Gly Lys Glu Phe Lys Cys Arg Val
            180                 185                 190

Asn Ser Ala Ala Phe Pro Ala Pro Ile Glu Lys Thr Ile Ser Lys Thr
        195                 200                 205

Lys Gly Arg Pro Lys Ala Pro Gln Val Tyr Thr Ile Pro Pro Pro Lys
    210                 215                 220

Glu Gln Met Ala Lys Asp Lys Val Ser Leu Thr Cys Met Ile Thr Asp
225                 230                 235                 240

Phe Phe Pro Glu Asp Ile Thr Val Glu Trp Gln Trp Asn Gly Gln Pro
                245                 250                 255

Ala Glu Asn Tyr Lys Asn Thr Gln Pro Ile Met Asp Thr Asp Gly Ser
            260                 265                 270

Tyr Phe Val Tyr Ser Lys Leu Asn Val Gln Lys Ser Asn Trp Glu Ala
        275                 280                 285

Gly Asn Thr Phe Thr Cys Ser Val Leu His Glu Gly Leu His Asn His
    290                 295                 300

His Thr Glu Lys Ser Leu Ser His Ser Pro Gly Lys
305                 310                 315

<210> SEQ ID NO 25
<211> LENGTH: 11
<212> TYPE: PRT
<213> ORGANISM: Homo sapiens
```

<400> SEQUENCE: 25

Cys His Trp Asp Leu Leu Arg His Trp Val Cys
1               5                   10

<210> SEQ ID NO 26
<211> LENGTH: 298
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: None, RRGPRSLRGR, or other amino acids.
<220> FEATURE:
<221> NAME/KEY: MISC_FEATURE
<222> LOCATION: (6)..(10)
<223> OTHER INFORMATION: None, SLRGR, or other amino acids.
<220> FEATURE:
<221> NAME/KEY: MISC_FEATURE
<222> LOCATION: (19)..(19)
<223> OTHER INFORMATION: Valine (wild type), asparagine, or another
      amino acid.
<220> FEATURE:
<221> NAME/KEY: MISC_FEATURE
<222> LOCATION: (26)..(26)
<223> OTHER INFORMATION: Leucine (wild type), proline, or another amino
      acid.
<220> FEATURE:
<221> NAME/KEY: MISC_FEATURE
<222> LOCATION: (45)..(45)
<223> OTHER INFORMATION: None, any amino acid, or alanine
<220> FEATURE:
<221> NAME/KEY: MISC_FEATURE
<222> LOCATION: (72)..(72)
<223> OTHER INFORMATION: None, any amino acid, e.g., valine.

<400> SEQUENCE: 26

Xaa Xaa Xaa Xaa Xaa Xaa Xaa Xaa Xaa Asp Ala Pro Ala Pro Thr
1               5                   10                  15

Pro Cys Xaa Pro Ala Glu Cys Phe Asp Xaa Leu Val Arg His Cys Val
                20                  25                  30

Ala Cys Gly Leu Leu Arg Thr Pro Arg Pro Lys Pro Xaa Ala Gly Ala
            35                  40                  45

Ser Ser Pro Ala Pro Arg Thr Ala Leu Gln Pro Gln Glu Ser Val Gly
    50                  55                  60

Ala Gly Ala Gly Glu Ala Ala Xaa Asp Lys Thr His Thr Ser Pro Pro
65                  70                  75                  80

Ser Pro Ala Pro Glu Leu Leu Gly Gly Pro Ser Val Phe Leu Phe Pro
                85                  90                  95

Pro Lys Pro Lys Asp Thr Leu Met Ile Ser Arg Thr Pro Glu Val Thr
                100                 105                 110

Cys Val Val Val Asp Val Ser His Glu Asp Pro Glu Val Lys Phe Asn
            115                 120                 125

Trp Tyr Val Asp Gly Val Glu Val His Asn Ala Lys Thr Lys Pro Arg
130                 135                 140

Glu Glu Gln Tyr Asn Ser Thr Tyr Arg Val Val Ser Val Leu Thr Val
145                 150                 155                 160

Leu His Gln Asp Trp Leu Asn Gly Lys Glu Tyr Lys Cys Lys Val Ser
                165                 170                 175

Asn Lys Ala Leu Pro Ala Pro Ile Glu Lys Thr Ile Ser Lys Ala Lys
                180                 185                 190

Gly Gln Pro Arg Glu Pro Gln Val Tyr Thr Leu Pro Pro Ser Arg Asp
            195                 200                 205

Glu Leu Thr Lys Asn Gln Val Ser Leu Thr Cys Leu Val Lys Gly Phe

```
                210                 215                 220
Tyr Pro Ser Asp Ile Ala Val Glu Trp Glu Ser Asn Gly Gln Pro Glu
225                 230                 235                 240

Asn Asn Tyr Lys Thr Thr Pro Pro Val Leu Asp Ser Asp Gly Ser Phe
            245                 250                 255

Phe Leu Tyr Ser Lys Leu Thr Val Asp Lys Ser Arg Trp Gln Gln Gly
        260                 265                 270

Asn Val Phe Ser Cys Ser Val Met His Glu Ala Leu His Asn His Tyr
    275                 280                 285

Thr Gln Lys Ser Leu Ser Leu Ser Pro Gly
    290                 295
```

<210> SEQ ID NO 27
<211> LENGTH: 184
<212> TYPE: PRT
<213> ORGANISM: Homo sapiens

<400> SEQUENCE: 27

```
Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Ser Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180
```

<210> SEQ ID NO 28
<211> LENGTH: 293
<212> TYPE: PRT
<213> ORGANISM: Homo sapiens

<400> SEQUENCE: 28

```
Met Ser Gly Leu Gly Arg Ser Arg Arg Gly Gly Arg Ser Arg Val Asp
1               5                   10                  15

Gln Glu Glu Arg Phe Pro Gln Gly Leu Trp Thr Gly Val Ala Met Arg
            20                  25                  30

Ser Cys Pro Glu Glu Gln Tyr Trp Asp Pro Leu Leu Gly Thr Cys Met
        35                  40                  45

Ser Cys Lys Thr Ile Cys Asn His Gln Ser Gln Arg Thr Cys Ala Ala
    50                  55                  60
```

```
Phe Cys Arg Ser Leu Ser Cys Arg Lys Glu Gln Gly Lys Phe Tyr Asp
 65                  70                  75                  80

His Leu Leu Arg Asp Cys Ile Ser Cys Ala Ser Ile Cys Gly Gln His
                 85                  90                  95

Pro Lys Gln Cys Ala Tyr Phe Cys Glu Asn Lys Leu Arg Ser Pro Val
            100                 105                 110

Asn Leu Pro Pro Glu Leu Arg Arg Gln Arg Ser Gly Glu Val Glu Asn
        115                 120                 125

Asn Ser Asp Asn Ser Gly Arg Tyr Gln Gly Leu Glu His Arg Gly Ser
    130                 135                 140

Glu Ala Ser Pro Ala Leu Pro Gly Leu Lys Leu Ser Ala Asp Gln Val
145                 150                 155                 160

Ala Leu Val Tyr Ser Thr Leu Gly Leu Cys Leu Cys Ala Val Leu Cys
                165                 170                 175

Cys Phe Leu Val Ala Val Ala Cys Phe Leu Lys Lys Arg Gly Asp Pro
            180                 185                 190

Cys Ser Cys Gln Pro Arg Ser Arg Pro Arg Gln Ser Pro Ala Lys Ser
        195                 200                 205

Ser Gln Asp His Ala Met Glu Ala Gly Ser Pro Val Ser Thr Ser Pro
    210                 215                 220

Glu Pro Val Glu Thr Cys Ser Phe Cys Phe Pro Glu Cys Arg Ala Pro
225                 230                 235                 240

Thr Gln Glu Ser Ala Val Thr Pro Gly Thr Pro Asp Pro Thr Cys Ala
                245                 250                 255

Gly Arg Trp Gly Cys His Thr Arg Thr Thr Val Leu Gln Pro Cys Pro
            260                 265                 270

His Ile Pro Asp Ser Gly Leu Gly Ile Val Cys Val Pro Ala Gln Glu
        275                 280                 285

Gly Gly Pro Gly Ala
    290

<210> SEQ ID NO 29
<211> LENGTH: 63
<212> TYPE: DNA
<213> ORGANISM: Artificial Sequence
<220> FEATURE:
<223> OTHER INFORMATION: T7 primer

<400> SEQUENCE: 29
ggccagtgaa ttgtaatacg actcactata gggaggcggt tttttttttt tttttttttt    60
ttt                                                                  63
```

The invention claimed is:

1. A method for monitoring efficacy of an antagonist to BAFF (SEQ ID NO:30) in a human, comprising the steps of administering the BAFF antagonist to the human, obtaining from the human a biological sample comprising B cells, and detecting a level in the biological sample of one or more molecules selected from the group consisting of:
   (a) a polypeptide comprising a sequence selected from SEQ ID NO:16, SEQ ID NO:17, and SEQ ID NO:18; and
   (b) an mRNA comprising a nucleotide sequence encoding an amino acid sequence selected from SEQ ID NO:16, SEQ ID NO:17, and SEQ ID NO:18,
   wherein the level, relative to a control, of at least one of the detected molecules indicates efficacy of the BAFF antagonist in the human, and wherein the BAFF antagonist inhibits the interaction between BAFF and a BAFF receptor and is selected from the group consisting of an anti-BAFF antibody, an anti-BAFF-R antibody, and a BAFF-R-Fc polypeptide.

2. The method for monitoring efficacy of a BAFF antagonist in a human according to claim 1, wherein the method further comprises the step of detecting a level in the biological sample of one or more molecules selected from the group consisting of
   (a) a polypeptide comprising a sequence selected from SEQ ID NO:19 and SEQ ID NO:20; and
   (b) an mRNA encoding an amino acid sequence selected from SEQ ID NO:19 and SEQ ID NO:20;

wherein the level, relative to a control, of at least one of the detected molecules indicates efficacy of the BAFF antagonist in the human.

3. The method according to claim 1, wherein the human is suffering from an autoimmune disease.

4. The method according to claim 3, wherein the autoimmune disease is selected from the group consisting of rheumatoid arthritis, lupus, and Sjogren's disease.

5. The method for monitoring efficacy of a BAFF antagonist in a human according to claim 1, further comprising the step of detecting a level in the biological sample of at least one molecule selected from the group consisting of BAFF (SEQ ID NO:30) and an mRNA encoding BAFF, wherein the level, relative to a control, of at least one of the detected molecules indicates efficacy of the BAFF antagonist in the human.

6. The method for monitoring efficacy of a BAFF antagonist in a human according to claim 1, further comprising the step of detecting a level in the biological sample of at least one molecule selected from the group consisting of BAFF-R (SEQ ID NO:23) and an mRNA encoding BAFF-R, wherein the level, relative to a control, of at least one of the detected molecules indicates efficacy of the BAFF antagonist human.

7. The method according to a claim 1, wherein the molecule is a polypeptide comprising the sequence of SEQ ID NO:16 or an mRNA comprising a sequence encoding SEQ ID NO:16.

\* \* \* \* \*

UNITED STATES PATENT AND TRADEMARK OFFICE
CERTIFICATE OF CORRECTION

PATENT NO. : 8,617,545 B2
APPLICATION NO. : 12/083614
DATED : December 31, 2013
INVENTOR(S) : Yen-Ming Hsu et al.

It is certified that error appears in the above-identified patent and that said Letters Patent is hereby corrected as shown below:

In the Specification

In the Sequence Listing, columns 27-28, line 1:

" <160>  NUMBER OF SEQ ID NOS:  29 "

should read:

-- <160> NUMBER OF SEQ ID NOS: 30 --

In the Sequence Listing, columns 81-82, line 36, for SEQ ID NO 29:

" <223>  OTHER INFORMATION: T7 primer "

should read:

-- <223>  OTHER INFORMATION: Synthetic Primer --

Signed and Sealed this
Seventeenth Day of June, 2014

Michelle K. Lee
*Deputy Director of the United States Patent and Trademark Office*

CERTIFICATE OF CORRECTION (continued)
U.S. Pat. No. 8,617,545 B2

In the Sequence Listing, columns 81-82, after SEQ ID NO 29, and before the claims, the following SEQ ID NO 30 should be added:

```
<210> SEQ ID NO 30
<211> LENGTH: 218
<212> TYPE:  PRT
<213> ORGANISM:  Homo sapiens

<400> SEQUENCE:  30

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Leu Leu Ser Cys Cys Leu Thr Val Val
            35                  40                  45

Ser Phe Tyr Gln Val Ala Ala Leu Gln Gly Asp Leu Ala Ser Leu Arg
        50                  55                  60

Ala Glu Leu Gln Gly His His Ala Glu Lys Leu Pro Ala Gly Ala Lys
65                  70                  75                  80

Ile Phe Glu Pro Pro Ala Pro Gly Glu Gly Asn Ser Ser Gln Asn Ser
                85                  90                  95

Arg Asn Lys Arg Ala Val Gln Gly Pro Glu Glu Thr Val Thr Gln Asp
            100                 105                 110

Cys Leu Gln Leu Ile Ala Asp Ser Glu Thr Pro Thr Ile Gln Lys Gly
        115                 120                 125

Ser Tyr Thr Phe Val Pro Trp Leu Leu Ser Phe Lys Arg Gly Ser Ala
    130                 135                 140

Leu Tyr Gly Gln Val Leu Tyr Thr Asp Lys Thr Tyr Ala Met Gly His
145                 150                 155                 160

Leu Ile Gln Arg Lys Lys Val His Val Phe Gly Asp Glu Leu Ser Leu
                165                 170                 175

Val Thr Leu Phe Arg Cys Ile Gln Asn Leu Glu Glu Gly Asp Glu Leu
            180                 185                 190

Gln Leu Ala Ile Pro Arg Glu Asn Ala Gln Ile Ser Leu Asp Gly Asp
        195                 200                 205

Val Thr Phe Phe Gly Ala Leu Lys Leu Leu
--      210                 215                                 --
```

UNITED STATES PATENT AND TRADEMARK OFFICE
CERTIFICATE OF CORRECTION

| | | |
|---|---|---|
| PATENT NO. | : 8,617,545 B2 | Page 1 of 1 |
| APPLICATION NO. | : 12/083614 | |
| DATED | : December 31, 2013 | |
| INVENTOR(S) | : Hsu et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1553 days.

Signed and Sealed this
Ninth Day of June, 2015

Michelle K. Lee
*Director of the United States Patent and Trademark Office*